(12) United States Patent
Garvey

(10) Patent No.: US 7,138,430 B2
(45) Date of Patent: Nov. 21, 2006

(54) NITROSATED AND NITROSYLATED NEBIVOLOL AND ITS METABOLITES, COMPOSITIONS AND METHODS OF USE

(75) Inventor: David S. Garvey, Dover, MA (US)

(73) Assignee: NitroMed, Inc., Lexington, MA (US)

(*) Notice: Subject to any disclaimer, the term of this patent is extended or adjusted under 35 U.S.C. 154(b) by 63 days.

(21) Appl. No.: 10/695,644

(22) Filed: Oct. 29, 2003

(65) Prior Publication Data
US 2004/0132805 A1  Jul. 8, 2004

Related U.S. Application Data

(63) Continuation of application No. PCT/US02/13667, filed on May 1, 2002.

(60) Provisional application No. 60/287,725, filed on May 2, 2001.

(51) Int. Cl.
*A61K 31/352* (2006.01)
*C07D 311/04* (2006.01)

(52) U.S. Cl. .................. 514/456; 549/407; 549/401
(58) Field of Classification Search ............. 514/456; 549/407, 401
See application file for complete search history.

(56) References Cited

U.S. PATENT DOCUMENTS

| 4,654,362 | A | 3/1987 | Van Lommen et al. |
| 5,759,580 | A | 6/1998 | Jans et al. |
| 5,874,461 | A | 2/1999 | de Chaffoy de Courcelles et al. |
| 6,075,046 | A | 6/2000 | De Chaffoy ... |
| 6,635,273 | B1* | 10/2003 | Loscalzo et al. ............ 424/444 |

FOREIGN PATENT DOCUMENTS

| WO | WO 95/22325 | 8/1995 |
| WO | WO 96/19987 | 7/1996 |
| WO | WO 98/21193 | 5/1998 |
| WO | WO 99/00361 | 1/1999 |
| WO | WO 99/67231 | 12/1999 |
| WO | WO-00/49993 | 8/2000 |
| WO | WO 00/51988 | 8/2000 |
| WO | WO-00/51978 | 9/2000 |
| WO | WO 00/61537 | 10/2000 |
| WO | WO 00/61541 | 10/2000 |
| WO | WO 00/61549 | 10/2000 |
| WO | WO-00/67754 | 11/2000 |
| WO | WO 01/12584 | 2/2001 |
| WO | WO 02/051385 | 7/2002 |
| WO | 2005/053685 A1 | 6/2005 |
| WO | 2005/054218 | 6/2005 |

OTHER PUBLICATIONS

Jun. 5, 2003. International Search Report for PCT/US02/13667.
Kakoki, Masao et al. Jan. 1999. "Effects of Vasodilatory β-Adrenoceptor Antagonists on Endothelium-Derived Nitric Oxide Release in Rat Kidney." *Hypertension.* vol. 33, part II. pp. 467-471.
Brehm, B. R. et al. 2001. "Effects of nebivolol on proliferation and apoptosis of human coronary artery smooth muscle and endothelial cells." *Cardiovascular Research.* vol. 49. pp. 430-439.
Sep. 7, 2004. Supplementary European Search Report from European Patent Application No. 02766876.3.

* cited by examiner

*Primary Examiner*—Charanjit S. Aulakh
(74) *Attorney, Agent, or Firm*—Wilmer Cutler Pickering Hale and Dorr LLP

(57) ABSTRACT

The invention describes novel nitrosated and/or nitrosylated nebivolol, novel nitrosated and/or nitrosylated metabolites of nebivolol and novel compositions comprising at least one nitrosated and/or nitrosylated nebivolol and/or at least one nitrosated and/or nitrosylated metabolite of nebivolol, and, optionally, at least one nitric oxide donor and/or at least one antioxidant or a pharmaceutically acceptable salt thereof, and/or at least one compound used to treat cardiovascular diseases or a pharmaceutically acceptable salt thereof, and/or at least one nitrosated compound used to treat cardiovascular diseases. The invention also provides novel compositions comprising nebivolol and/or at least one metabolite of nebivolol and at least one nitric oxide donor, and, optionally, at least one antioxidant or a pharmaceutically acceptable salt thereof, and/or at least one compound used to treat cardiovascular diseases or a pharmaceutically acceptable salt thereof, and/or at least one nitrosated compound used to treat cardiovascular diseases. The compounds and compositions of the invention can also be bound to a matrix. The nitric oxide donor is a compound that donates, transfers or releases nitric oxide, elevates endogenous levels of endothelium-derived relaxing factor, stimulates endogenous synthesis of nitric oxide or is a substrate for nitric oxide synthase and may preferably be isosorbide dinitrate and/or isosorbide mononitrate. The antioxidant may preferably be a hydralazine compound or a pharmaceutically acceptable salt thereof. The invention also provides methods for treating and/or preventing vascular diseases characterized by nitric oxide insufficiency; and for treating and/or preventing Raynaud's syndrome; and for treating and/or preventing cardiovascular diseases or disorders.

10 Claims, 16 Drawing Sheets

NITROSATED AND NITROSYLATED NEBIVOLOL AND ITS METABOLITES, COMPOSITIONS AND METHODS OF USE

RELATED APPLICATIONS

This application is a continuation of International Application No. PCT/US02/13667, filed May 1, 2002, which was published under PCT Article 21(2) in English and is incorporated herein by reference. International Application No. PCT/US02/13667 claims priority from U.S. Provisional Application No. 60/287,725, filed May 2, 2001.

FIELD OF THE INVENTION

The invention describes novel nitrosated and/or nitrosylated nebivolol, novel nitrosated and/or nitrosylated metabolites of nebivolol and novel compositions comprising at least one nitrosated and/or nitrosylated nebivolol and/or at least one nitrosated and/or nitrosylated metabolite of nebivolol, and, optionally, at least one nitric oxide donor and/or at least one antioxidant or a pharmaceutically acceptable salt thereof, and/or at least one compound used to treat cardiovascular diseases or a pharmaceutically acceptable salt thereof, and/or at least one nitrosated compound used to treat cardiovascular diseases. The invention also provides novel compositions comprising nebivolol and/or at least one metabolite of nebivolol and at least one nitric oxide donor, and, optionally, at least one antioxidant or a pharmaceutically acceptable salt thereof, and/or at least one compound used to treat cardiovascular diseases or a pharmaceutically acceptable salt thereof, and/or at least one nitrosated compound used to treat cardiovascular diseases. The compounds and compositions of the invention can also be bound to a matrix. The nitric oxide donor is a compound that donates, transfers or releases nitric oxide, elevates endogenous levels of endothelium-derived relaxing factor, stimulates endogenous synthesis of nitric oxide or is a substrate for nitric oxide synthase and may preferably be isosorbide dinitrate and/or isosorbide mononitrate. The antioxidant may preferably be a hydralazine compound or a pharmaceutically acceptable salt thereof. The invention also provides methods for treating and/or preventing vascular diseases characterized by nitric oxide insufficiency; and for treating and/or preventing Raynaud's syndrome; and for treating and/or preventing cardiovascular diseases or disorders.

BACKGROUND OF THE INVENTION

The decline in cardiovascular morbidity and mortality in the United States over the past three decades has been the result of significant advances in research on cardiovascular disease mechanisms and therapeutic strategies. The incidence and prevalence of myocardial infarction and death from myocardial infarction, as well as that from cerebrovascular accident, have decreased significantly over this period largely owing to advances in prevention, early diagnosis, and treatment of these very common diseases.

Analysis of outcomes by race, however, paints quite a different picture: life expectancy and cardiovascular morbidity rates have improved far less for blacks than whites. Available data show that the likelihood of dying from cardiovascular disease is far greater among black Americans than among white Americans. In this decade, the death rate from cardiovascular disease for black males was 353 per 100,000 population, while that for white males was 244 per 100,000; the rate for black females was 226 per 100,000; while that for white females was 135 per 100,000. Consonant with this important demographic parameter is the observation that there is a higher prevalence of several of the important risk factors for cardiovascular disease, e.g., hypertension, smoking, diabetes mellitus, obesity, and left ventricular hypertrophy, among blacks compared with whites. In addition, outcomes of cardiovascular events are worse for blacks than whites. Following myocardial infarction, blacks have a 50% higher annual mortality rate than whites, and their five-year survival is only 70%. Thus, the many advances in cardiovascular medicine that account for the overall improvement in cardiovascular health in the general population has failed to translate into comparable racial benefits.

There is a need in the art for new and more effective compositions and methods for treating vascular diseases. The invention is directed to these, as well as other, important ends.

SUMMARY OF THE INVENTION

The invention describes novel nitrosated and/or nitrosylated nebivolol, novel nitrosated and/or nitrosylated metabolites of nebivolol and methods of treating and/or preventing vascular diseases characterized by nitric oxide insufficiency, and Raynaud's syndrome by administering at least one nitrosated and/or nitrosylated nebivolol and/or at least one nitrosated and/or nitrosylated metabolite of nebivolol that is capable of releasing a therapeutically effective amount of nitric oxide to a targeted site effected by the vascular disease.

One embodiment of the invention provides novel nitrosated and/or nitrosylated nebivolol and/or novel nitrosated and/or nitrosylated metabolites of nebivolol. The nebivolol and/or its metabolites can be nitrosated and/or nitrosylated through one or more sites such as oxygen (hydroxyl condensation), sulfur (sulfhydryl condensation) and/or nitrogen. The invention also provides compositions comprising a therapeutically effective amount of such compounds in a pharmaceutically acceptable carrier.

Another embodiment of the invention provides compositions comprising a therapeutically effective amount of nebivolol that is optionally substituted with at least one NO and/or $NO_2$ group (i.e., nitrosylated and/or nitrosated), and/or at least one metabolite of nebivolol, that is optionally substituted with at least one NO and/or $NO_2$ group (i.e., nitrosylated and/or nitrosated), and at least one compound that donates, transfers or releases nitrogen monoxide as a charged species, i.e., nitrosonium ($NO^+$) or nitroxyl (NO−), or as the neutral species, nitric oxide (NO•), and/or stimulates endogenous production of nitric oxide or EDRF in vivo and/or is a substrate for nitric oxide synthase. The nitric oxide donor may preferably be isosorbide dinitrate and/or isosorbide mononitrate. The invention also provides for such compositions in a pharmaceutically acceptable carrier.

Yet another embodiment of the invention provides compositions comprising a therapeutically effective of nebivolol that is optionally substituted with at least one NO and/or $NO_2$ group (i.e., nitrosylated and/or nitrosated), and/or at least one metabolite of nebivolol, that is optionally substituted with at least one NO and/or $NO_2$ group (i.e., nitrosylated and/or nitrosated), and at least one antioxidant, and, optionally, at least one compound that donates, transfers or releases nitrogen monoxide as a charged species, i.e., nitrosonium ($NO^+$) or nitroxyl (NO−), or as the neutral species, nitric oxide (NO•), and/or stimulates endogenous production of nitric oxide or EDRF in vivo and/or is a substrate for nitric oxide synthase. The antioxidant may preferably be a hydralazine compound or a pharmaceutically acceptable salt thereof. The nitric oxide donor may preferably be isosorbide dinitrate and/or isosorbide mononitrate. The invention also provides for such compositions in a pharmaceutically acceptable carrier.

Another embodiment of the invention provides compositions comprising a therapeutically effective amount of nebivolol that is optionally substituted with at least one NO and/or $NO_2$ group (i.e., nitrosylated and/or nitrosated), and/or at least one metabolite of nebivolol, that is optionally substituted with at least one NO and/or $NO_2$ group (i.e., nitrosylated and/or nitrosated), and, optionally, at least one antioxidant, and/or at least one compound that donates, transfers or releases nitrogen monoxide as a charged species, i.e., nitrosonium ($NO^+$) or nitroxyl (NO−), or as the neutral species, nitric oxide (NO•), and/or stimulates endogenous production of nitric oxide or EDRF in vivo and/or is a substrate for nitric oxide synthase and/or at least one compound used to treat cardiovascular diseases, optionally substituted with at least one $NO_2$ group (i.e., nitrosated). The antioxidant may preferably be a hydralazine compound or a pharmaceutically acceptable salt thereof. The nitric oxide donor may preferably be isosorbide dinitrate and/or isosorbide mononitrate. The invention also provides for such compositions in a pharmaceutically acceptable carrier.

The invention provides methods for treating and/or preventing vascular diseases characterized by nitric oxide insufficiency by administering to a patient a therapeutically effective amount of nebivolol that is optionally substituted with at least one NO and/or $NO_2$ group (i.e., nitrosylated and/or nitrosated), and/or at least one metabolite of nebivolol, that is optionally substituted with at least one NO and/or $NO_2$ group (i.e. nitrosylated and/or nitrosated), and, optionally, at least one compound that donates, transfers or releases nitric oxide, elevates endogenous levels of endothelium-derived relaxing factor, stimulates endogenous synthesis of nitric oxide or is a substrate for nitric oxide synthase, and/or at least one antioxidant or a pharmaceutically acceptable salt thereof, and/or at least one compound used to treat cardiovascular diseases, or a pharmaceutically acceptable salt thereof, optionally substituted with at least one $NO_2$ group (i.e., nitrosated). The nitric oxide donor may preferably be isosorbide dinitrate and/or isosorbide mononitrate. The antioxidant may preferably be a hydralazine compound or a pharmaceutically acceptable salt thereof. The nebivolol and/or the metabolite of nebivolol and optional nitric oxide donor compound, antioxidant, and/or compound used to treat cardiovascular diseases can be administered separately or as components of the same composition in one or more pharmaceutically acceptable carriers.

In another embodiment, the invention provides methods for treating and/or preventing Raynaud's syndrome by administering to a patient a therapeutically effective amount of nebivolol that is optionally substituted with at least one NO and/or $NO_2$ group (i.e., nitrosylated and/or nitrosated), and/or at least one metabolite of nebivolol, that is optionally substituted with at least one NO and/or $NO_2$ group (i.e., nitrosylated and/or nitrosated), and, optionally, at least one compound that donates, transfers or releases nitric oxide, elevates endogenous levels of endothelium-derived relaxing factor, stimulates endogenous synthesis of nitric oxide or is a substrate for nitric oxide synthase, and/or at least one antioxidant or a pharmaceutically acceptable salt thereof, and/or at least one compound used to treat cardiovascular diseases that is optionally substituted with at least one $NO_2$ group (i.e., nitrosated). The nitric oxide donor may preferably be isosorbide dinitrate and/or isosorbide mononitrate. The antioxidant may preferably be a hydralazine compound or a pharmaceutically acceptable salt thereof. The nebivolol and/or metabolite of nebivolol and optional nitric oxide donor compound, antioxidant, and/or compound used to treat cardiovascular diseases can be administered separately or as components of the same composition in one or more pharmaceutically acceptable carriers.

Another embodiment of the invention describes compositions and methods for making compositions comprising nebivolol that is optionally substituted with at least one NO and/or $NO_2$ group (i.e., nitrosylated and/or nitrosated), and/or at least one metabolite of nebivolol, that is optionally substituted with at least one NO and/or $NO_2$ group (i.e., nitrosylated and/or nitrosated), and, optionally, at least one compound that donates, transfers or releases nitric oxide and/or stimulates endogenous production of nitric oxide or EDRF in vivo and/or is a substrate for nitric oxide synthase, that are bound to a natural or synthetic matrix, which can be applied with specificity to a biological site of interest. For example, the matrix containing the nitrosated and/or nitrosylated nebivolol can be used to coat the surface of a medical device or instrument that comes into contact with blood (including blood components, blood products and the like) or vascular tissue.

Another embodiment of the invention also provides methods for administering to a patient in need thereof a therapeutically effective amount of nebivolol and/or at least one metabolite of nebivolol and at least one compound that donates, transfers or releases nitric oxide as a charged species, i.e., nitrosonium ($NO^+$) or nitroxyl (NO−), or as the neutral species, nitric oxide (NO•), and/or stimulates endogenous production of nitric oxide or EDRF in vivo and/or is a substrate for nitric oxide synthase for treating and/or preventing cardiovascular diseases or disorders. The methods can further comprise administering a therapeutically effective amount of at least one therapeutic agent. Alternatively, the methods for treating and/or preventing cardiovascular diseases or disorders, can comprise administering a therapeutically effective amount of at nebivolol and/or at least one metabolite of nebivolol, at least one therapeutic agent, and, optionally, at least one compound that donates, transfers or releases nitric oxide as a charged species, i.e., nitrosonium ($NO^+$) or nitroxyl (NO−), or as the neutral species, nitric oxide (NO•), and/or stimulates endogenous production of nitric oxide or EDRF in vivo and/or is a substrate for nitric oxide synthase. The nebivolol, the metabolite of nebivolol, the nitric oxide donors, and the therapeutic agents can be administered separately or as components of the same composition in one or more pharmaceutically acceptable carriers.

Yet another embodiment of the invention describes methods for the prevention of platelet aggregation and platelet adhesion caused by the exposure of blood to a medical device or instrument by incorporating at least one nitrosated and/or nitrosylated nebivolol and/or at least one metabolite of nebivolol that is capable of releasing a therapeutically effective amount of nitric oxide into and/or on the portion(s) of the medical device that come into contact with blood (including blood components and blood products) or vascular tissue. The methods can further comprise incorporating at least one compound that donates, transfers or releases nitric oxide, and/or stimulates endogenous production of nitric oxide or EDRF in vivo and/or is a substrate for nitric oxide synthase, and, optionally, at least one therapeutic agent into and/or on the portion(s) of the medical device that come into contact with blood or vascular tissue. Alternatively the methods can comprise incorporating nebivolol and/or at least one metabolite of nebivolol and at least one NO donor, and, optionally, at least one therapeutic agent into and/or on the portion(s) of the medical device that comes into contact with blood or vascular tissue.

Another embodiment of the invention relates to the local administration of nebivolol that is optionally substituted with at least one NO and/or $NO_2$ group, and/or at least one metabolite of nebivolol, that is optionally substituted with at least one NO and/or $NO_2$ group, and, optionally, at least one therapeutic agent and/or at least one nitric oxide donor, to treat injured tissue, such as damaged blood vessels.

These and other aspects of the invention are described in detail herein. The following drawings are illustrative of embodiments of the invention and do not limit the scope of the invention as defined by the claims.

DETAILED DESCRIPTION OF THE INVENTION

Figure 1:
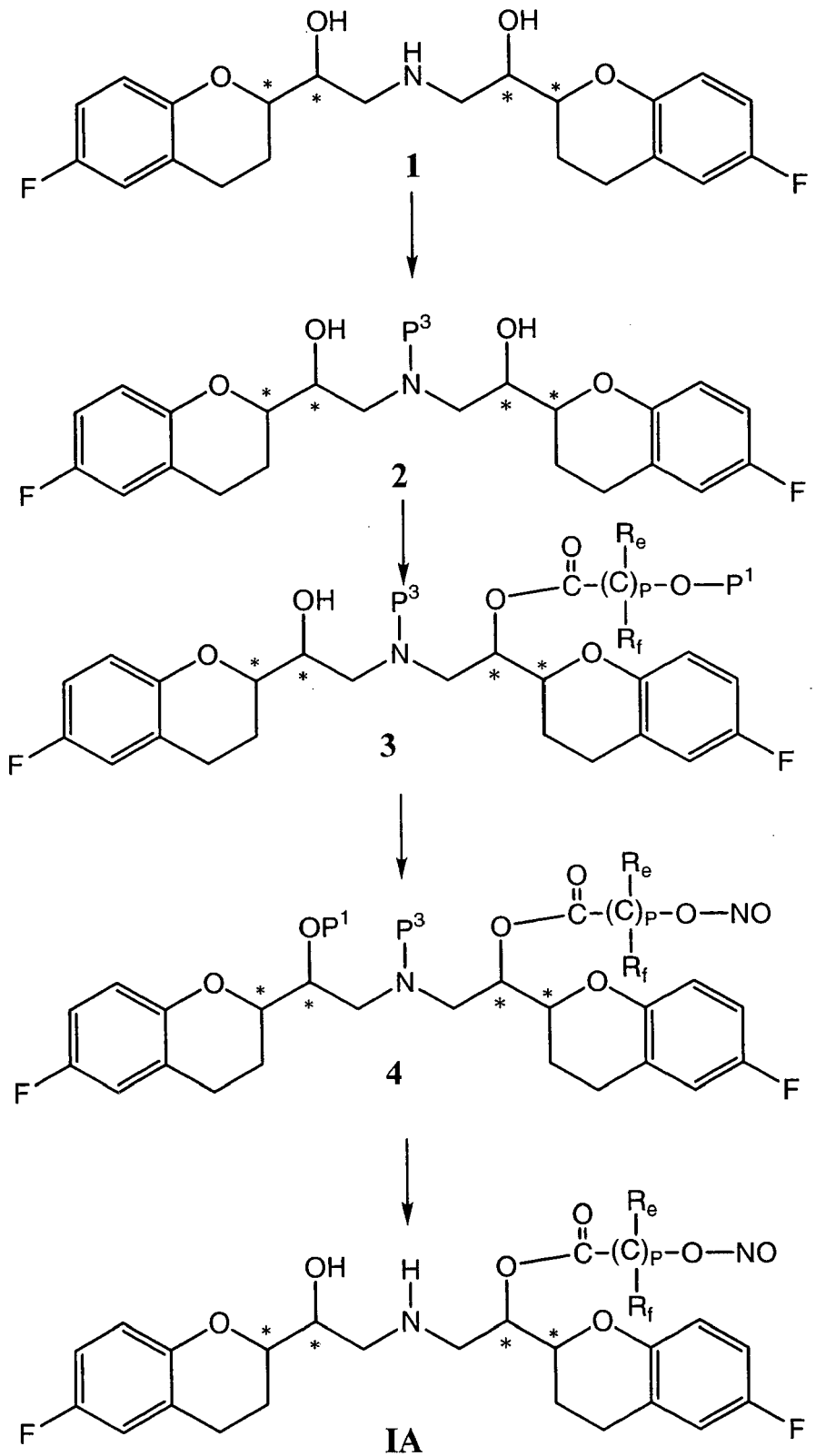
FIG. 1 is the synthetic scheme for the preparation of nitrite containing compounds of Formula (I).

As used throughout the disclosure, the following terms, unless otherwise indicated, shall be understood to have the following meanings.

"Patient" refers to animals, preferably mammals, most preferably humans, and includes males and females.

"Therapeutically effective amount" refers to the amount of the compound and/or composition that is effective to achieve its intended purpose.

"Hydrazino" refers to $H_2N$—$N(H)$—.

"Hydralazine compound" refers to a compound having the Formula (VI):

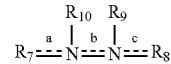

VI wherein a, b and c are independently a single or double bond; $R_7$ and $R_8$ are each independently a hydrogen, an alkyl, an ester or a heterocyclic ring; $R_9$ and $R_{10}$ are each independently a lone pair of electrons or a hydrogen, with the proviso that at least one of $R_7$, $R_8$, $R_9$ and $R_{10}$ is not a hydrogen. Exemplary hydralazine compounds include budralazine, cadralazine, dihydralazine, endralazine, hydralazine, pildralazine, todralazine, and the like.

"Compound used to treat cardiovascular diseases" refers to any therapeutic compound, or a pharmaceutically acceptable salt thereof, used to treat any cardiovascular disease.

"Vascular diseases characterized by nitric oxide insufficiency" include, but are not limited to, cardiovascular diseases; diseases resulting from oxidative stress; hypertension (e.g., low-renin hypertension; salt-sensitive hypertension; low-renin, salt-sensitive hypertension; primary pulmonary hypertension; thromboembolic pulmonary hypertension; pregnancy-induced hypertension; renovascular hypertension, hypertension-dependent end-stage renal disease), heart failure (e.g., microvascular cardiac ischemia), and left ventricular hypertrophy with disproportionate microvascularization, (i.e., inadequate vascularity) or diastolic dysfunction.

"Cardiovascular diseases" refers to any cardiovascular disease or disorder known in the art, including, but not limited to, congestive heart failure, hypertension, pulmonary hypertension, myocardial and cerebral infarctions, atherosclerosis, atherogenesis, thrombosis, ischemic heart disease, post-angioplasty restenosis, coronary artery diseases, renal failure, stable, unstable and variant (Prinzmetal) angina, cardiac edema, renal insufficiency, nephrotic edema, hepatic edema, stroke, transient ischemic attacks, cerebrovascular accidents, restenosis, controlling blood pressure in hypertension (especially hypertension associated with cardiovascular surgical procedures), platelet adhesion, platelet aggregation, smooth muscle cell proliferation, pulmonary edema associated with acute myocardial infarction, vascular complications associated with the use of medical devices, wounds associated with the use of medical devices, pulmonary thromboembolism, cerebral thromboembolism, thrombophlebitis, thrombocytopenia, bleeding disorders, and the like. Complications associated with the use of medical devices may occur as a result of increased platelet deposition, activation, thrombus formation or consumption of platelets and coagulation proteins. Such complications, which are within the definition of "cardiovascular disease or disorder," include, for example, myocardial infarction, pulmonary thromboembolism, cerebral thromboembolism, thrombophlebitis, thrombocytopenia, bleeding disorders and/or any other complications which occur either directly or indirectly as result of the foregoing disorders.

"Restenosis" is a cardiovascular disease or disorder that refers to the closure of a peripheral or coronary artery following trauma to the artery caused by an injury such as, for example, angioplasty, balloon dilation, atherectomy, laser ablation treatment or stent insertion. For these angioplasty procedures, restenosis occurs at a rate of about 30–60% depending upon the vessel location, lesion length and a number of other variables. Restenosis can also occur following a number of invasive surgical techniques, such as, for example, transplant surgery, vein grafting, coronary artery bypass surgery, endarterectomy, heart transplantation, ballon angioplasty, atherectomy, laser ablation, endovascular stenting, and the like.

"Atherosclerosis" is a form of chronic vascular injury in which some of the normal vascular smooth muscle cells in the artery wall, which ordinarily control vascular tone regulating blood flow, change their nature and develop "cancer-like" behavior. These vascular smooth muscle cells become abnormally proliferative, secreting substances such as growth factors, tissue-degradation enzymes and other proteins, which enable them to invade and spread into the inner vessel lining, blocking blood flow and making that vessel abnormally susceptible to being completely blocked by local blood clotting, resulting in the death of the tissue served by that artery.

"Diseases resulting from oxidative stress" refers to any disease that involves the generation of free radicals or radical compounds, such as, for example, atherogenesis, atheromatosis, arteriosclerosis, artherosclerosis, vascular hypertrophy associated with hypertension, hyperlipoproteinaemia, normal vascular degeneration through aging, parathyroidal reactive hyperplasia, chronic renal disease, neoplastic diseases, inflammatory diseases, neurological and acute bronchopulmonary disease, tumorigenesis, ischemia-reperfusion syndrome, arthritis, sepsis, and the like.

"Therapeutic agent" includes any therapeutic agent that can inhibit the cellular activity of a vascular smooth muscle cell, for example, proliferation, migration, increase in cell volume, increase in extracellular matrix synthesis (e.g., collagens, proteoglycans, and the like), or secretion of extracellular matrix materials by the cell, biologically stenting a vessel and/or reduce or inhibit vascular remodeling and/or inhibit or reduce vascular smooth muscle proliferation following a procedural vascular trauma. Although nitric oxide donors have therapeutic activity, the term "therapeutic agent" does not include the nitric oxide donors described herein, since nitric oxide donors are separately defined.

"Artificial surface" refers to any natural or synthetic material contained in a device or apparatus that is in contact with blood, vasculature or other tissues.

"Blood" includes blood products, blood components and the like.

"Platelet adhesion" refers to the contact of a platelet with a foreign surface, including any artificial surface, such as a medical device or instrument, as well as an injured vascular surfaces, such as collagen. Platelet adhesion does not require platelet activation. Unactivated, circulating platelets will adhere to injured vascular surfaces or artificial surfaces via binding interactions between circulating von Willdebrand factor and platelet surface glycoprotein Ib/IX.

"Platelet aggregation" refers to the binding of one or more platelets to each other. Platelet aggregation is commonly referred to in the context of generalized atherosclerosis, not with respect to platelet adhesion on vasculature damaged as a result of physical injury during a medical procedure. Platelet aggregation requires platelet activation, which depends on the interaction between the ligand and its specific platelet surface receptor.

"Platelet activation" refers either to the change in conformation (shape) of a cell, expression of cell surface proteins (e.g., the IIb/IIIa receptor complex, loss of GPIb surface protein), and secretion of platelet derived factors (e.g., serotonin, growth factors).

"Passivation" refers to the coating of a surface, which renders the surface non-reactive.

"Medical device" refers to any intravascular or extravascular medical devices, medical instruments, foreign bodies and the like. Examples of intravascular medical devices and instruments include balloons or catheter tips adapted for insertion, prosthetic heart valves, sutures, synthetic vessel grafts, stents (e.g. Palmaz-Schatz stent), drug pumps, arteriovenous shunts, artificial heart valves, artificial implants, foreign bodies introduced surgically into the blood vessels or at vascular sites, leads, pacemakers, implantable pulse generators, implantable cardiac defibrillators, cardioverter defibrillators, defibrillators, spinal stimulators, brain stimulators, sacral nerve stimulators, chemical sensors, and the like. Examples of extravascular medical devices and instruments include plastic tubing, dialysis bags or membranes whose surfaces come in contact with the blood stream of a patient.

"Transdermal" refers to the delivery of a compound by passage through the skin and into the blood stream.

"Transmucosal" refers to delivery of a compound by passage of the compound through the mucosal tissue and into the blood stream.

"Penetration enhancement" or "permeation enhancement" refers to an increase in the permeability of the skin or mucosal tissue to a selected pharmacologically active compound such that the rate at which the compound permeates through the skin or mucosal tissue is increased.

"Carriers" or "vehicles" refers to carrier materials suitable for compound administration and include any such material known in the art such as, for example, any liquid, gel, solvent, liquid diluent, solubilizer, or the like, which is non-toxic and which does not interact with any components of the composition in a deleterious manner.

"Sustained release" refers to the release of a therapeutically active compound and/or composition such that the blood levels of the therapeutically active compound are maintained within a desirable therapeutic range over an extended period of time. The sustained release formulation can be prepared using any conventional method known to one skilled in the art to obtain the desired release characteristics.

"Nitric oxide adduct" or "NO adduct" refers to compounds and functional groups which, under physiological conditions, can donate, release and/or directly or indirectly transfer any of the three redox forms of nitrogen monoxide ($NO^+$, $NO^-$, $NO\bullet$), such that the biological activity of the nitrogen monoxide species is expressed at the intended site of action.

"Nitric oxide releasing" or "nitric oxide donating" refers to methods of donating, releasing and/or directly or indirectly transferring any of the three redox forms of nitrogen monoxide ($NO^+$, $NO-$, $NO\bullet$), such that the biological activity of the nitrogen monoxide species is expressed at the intended site of action.

"Nitric oxide donor" or "NO donor" refers to compounds that donate, release and/or directly or indirectly transfer a nitrogen monoxide species, and/or stimulate the endogenous production of nitric oxide or endothelium-derived relaxing factor (EDRF) in vivo and/or elevate endogenous levels of nitric oxide or EDRF in vivo. "NO donor" also includes compounds that are substrates for nitric oxide synthase.

"Taxane" refers to any compound that contains the carbon core framework represented by Formula A:

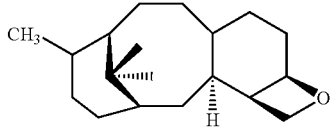

A

"Alkyl" refers to a lower alkyl group, a haloalkyl group, a hydroxyalkyl group, an alkenyl group, an alkynyl group, a bridged cycloalkyl group, a cycloalkyl group or a heterocyclic ring, as defined herein. An alkyl group may also comprise one or more radical species, such as, for example a cycloalkylalkyl group or a heterocyclicalkyl group.

"Lower alkyl" refers to branched or straight chain acyclic alkyl group comprising one to about ten carbon atoms (preferably one to about eight carbon atoms, more preferably one to about six carbon atoms). Exemplary lower alkyl groups include methyl, ethyl, n-propyl, isopropyl, n-butyl, isobutyl, sec-butyl, t-butyl, pentyl, neopentyl, iso-amyl, hexyl, octyl, and the like.

"Substituted lower alkyl" refers to a lower alkyl group, as defined herein, wherein one or more of the hydrogen atoms have been replaced with one or more $R^{100}$ groups, wherein each $R^{100}$ is independently a hydroxy, an oxo, a carboxyl, a carboxamido, a halo, a cyano or an amino group, as defined herein.

"Haloalkyl" refers to a lower alkyl group, an alkenyl group, an alkynyl group, a bridged cycloalkyl group, a cycloalkyl group or a heterocyclic ring, as defined herein, to which is appended one or more halogens, as defined herein. Exemplary haloalkyl groups include trifluoromethyl, chloromethyl, 2-bromobutyl, 1-bromo-2-chloro-pentyl, and the like.

"Alkenyl" refers to a branched or straight chain $C_2$–$C_{10}$ hydrocarbon (preferably a $C_2$–$C_8$ hydrocarbon, more preferably a $C_2$–$C_6$ hydrocarbon) that can comprise one or more carbon-carbon double bonds. Exemplary alkenyl groups include propylenyl, buten-1-yl, isobutenyl, penten-1-yl, 2,2-methylbuten-1-yl, 3-methylbuten-1-yl, hexan-1-yl, hepten-1-yl, octen-1-yl, and the like.

"Lower alkenyl" refers to a branched or straight chain $C_2$–$C_4$ hydrocarbon that can comprise one or two carbon-carbon double bonds.

"Substituted alkenyl" refers to a branched or straight chain $C_2$–$C_{10}$ hydrocarbon (preferably a $C_2$–$C_8$ hydrocarbon, more preferably a $C_2$–$C_6$ hydrocarbon) which can comprise one or more carbon-carbon double bonds, wherein one or more of the hydrogen atoms have been replaced with one or more $R^{100}$ groups, wherein each $R^{100}$ is independently a hydroxy, an oxo, a carboxyl, a carboxamido, a halo, a cyano or an amino group, as defined herein.

"Alkynyl" refers to an unsaturated acyclic $C_2$–$C_{10}$ hydrocarbon (preferably a $C_2$–$C_8$ hydrocarbon, more preferably a $C_2$–$C_6$ hydrocarbon) that can comprise one or more carbon-carbon triple bonds. Exemplary alkynyl groups include ethynyl, propynyl, butyn-1-yl, butyn-2-yl, pentyl-1-yl, pentyl-2-yl, 3-methylbutyn-1-yl, hexyl-1-yl, hexyl-2-yl, hexyl-3-yl, 3,3-dimethyl-butyn-1-yl, and the like.

"Bridged cycloalkyl" refers to two or more saturated or unsaturated cycloalkyl groups, saturated or unsaturated heterocyclic groups, or a combination thereof fused via adjacent or non-adjacent atoms. Bridged cycloalkyl groups can be unsubstituted or substituted with one, two or three substituents independently selected from alkyl, alkoxy, amino, alkylamino, dialkylamino, hydroxy, halo, carboxyl, alkylcarboxylic acid, aryl, amidyl, ester, alkylcarboxylic ester, carboxamido, alkylcarboxamido, oxo and nitro. Exemplary bridged cycloalkyl groups include adamantyl, decahydronapthyl, quinuclidyl, 2,6-dioxabicyclo(3.3.0)octane, 7-oxabycyclo(2.2.1)heptyl, 8-azabicyclo(3,2,1)oct-2-enyl and the like.

"Cycloalkyl" refers to a saturated or unsaturated cyclic hydrocarbon comprising from about 3 to about 10 carbon atoms. Cycloalkyl groups can be unsubstituted or substituted with one, two or three substituents independently selected from alkyl, alkoxy, amino, alkylamino, dialkylamino, arylamino, diarylamino, alkylarylamino, aryl, amidyl, ester, hydroxy, halo, carboxyl, alkylcarboxylic acid, alkylcarboxylic ester, carboxamido, alkylcarboxamido, oxo, alkylsulfinyl, and nitro. Exemplary cycloalkyl groups include cyclopropyl, cyclobutyl, cyclopentyl, cyclohexyl, cyclohexenyl, cyclohepta-1,3-dienyl, and the like.

"Heterocyclic ring or group" refers to a saturated or unsaturated cyclic hydrocarbon group having about 2 to about 10 carbon atoms (preferably about 4 to about 6 carbon atoms) where 1 to about 4 carbon atoms are replaced by one or more nitrogen, oxygen and/or sulfur atoms. Sulfur maybe in the thio, sulfinyl or sulfonyl oxidation state. The heterocyclic ring or group can be fused to an aromatic hydrocarbon group. Heterocyclic groups can be unsubstituted or substituted with one, two or three substituents independently selected from alkyl, alkoxy, amino, alkylthio, aryloxy, arylthio, arylalkyl, hydroxy, oxo, thial, halo, carboxyl, carboxylic ester, alkylcarboxylic acid, alkylcarboxylic ester, aryl, arylcarboxylic acid, arylcarboxylic ester, amidyl, ester, alkylcarbonyl, arylcarbonyl, alkylsulfinyl, carboxamido, alkylcarboxamido, arylcarboxamido, sulfonic acid, sulfonic ester, sulfonamido and nitro. Exemplary heterocyclic groups include pyrrolyl, furyl, thienyl, 3-pyrrolinyl,4,5,6-trihydro-2H-pyranyl, pyridinyl, 1,4-dihydropyridinyl, pyrazolyl, triazolyl, pyrimidinyl, pyridazinyl, oxazolyl, thiazolyl, imidazolyl, indolyl, thiophenyl, furanyl, tetrhydrofuranyl, tetrazolyl, pyrrolinyl, pyrrolindinyl, oxazolindinyl 1,3-dioxolanyl, imidazolinyl, imidazolindinyl, pyrazolinyl, pyrazolidinyl, isoxazolyl, isothiazolyl, 1,2,3-oxadiazolyl, 1,2,3-triazolyl, 1,3,4-thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, 1,3,5-triazinyl, 1,3,5-trithianyl, benzo(b)thiophenyl, benzimidazolyl, benzothiazolinyl, quinolinyl, and the like.

"Heterocyclic compounds" refer to mono- and polycyclic compounds comprising at least one aryl or heterocyclic ring.

"Aryl" refers to a monocyclic, bicyclic, carbocyclic or heterocyclic ring system comprising one or two aromatic rings. Exemplary aryl groups include phenyl, pyridyl, napthyl, quinoyl, tetrahydronaphthyl, furanyl, indanyl, indenyl, indoyl, and the like. Aryl groups (including bicyclic aryl groups) can be unsubstituted or substituted with one, two or three substituents independently selected from alkyl, alkoxy, alkylthio, amino, alkylamino, dialkylamino, arylamino, diarylamino, alkylarylamino, halo, cyano, alkylsulfinyl, hydroxy, carboxyl, carboxylic ester, alkylcarboxylic acid, alkylcarboxylic ester, aryl, arylcarboxylic acid, arylcarboxylic ester, alkylcarbonyl, arylcarbonyl, amidyl, ester, carboxamido, alkylcarboxamido, carbomyl, sulfonic acid, sulfonic ester, sulfonamido and nitro. Exemplary substituted aryl groups include tetrafluorophenyl, pentafluorophenyl, sulfonamide, alkylsulfonyl, arylsulfonyl, and the like.

"Cycloalkenyl" refers to an unsaturated cyclic $C_2$–$C_{10}$ hydrocarbon (preferably a $C_2$–$C_8$ hydrocarbon, more preferably a $C_2$–$C_6$ hydrocarbon) which can comprise one or more carbon-carbon triple bonds.

"Arylalkyl" refers to an aryl radical, as defined herein, attached to an alkyl radical, as defined herein. Exemplary arylalkyl groups include benzyl, phenylethyl, 4-hydroxybenzyl, 3-fluorobenzyl, 2-fluorophenylethyl, and the like.

"Alkylaryl" refers to an alkyl group, as defined herein, to which is appended an aryl group, as defined herein. Exemplary alkylaryl groups include benzyl, phenylethyl, hydroxybenzyl, fluorobenzyl, fluorophenylethyl, and the like.

"Arylalkenyl" refers to an aryl radical, as defined herein, attached to an alkenyl radical, as defined herein. Exemplary arylalkenyl groups include styryl, propenylphenyl, and the like.

"Cycloalkylalkyl" refers to a cycloalkyl radical, as defined herein, attached to an alkyl radical, as defined herein.

"Cycloalkylalkoxy" refers to a cycloalkyl radical, as defined herein, attached to an alkoxy radical, as defined herein.

"Cycloalkylalkylthio" refers to a cycloalkyl radical, as defined herein, attached to an alkylthio radical, as defined herein.

"Heterocyclicalkyl" refers to a heterocyclic ring radical, as defined herein, attached to an alkyl radical, as defined herein.

"Arylheterocyclic ring" refers to a bi- or tricyclic ring comprised of an aryl ring, as defined herein, appended via two adjacent carbon atoms of the aryl ring to a heterocyclic ring, as defined herein. Exemplary arylheterocyclic rings include dihydroindole, 1,2,3,4-tetra-hydroquinoline, and the like.

"Alkoxy" refers to $R_{50}O$—, wherein $R_{50}$ is an alkyl group, as defined herein (preferably a lower alkyl group or a haloalkyl group, as defined herein). Exemplary alkoxy groups include methoxy, ethoxy, t-butoxy, cyclopentyloxy, trifluoromethoxy, and the like.

"Lower alkoxy" refers to a lower alkyl group, as defined herein, appended to an oxygen atom.

"Aryloxy" refers to $R_{55}O$—, wherein $R_{55}$ is an aryl group, as defined herein. Exemplary arylkoxy groups include napthyloxy, quinolyloxy, isoquinolizinyloxy, and the like.

"Alkylthio" refers to $R_{50}S$—, wherein $R_{50}$ is an alkyl group, as defined herein.

"Lower alkylthio" refers to a lower alkyl group, as defined herein, appended to a thio group, as defined herein.

"Arylalkoxy" or "alkoxyaryl" refers to an alkoxy group, as defined herein, to which is appended an aryl group, as defined herein. Exemplary arylalkoxy groups include benzyloxy, phenylethoxy, chlorophenylethoxy, and the like.

"Alkoxyalkyl" refers to an alkoxy group, as defined herein, appended to an alkyl group, as defined herein. Exemplary alkoxyalkyl groups include methoxymethyl, methoxyethyl, isopropoxymethyl, and the like.

"Alkoxyhaloalkyl" refers to an alkoxy group, as defined herein, appended to a haloalkyl group, as defined herein. Exemplary alkoxyhaloalkyl groups include 4-methoxy-2-chlorobutyl and the like.

"Cycloalkoxy" refers to $R_{54}O$—, wherein $R_{54}$ is a cycloalkyl group or a bridged cycloalkyl group, as defined herein. Exemplary cycloalkoxy groups include cyclopropyloxy, cyclopentyloxy, cyclohexyloxy, and the like.

"Cycloalkylthio" refers to $R_{54}S$—, wherein $R_{54}$ is a cycloalkyl group or a bridged cycloalkyl group, as defined herein. Exemplary cycloalkylthio groups include cyclopropylthio, cyclopentylthio, cyclohexylthio, and the like.

"Haloalkoxy" refers to an alkoxy group, as defined herein, in which one or more of the hydrogen atoms on the alkoxy group are substituted with halogens, as defined herein. Exemplary haloalkoxy groups include 1,1,1-trichloroethoxy, 2-bromobutoxy, and the like.

"Hydroxy" refers to —OH.

"Oxo" refers to =O.

"Oxy" refers to —O$^-$R$_{77}^+$ wherein R$_{77}$ is an organic or inorganic cation.

"Organic cation" refers to a positively charged organic ion. Exemplary organic cations include alkyl substituted ammonium cations, and the like.

"Inorganic cation" refers to a positively charged metal ion. Exemplary inorganic cations include Group I metal cations such as for example, sodium, potassium, and the like.

"Hydroxyalkyl" refers to a hydroxy group, as defined herein, appended to an alkyl group, as defined herein.

"Nitrate" refers to —O—NO$_2$.

"Nitrite" refers to —O—NO.

"Thionitrate" refers to —S—NO$_2$.

"Thionitrite" and "nitrosothiol" refer to —S—NO.

"Nitro" refers to the group —NO$_2$ and "nitrosated" refers to compounds that have been substituted therewith.

"Nitroso" refers to the group —NO and "nitrosylated" refers to compounds that have been substituted therewith.

"Nitrile" and "cyano" refer to —CN.

"Halogen" or "halo" refers to iodine (I), bromine (Br), chlorine (Cl), and/or fluorine (F).

"Amino" refers to —NH$_2$, an alkylamino group, a dialkylamino group, an arylamino group, a diarylamino group, an alkylarylamino group or a heterocyclic ring, as defined herein.

"Alkylamino" refers to $R_{50}NH$—, wherein $R_{50}$ is an alkyl group, as defined herein. Exemplary alkylamino groups include methylamino, ethylamino, butylamino, cyclohexylamino, and the like.

"Arylamino" refers to $R_{55}NH$—, wherein $R_{55}$ is an aryl group, as defined herein.

"Dialkylamino" refers to $R_{52}R_{53}N$—, wherein $R_{52}$ and $R_{53}$ are each independently an alkyl group, as defined herein. Exemplary dialkylamino groups include dimethylamino, diethylamino, methyl propargylamino, and the like.

"Diarylamino" refers to $R_{55}R_{60}N$—, wherein $R_{55}$ and $R_{60}$ are each independently an aryl group, as defined herein.

"Alkylarylamino or arylalkylamino" refers to $R_{52}R_{55}N$—, wherein $R_{52}$ is an alkyl group, as defined herein, and $R_{55}$ is an aryl group, as defined herein.

"Alkylarylalkylamino" refers to $R_{52}R_{79}N$—, wherein $R_{52}$ is an alkyl group, as defined herein, and $R_{79}$ is an arylalkyl group, as defined herein.

"Alkylcycloalkylamino" refers to $R_{52}R_{80}N$—, wherein $R_{52}$ is an alkyl group, as defined herein, and $R_{80}$ is an cycloalkyl group, as defined herein.

"Aminoalkyl" refers to an amino group, an alkylamino group, a dialkylamino group, an arylamino group, a diarylamino group, an alkylarylamino group or a heterocyclic ring, as defined herein, to which is appended an alkyl group, as defined herein. Exemplary aminoalkyl groups include dimethylaminopropyl, diphenylaminocyclopentyl, methylaminomethyl, and the like.

"Aminoaryl" refers to an aryl group to which is appended an alkylamino group, a arylamino group or an arylalkylamino group. Exemplary aminoaryl groups include anilino, N-methylanilino, N-benzylanilino, and the like.

"Thio" refers to —S—.

"Sulfinyl" refers to —S(O)—.

"Methanthial" refers to —C(S)—.

"Thial" refers to =S.

"Sulfonyl" refers to —S(O)$_2^-$.

"Sulfonic acid" refers to —S(O)$_2$OR$_{76}$, wherein R$_{76}$ is a hydrogen, an organic cation or an inorganic cation, as defined herein.

"Alkylsulfonic acid" refers to a sulfonic acid group, as defined herein, appended to an alkyl group, as defined herein.

"Arylsulfonic acid" refers to a sulfonic acid group, as defined herein, appended to an aryl group, as defined herein "Sulfonic ester" refers to —S(O)$_2$OR$_{58}$, wherein R$_{58}$ is an alkyl group, an aryl group, or an aryl heterocyclic ring, as defined herein.

"Sulfonamido" refers to —S(O)$_2$—N(R$_{51}$)(R$_{57}$), wherein R$_{51}$ and R$_{57}$ are each independently a hydrogen atom, an alkyl group, an aryl group or an arylheterocyclic ring, as defined herein, or R$_{51}$ and R$_{57}$ taken together with the nitrogen to which they are attached are a heterocyclic ring or a bridged cycloalkyl group, as defined herein.

"Alkylsulfonamido" refers to a sulfonamido group, as defined herein, appended to an alkyl group, as defined herein.

"Arylsulfonamido" refers to a sulfonamido group, as defined herein, appended to an aryl group, as defined herein.

"Alkylthio" refers to R$_{50}$S—, wherein R$_{50}$ is an alkyl group, as defined herein (preferably a lower alkyl group, as defined herein).

"Arylthio" refers to R$_{55}$S—, wherein R$_{55}$ is an aryl group, as defined herein.

"Arylalkylthio" refers to an aryl group, as defined herein, appended to an alkylthio group, as defined herein.

"Alkylsulfinyl" refers to R$_{50}$—S(O)—, wherein R$_{50}$ is an alkyl group, as defined herein.

"Alkylsulfonyl" refers to R$_{50}$—S(O)$_2$—, wherein R$_{50}$ is an alkyl group, as defined herein.

"Alkylsulfonyloxy" refers to R$_{50}$—S(O)$_2$—O—, wherein R$_{50}$ is an alkyl group, as defined herein.

"Arylsulfinyl" refers to R$_{55}$—S(O)—, wherein R$_{55}$ is an aryl group, as defined herein.

"Arylsulfonyl" refers to R$_{55}$—S(O)$_2$—, wherein R$_{55}$ is an aryl group, as defined herein.

"Arylsulfonyloxy" refers to R$_{55}$—S(O)$_2$—O—, wherein R$_{55}$ is an aryl group, as defined herein.

"Amidyl" refers to R$_{51}$C(O)N(R$_{57}$)— wherein R$_{51}$ and R$_{57}$ are each independently a hydrogen atom, an alkyl group, an aryl group or an arylheterocyclic ring, as defined herein.

"Ester" refers to R$_{51}$C(O)O— wherein R$_{51}$ is a hydrogen atom, an alkyl group, an aryl group or an arylheterocyclic ring, as defined herein.

"Carbamoyl" refers to —O—C(O)N(R$_{51}$)(R$_{57}$), wherein R$_{51}$ and R$_{57}$ are each independently a hydrogen atom, an alkyl group, an aryl group or an arylheterocyclic ring, as defined herein, or R$_{51}$ and R$_{57}$ taken together with the nitrogen to which they are attached are a heterocyclic ring or a bridged cycloalkyl group, as defined herein.

"Carboxyl" refers to —C(O)OR$_{76}$, wherein R$_{76}$ is a hydrogen, an organic cation or an inorganic cation, as defined herein.

"Carbonyl" refers to —C(O)—.

"Alkylcarbonyl" refers to R$_{52}$—C(O)—, wherein R$_{52}$ is an alkyl group, as defined herein.

"Arylcarbonyl" refers to R$_{55}$—C(O)—, wherein R$_{55}$ is an aryl group, as defined herein.

"Arylalkylcarbonyl" refers to R$_{55}$—R$_{52}$—C(O)—, wherein R$_{55}$ is an aryl group, as defined herein, and R$_{52}$ is an alkyl group, as defined herein.

"Alkylarylcarbonyl" refers to R$_{52}$—R$_{55}$—C(O)—, wherein R$_{55}$ is an aryl group, as defined herein, and R$_{52}$ is an alkyl group, as defined herein.

"Heterocyclicalkylcarbonyl" refer to R$_{78}$C(O)— wherein R$_{78}$ is a heterocyclicalkyl group, as defined herein.

"Carboxylic ester" refers to —C(O)OR$_{58}$, wherein R$_{58}$ is an alkyl group, an aryl group or an aryl heterocyclic ring, as defined herein.

"Alkylcarboxylic acid" and "alkylcarboxyl" refer to an alkyl group, as defined herein, appended to a carboxyl group, as defined herein.

"Alkylcarboxylic ester" refers to an alkyl group, as defined herein, appended to a carboxylic ester group, as defined herein.

"Arylcarboxylic acid" refers to an aryl group, as defined herein, appended to a carboxyl group, as defined herein.

"Arylcarboxylic ester" and "arylcarboxyl" refer to an aryl group, as defined herein, appended to a carboxylic ester group, as defined herein.

"Carboxamido" refers to —C(O)N(R$_{51}$)(R$_{57}$), wherein R$_{51}$ and R$_{57}$ are each independently a hydrogen atom, an alkyl group, an aryl group or an arylheterocyclic ring, as defined herein, or R$_{51}$ and R$_{57}$ taken together with the nitrogen to which they are attached are a heterocyclic ring or a bridged cycloalkyl group, as defined herein.

"Alkylcarboxamido" refers to an alkyl group, as defined herein, appended to a carboxamido group, as defined herein.

"Arylcarboxamido" refers to an aryl group, as defined herein, appended to a carboxamido group, as defined herein.

"Oxime" refers to —C(=N—OR$_{81}$) wherein R$_{81}$ is a hydrogen, an alkyl group, an aryl group, an alkylsulfonyl group, an arylsulfonyl group, a carboxylic ester, an alkylcarbonyl group, an arylcarbonyl group, a carboxamido group, an alkoxyalkyl group or an alkoxyaryl group.

"Urea" refers to —N(R$_{59}$)—C(O)N(R$_{51}$)(R$_{57}$) wherein R$_{51}$, R$_{57}$, and R$_{59}$ are each independently a hydrogen atom, an alkyl group, an aryl group or an arylheterocyclic ring, as defined herein, or R$_{51}$ and R$_{57}$ taken together with the nitrogen to which they are attached are a heterocyclic ring or a bridged cycloalkyl group, as defined herein.

"Phosphoryl" refers to —P(R$_{70}$)(R$_{71}$)(R$_{72}$), wherein R$_{70}$ is a lone pair of electrons, sulfur or oxygen, and R$_{71}$ and R$_{72}$ are each independently a covalent bond, a hydrogen, a lower alkyl, an alkoxy, an alkylamino, a hydroxy or an aryl, as defined herein.

"Silyl" refers to —Si(R$_{73}$)(R$_{74}$)(R$_{75}$), wherein R$_{73}$, R$_{74}$ and R$_{75}$ are each independently a covalent bond, a lower alkyl, an alkoxy, an aryl or an arylalkoxy, as defined herein.

Two broad classes of cardiovascular diseases or disorders are more prevalent among blacks than whites and serve as areas in need of investigative efforts. Hypertension and left ventricular hypertrophy, two related yet independent risk factors for coronary heart disease, are significantly more prevalent among blacks than whites. Blacks also have higher rates of angiographically normal coronary arteries despite a higher prevalence of risk factors for coronary atherosclerosis, and greater morbidity and mortality from coronary heart disease than whites. These paradoxical observations have led some investigators to postulate that blacks harbor a diathesis of the microvasculature that limits perfusion and serves as a stimulus for vascular smooth muscle cell and cardiomyocyte hypertrophy, which, in turn, leads to hypertension and left ventricular hypertrophy, respectively. The underlying basis for this vascular diathesis may involve the endothelium, which has a limited capacity to generate vasodilator and antiproliferative factors or an increased capacity to produce vasoconstrictor and proliferative factors; the vascular smooth muscle cell, which manifests increased sensitivity to vasoconstrictor and proliferative factors; or both, in these individuals.

A major product of the normal blood vessel that may play a role in the vascular diathesis of blacks is endothelium-derived nitric oxide (NO). Nitric oxide produced by the endothelial cells induces vascular smooth muscle cell relaxation, contributing importantly to resting vascular tone. In addition, NO inhibits vascular smooth muscle cell proliferation and induces apoptosis in smooth muscle cells, which leads to the release of basic fibroblast growth factor and vascular endothelial cell growth factor, in turn supporting endothelial cell proliferation. This sequence of cellular responses is believed to sustain angiogenesis under hypoxic or ischemic conditions.

The role of nitric oxide in the vascular diathesis of blacks is illustrated by the consequences of nitric oxide insufficiency in the normal responses of the vasculature to nitric oxide. Nitric oxide insufficiency suppresses renin release from the juxtaglomerular cells, and induces a sodium chloride/volume sensitive increase in blood pressure. Furthermore, nitric oxide insufficiency leads to an increased sensitivity of vascular smooth muscle cells to vasoconstrictors, such as angiotensin II and catecholamines, which amplify the increase in vascular resistance.

Nitric oxide insufficiency promotes vascular smooth muscle cell proliferation following vascular injury, and sustains smooth muscle cell and cardiomyocyte hypertrophy in response to catecholamines and angiotensin II. Furthermore, inadequate nitric oxide leads to increased production of extracellular matrix with consequent myocardial fibrosis.

These many cardiovascular responses that result from inadequate NO in the vasculature have clear clinical correlates in the black population. The clinical vascular phenotype of blacks that distinguishes them from whites with similar cardiovascular diseases or disorders is one of salt-sensitive, low-renin hypertension; left ventricular hypertrophy disproportionate to after load and with an inadequate angiogenic response; and microvascular ischemia in the absence of significant epicardial coronary artery disease. The net pathophysiological consequences of these effects are increased peripheral vascular resistance with accompanying arterial hypertension; and an inadequately vascularized, fibrotic increase in left ventricular mass with accompanying diastolic dysfunction and microvascular ischemia.

Nitric oxide insufficiency states can be a consequence of reduced synthesis of nitric oxide, enhanced inactivation of nitric oxide, or both. Possible candidate mechanisms include alterations in the genes that code for endothelial nitric oxide synthase or the inducible microvascular and cardiomyocyte nitric oxide synthase leading to reduced expression of a normal gene product or appropriate expression of a less active gene product; reduction in the enzymatic activity of nitric oxide synthase owing to inadequate cofactor concentrations; or enhanced inactivation of nitric oxide by oxidant stress.

Data obtained by the inventors in cultured cells, animal models, and human patients suggest that increased oxidant stress is central to the vascular diathesis of and consequent cardiovascular diseases or disorders common among African Americans. Possible candidate mechanisms for the oxidant stress include enhanced production of reactive oxygen species (ROS), decreased antioxidant defenses, or both. The inventors make no a priori assumptions about the temporal or causative relationship between oxidant stress and the vascular phenotype of blacks: oxidant stress may both precede the development of the vascular diathesis and promote its progression once established. Recent data suggest that enhanced ROS production accompanies essential hypertension, atherosclerosis, thrombosis, and diabetes mellitus, and appears in each case, at the very least, to be important in the progression of established disease, if not in its actual genesis.

Endothelium-derived relaxing factor (EDRF), first described by Furchgott et al, *Nature*, 299:373–376 (1980), is an important mediator of vascular function. This endothelial product activates guanylyl cyclase in vascular smooth muscle cells and platelets, leading to vasorelaxation and platelet inhibition, respectively (Loscalzo et al, *Prog Cardiovasc Dis*, 38:87–104 (1995)). The chemical nature of EDRF has been studied using a variety of pharmacological and analytical techniques, and is NO (Ignarro et al, *Circ Res*, 61:866–879 (1987); Palmer et al, *Nature*, 327:524–526 (1987)).

Nitric oxide is synthesized by one of several isoforms of the NO synthase (NOS) family of enzymes, two of which are found in the vasculature, endothelial NOS (eNOS) and inducible NOS (iNOS). eNOS is synthesized by endothelial cells, while iNOS is synthesized by a variety of cell types, including vascular smooth muscle cells, fibroblasts, and (principally microvascular) endothelial cells (Balligand et al, *Am J Physiol*, 268:H1293–1303 (1995)). These enzymes produce NO as a result of the five-electron oxidation of L-arginine to L-citrulline; requisite cofactors include calcium-calmodulin, $O_2$, FAD, FMN, tetrahydrobiopterin thiols, heme, and NADPH. (Moncada et al, *N Engl J Med*, 329:2002–2012 (1993)).

The role of NO in the cardiovascular system has become increasingly apparent over the past fifteen years (Loscalzo et al, *Prog Cardiovasc Dis*, 38:87–104 (1995)). Nitric oxide contributes importantly to resting tone in conductance as well as resistance arteries (Ouyyumi et al, *J Clin Invest*, 95:1747–1755 (1995)), and plays a critical role in the maintenance of peripheral vascular resistance and arterial pressure responses. Inhibition of NOS activity is associated with enhanced vascular sensitivity to vasoconstrictors, such as norepinephrine and angiotensin II (Conrad et al, *Am J Physiol*, 262:R1137–R1144 (1992)), and this effect appears to be mediated, in part, by increased calcium sensitivity (Bank et al, *Hypertension*, 24:322–328 (1994)). Nitric oxide release from the cardiovascular regulatory center in the brain may also be involved in the central regulation of blood pressure, suggesting a role for neuronal NOS in the regulation of vascular tone (Cabrera et al, *Biochem Biophys Res Comm*, 206:77–81 (1995); Mattson et al, *Hypertension*, 28:297–303 (1996)).

Nitric oxide activates renin gene expression in the kidney, and is involved in the baroreceptor-mediated regulation of renin gene expression (Schricker et al, *Pflug Arch*, 428: 261–268 (1994)). The dependence of blood pressure on salt intake appears to depend on NO, and NO deficiency states are associated with salt-sensitivity (Tolins et al, *Kidney Internat*, 46:230–236 (1994)). Selective inhibition of iNOS in Dahl R rats has been shown to lead to salt-sensitivity and to the development of salt-dependent hypertension similar to Dahl S rats (Rudd et al, *Am J Physiol*, 277: H732–H739 (1999)). In addition, mice deficient in iNOS (iNOS gene eliminated by targeted disruption) may develop hypertension in response to salt feeding (Rudd et al, *Circulation*, 98:1A (1998)).

Nitric oxide also affects myocardial contractility, and does so both by mediating muscarinic-cholinergic slowing of the heart rate and the contractile response to beta-adrenergic stimulation (Balligand et al, *Proc Nat'l Acad Sci USA*, 90:347–351 (1993)). This latter effect appears to be mediated in vivo through the vagus nerve (Hare et al, *J Clin Invest*, 95:360–366 (1995)).

In both vascular smooth muscle cells and cardiomyocytes, NO inhibits cellular proliferation and limits the proliferative response to growth-promoting substances (Garg et al, *J Clin Invest*, 83:1774–1777 (1986)). Left ventricular hypertrophy tends to occur in adult hearts with inadequate capillary proliferation, and this may account for the microvascular ischemia noted in patients with hypertrophy. Capillary proliferation is generally held to be a rare event in normal adult mammalian hearts. However, recent data from a hypertensive rat model, in which left ventricular hypertrophy commonly occurs, show that treatment with a low-dose of an angiotensin-converting enzyme inhibitor insufficient to prevent hypertension and left ventricular hypertrophy can, nonetheless, evoke capillary angiogenesis. Compared with untreated controls, treatment with the angiotensin converting enzyme inhibitor increased myocardial capillary proliferation (Unger et al, *Hypertension*, 20:478482 (1992)), and this effect was believed to be a consequence of inhibiting the degradation and potentiating the action of bradykinin. Bradykinin increases myocardial blood flow by inducing release of NO from microvascular endothelial cells, and increased blood flow is a powerful stimulus for capillary proliferation (Mall et al, *Bas Res Cardiol*, 85:531–540 (1990)).

Normal metabolic processes in vascular cells are associated with the generation of reactive oxygen intermediates that must be neutralized to limit oxidative damage and cellular dysfunction. In the setting of common cardiovascular diseases or disorders or in the presence of common risk factors for atherothrombotic disease, reactive oxygen species (ROS) are generated in abundance, and their rate of synthesis and flux typically exceeds the capacity of endogenous antioxidant mechanisms. Hypercholesterolemia, hyperglycemia (Keaney et al, *Circulation*, 99:189–191 (1999)), cigarette smoking, hyperhomocysteinemia, hypertension, and frank atherosclerosis are all accompanied by an increase in plasma and tissue ROS generation. Superoxide anion, hydrogen peroxide, hydroxyl radical, peroxynitrite, and lipid peroxides all increase in these settings. What remains unknown is whether or not the increase in ROS in these disorder is a primary event, a secondary consequence of the underlying process, or both.

Endogenous antioxidants important for the neutralization (i.e., reduction) of ROS can be categorized into two groups: small-molecule antioxidants and antioxidant enzymes. The former group comprises molecules such as GSH, NADPH, α-tocopherol, vitamin C, and ubiquinol-10; while the latter group comprises the superoxide dismutases, catalase, and glutathione peroxidases. Deficiencies in several of these molecular species have been shown to lead to increased steady-state levels of ROS and vascular dysfunction, including increased platelet activation, arterial thrombosis (Freedman et al, *J Clin Invest*, 97:979–987 (1996); Freedman et al, *Circulation*, 98:1481–1486 (1998)), and reduced production of platelet-derived NO (Kenet et al, *Arterio Thromb Vasc Biol*, 19(8): 2017–2023 (1999)), which is important for limiting expansion of a platelet thrombus (Freedman et al, *Circ Res*, 84:1416–142 (1999)).

ROS generation accompanies the vascular dysfunction associated with several models of atherothrombotic and hypertensive vascular diseases. Hyperhomo-cysteinemic mice (i.e., cystathionine β-synthase knock-out mice) (Eberhardt et al, *Circulation*, 98:144 (1998)), cellular glutathione peroxidase-deficient mice (i.e., cellular glutathione peroxidase knock-out mice), and salt-induced hypertensive rats (i.e., salt-fed Dahl S rats) (Trolliet et al, *Circulation*, 98:1–725 (1998)) all manifest increased vascular ROS, and this increase in ROS is accompanied by reduced NO bio-activity through oxidative inactivation. Endothelial function and NO availability can be improved by improving antioxidant status with a cysteine precursor (Vita et al, *J Clin Invest*, 101:1408–1414 (1998)). In addition, α-tocopherol leads to platelet inhibition (Freedman et al, *Circulation*, 94:2434–2440 (1996)) as one mechanism of its atherothrombotic benefit (Stephens et al, *Lancet*, 347:781–786 (1996)). Salt-loading salt-sensitive individuals (Dahl S rats) lead to an approximate 5-fold increase in plasma $F_2$-isoprostanes (8-epi-prostaglandin $F_2$), and this increase precedes the development of florid hypertension. These data all support the role of oxidant stress in the genesis or evolution of vascular dysfunction and disease, and the importance of antioxidant mechanisms in preventing this pathobiology, particularly with regard to African Americans.

In support of the mechanisms illustrated above, minimum forearm vascular resistance is significantly higher among normotensive blacks than whites (Bassett et al, *Am J Hypertension*, 5:781–786 (1992)), and forearm blood-flow responses to isoproterenol are markedly attenuated in normotensive blacks, suggesting a blunted $\beta_2$-vasodilator response in these individuals (Lang et al, *N Engl J Med*, 333:155–160 (1995)). Blacks tend to have greater left ventricular mass than whites for any given level of blood pressure (Koren et al, *Am J Hypertension*, 6:815–823 (1993); Chaturvedi et al, *J Am Coll Cardiol*, 24:1499–1505 (1994)). While not quantitated in any necropsy study, this response is likely to be accompanied by inadequate capillary angiogenesis, which, in turn, may account for the diastolic dysfunction and the microvascular ischemia observed in blacks. Interestingly, blacks have been observed to have low levels of urinary kallikrein (Zinner et al, *Am J Epidemiol*, 104:124–132 (1976); Levy et al, *J Clin Invest*, 60:129–138 (1977)), the enzyme responsible for the generation of bradykinin from high-molecular-weight kininogen. Thus, were a similar abnormality in bradykinin and bradykinin-mediated NO production to exist in the coronary vasculature, attenuated blood flow responses may result that would limit capillary angiogenic responses and prevent the endothelial proliferative effects of locally derived NO.

As discovered and described herein, African Americans have a unique vascular diathesis that may serve as the basis for clinically important cardiovascular syndromes. For example, differences in the outcome of left ventricular dysfunction may be a consequence of the enhanced (perhaps salt-dependent) increase in oxidant stress coupled with microvascular endothelial dysfunction and an inadequately vascularized, hypertrophied left ventricle. This constellation of pathophysiological abnormalities may provide the substrate for the important differences in outcome between blacks and whites with left ventricular dysfunction (Dreis et al, *N Engl J Med*, 340:609–616 (1999)). In addition, these observations and their clinical consequences suggest that blacks with abnormal endothelial function and nitric oxide insufficiency states would derive direct and, perhaps, disproportionate clinical benefit from enhancing nitric oxide in the vasculature, either by improving endothelial function, providing exogenous nitric oxide donors, or both.

The invention is directed to the treatment and/or prevention of vascular diseases characterized by nitric oxide insufficiency; and for treating and/or preventing Raynaud's syndrome and for treating and/or preventing cardiovascular diseases or disorders by administering nebivolol that is optionally substituted with at least one NO and/or $NO_2$ group, and/or at least one metabolite of nebivolol, that is optionally substituted with at least one NO and/or $NO_2$ group (i.e., nitrosylated and/or nitrosated). Preferably, the nitrosated and/or nitrosylated nebivolol, and/or its nitrosylated and/or nitrosated metabolites are administered as a pharmaceutical composition that further comprises a pharmaceutically acceptable carrier or diluent. The novel compounds and novel compositions of the invention are described in more detail herein.

Nebivolol ((±)-(RSSS)-αα'-(iminobis(methylene)bis-(6-fluoro-3,4-dihydro-2H-1-benzopyran-2-methanol) is a long lasting cardioselective β-blocker having mild vasodilating properties. It is administered as its hydrochloride salt as mixture of equal amounts of its 2 enantiomers (SRRR and RSSS) under the tradenames NEBILET®, NEBILOX® or LOBIVON®. The structure of nebivolol with its four stereogenic centers indicated with an asterisk is shown below:

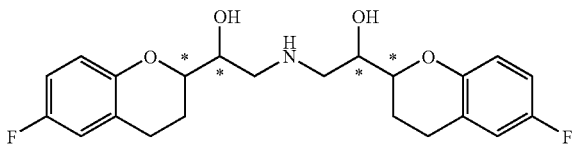

The absorption of nebivolol is rapid and it is extensively metabolized, partly to active metabolites. Compounds contemplated for use in the invention include nebivolol and all its metabolites known in the art and include those described herein, such as, for example, the hydroxy derivatives of nebivolol, the N-alkylated metabolites of nebivolol, and the like. Nebivolol and its metabolites are disclosed in, for example, U.S. Pat. Nos. 4,654,362, 5,759,580, 6,075,046, and in EP 0 145 067, EP 0 334 429, and in WO 95/22325 and WO 96/19987; Van Lommen et al., *J. Pharm. Belg.*, 45(6): 355–360 (1990); Chandrasekhar, S. et al., *Tetrahedron*, 56(34): 6339–6344 (2000); and Fendrickx et al., *J. Chromatogr. A.*, 729: 341–354 (1996); the disclosures of each of which are incorporated by reference herein in their entirety.

In one embodiment, the invention describes nitrosated and/or nitrosylated nebivolol of Formula (I), isomers thereof, and pharmaceutically acceptable salts thereof;

I

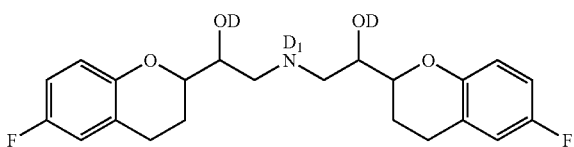

wherein:
D is hydrogen, Q, K or $R_5$;
$D_1$ is hydrogen or $R_5$;
$R_5$ is:

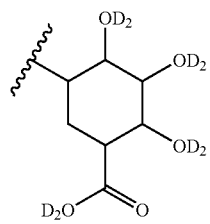

$D_2$ is hydrogen, Q or K;
Q is —NO or —$NO_2$;
K is —$W_a$-$E_b$-$(C(R_e)(R_f))_p$-$E_c$-$(C(R_e)(R_f))_x$-$W_d$-$(C(R_e)(R_f))_y$—$W_i$-$E_j$-$W_g$—$(C(R_e)(R_f))_z$-T-Q;

a, b, c, d, g, i and j are each independently an integer from 0 to 3;
p, x, y and z are each independently an integer from 0 to 10;
W at each occurrence is independently —C(O)—, —C(S)—, -T-, —$(C(R_e)(R_f))_h$—, an alkyl group, an aryl group, a heterocyclic ring, an arylheterocyclic ring, or —$(CH_2CH_2O)_q$—;
E at each occurrence is independently -T-, an alkyl group, an aryl group, —$(C(R_e)(R_f))_h$—, a heterocyclic ring, an arylheterocyclic ring, or —$(CH_2CH_2O)_q$—;
h is an integer form 1 to 10;
q is an integer from 1 to 5;
$R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, an alkylcycloalkyl, an alkylheterocyclic ring, a cycloalkylalkyl, a cycloalkylthio, a cycloalkenyl, an heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cyano an aminoalkyl, an aminoaryl, an aryl, an arylalkyl, an alkylaryl, a carboxamido, a alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, an alkylsulfonyl, an alkylsulfonyloxy, an arylsulfonyl, arylsulphonyloxy, a sulfonic ester, a urea, a phosphoryl, a nitro, $W_h$, -T-Q, or —$(C(R_e)(R_f))_k$-T-Q, or $R_e$ and $R_f$ taken together with the carbons to which they are attached form a carbonyl, a methanthial, a heterocyclic ring, a cycloalkyl group, an aryl group, an oxime or a bridged cycloalkyl group;
k is an integer from 1 to 3;
T at each occurrence is independently a covalent bond, a carbonyl, an oxygen, —$S(O)_o$— or —$N(R_a)R_i$—;
o is an integer from 0 to 2;
$R_a$ is a lone pair of electrons, a hydrogen or an alkyl group;
$R_i$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylaryl, an alkylsulfinyl, an alkylsulfonyl, an alkylsulfonyloxy, an arylsulfinyl, an arylsulfonyl, arylsulphonyloxy, a sulfonamido, a carboxamido, a carboxylic ester, an aminoalkyl, an aminoaryl, —$CH_2$—$C(T-Q)(R_e)(R_f)$, a bond to an adjacent atom creating a double bond to that atom, —$(N_2O_2$—$)^-.M^+$, wherein $M^+$ is an organic or inorganic cation;
with the proviso that the compound of Formula (I) must contain at least one nitrite, nitrate, thionitrite or thionitrate group.

In cases where $R_e$ and $R_f$ are a heterocyclic ring or $R_e$ and $R_f$ taken together with the hetero atom to which they are attached are a heterocyclic ring, then $R_i$ can be a substituent on any disubstituted nitrogen contained within the radical where $R_i$ is as defined herein.

In cases where multiple designations of variables that reside in sequence are chosen as a "covalent bond" or the integer chosen is 0, the intent is to denote a single covalent bond connecting one radical to another. For example, $E_0$ would denote a covalent bond, while $E_2$ denotes (E-E) and $(C(R_e)(R_f))_2$ denotes —$C(R_e)(R_f)$—$C(R_e)(R_f)$—, where $R_e$ and $R_f$ at each occurrence are each independently selected from those moieties defined herein.

Another embodiment of the invention describes the nitrosated and/or nitrosylated metabolites of nebivolol of Formula (II), Formula (III), Formula (IV) or Formula (V), isomers thereof, and pharmaceutically acceptable salts thereof;

wherein the compounds of Formula (II), Formula (II), Formula (IV) and Formula (V) are:

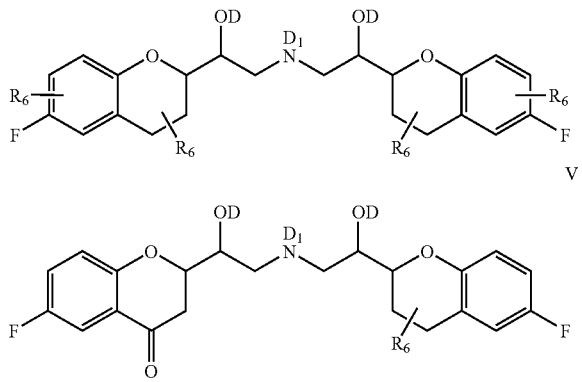

wherein:

$R_6$ at each occurrence is independently a hydrogen, a hydroxy or —OD;

D and $D_1$ are as defined herein; and with the proviso that the compounds of Formula (II), Formula (III), Formula (IV) and Formula (V), must contain at least one nitrite, nitrate, thionitrite or thionitrate group.

Compounds of the invention, that have one or more asymmetric carbon atoms, can exist as the optically pure enantiomers, pure diastereomers, mixtures of enantiomers, mixtures of diastereomers, racemic mixtures of enantiomers, diastereomeric racemates or mixtures of diastereomeric racemates. It is to be understood that the invention anticipates and includes within its scope all such isomers and mixtures thereof.

The parent nebivolol compound and its metabolites can be synthesized by one skilled in the art following the methods described in, for example, U.S. Pat. Nos. 4,654,362, 5,759,580, 6,075,046, and in EP 0 145 067, EP 0 334 429, and in WO 95/22325 and WO 96/19987; Van Lommen et al., *J. Pharm. Belg.*, 45(6): 355–360 (1990); Chandrasekhar, S. et al., *Tetrahedron*, 56(34): 6339–6344 (2000); and Fendrickx et at., *J. Chromatogr. A.*, 729: 341–354 (1996); the disclosure of each of which are incorporated by reference herein in their entirety. The parent nebivolol compound and its metabolites can be nitrosated and/or nitrosylated through one or more sites such as oxygen (hydroxyl condensation), sulfur (sulfhydryl condensation), and/or nitrogen. The nitrosated and nitrosylated compounds of the invention can be prepared using conventional methods known to one skilled in the art. For example, known methods for nitrosylating compounds are described in U.S. Pat. Nos. 5,380,758 and 5,703,073; WO 97/27749; WO 98/19672; and Oae et al, *Org. Prep. Proc. Int.*, 15(3):165–198 (1983), the disclosures of each of which are incorporated by reference herein in their entirety.

Compounds of the invention can be synthesized following the methods described herein. The reactions are performed in solvents appropriate to the reagents, and materials used are suitable for the transformations being effected. It is understood by one skilled in the art of organic synthesis that the functionality present in the molecule must be consistent with the chemical transformation proposed. This will, on occasion, necessitate judgment by the routineer as to the order of synthetic steps, protecting groups required, and deprotection conditions. Substituents on the starting materials may be incompatible with some of the reaction conditions required in some of the methods described, but alternative methods and substituents compatible with the reaction conditions will be readily apparent to one skilled in the art. The use of sulfur and oxygen protecting groups is known in the art for protecting thiol and alcohol groups against undesirable reactions during a synthetic procedure and many such protecting groups are known, e.g., T. H. Greene and P. G. M. Wuts, *Protective Groups in Organic Synthesis*, John Wiley & Sons, New York (1999), which is incorporated herein in its entirety.

Compounds of the invention can be synthesized as shown in FIGS. 1 to 16. Nitroso compounds of Formula (I) wherein $R_e$, $R_f$, and p are defined as herein, $D^1$ is hydrogen, $P^{1'}$ is an acetyl or trifluoroacetyl ester, and hydrogen and an O-nitrosylated ester are representative of the D groups as defined herein, may be prepared as outlined in FIG. 1. The amine group of Formula 1 is protected to afford the compound of Formula 2, wherein $P^3$ is as defined herein. Preferred protecting groups for the amine are as a carbamate, such as, a benzyl or tert-butyl carbamate, or an amide, such as, a trifluoroacetamide. An alcohol group of Formula 2 is converted to the ester of Formula 3, wherein p, $R_e$ and $R_f$ are defined herein, by reaction with an appropriate protected alcohol containing activated acylating agent, wherein $P^1$ is as defined herein. Preferred methods for the formation of esters are reacting the alcohol with the preformed acid chloride or symmetrical anhydride of the protected alcohol containing acid or condensing the alcohol and protected alcohol containing acid in the presence of a dehydrating agent, such as, dicyclohexylcarbodiimide (DCC) or 1-ethyl-3-(3-dimethylaminopropyl)carbodiimide hydrochloride (EDAC.HCl) with or without a catalyst, such as, 4-dimethylaminopyridine (DMAP) or 1-hydroxybenzotriazole (HOBt). Preferred protecting groups for the alcohol moiety are silyl ethers, such as, a trimethylsilyl or a tert-butyldimethylsilyl ether. Protection of the remaining secondary alcohol as an ester, such as, an acetyl or trifluoroacetyl ester, followed by deprotection of the silylated hydroxyl moiety (fluoride ion is the preferred method for removing silyl ether protecting groups) and then reaction with a suitable nitrosylating agent, such as, thionyl chloride nitrite, thionyl dinitrite, or nitrosonium tetrafluoroborate, in a suitable anhydrous solvent, such as, dichloromethane, THF, DMF, or acetonitrile, with or without an amine base, such as, pyridine or triethylamine, affords the compound of Formula 4. The compound of Formula 4 is then converted to the compound of Formula IA by deprotecting the amine and remaining hydroxyl group. Hydrogen in the presence of a transition metal catalyst, such as, palladium or platinum, is a preferred method for removing benzyl ether and benzyl carbamate protecting groups, strong anhydrous acids, such as, trifluoroacetic acid or hydrochloric acid in methanol, dioxane or ethyl acetate are preferred for removing the t-butyl carbamate protecting group and mild base, such as, aqueous sodium or potassium carbonate or ammonia in methanol, are the preferred methods for removing trifluoroacetamide, trifluoroacetyl ester or acetyl ester protecting groups.

Figure 2:
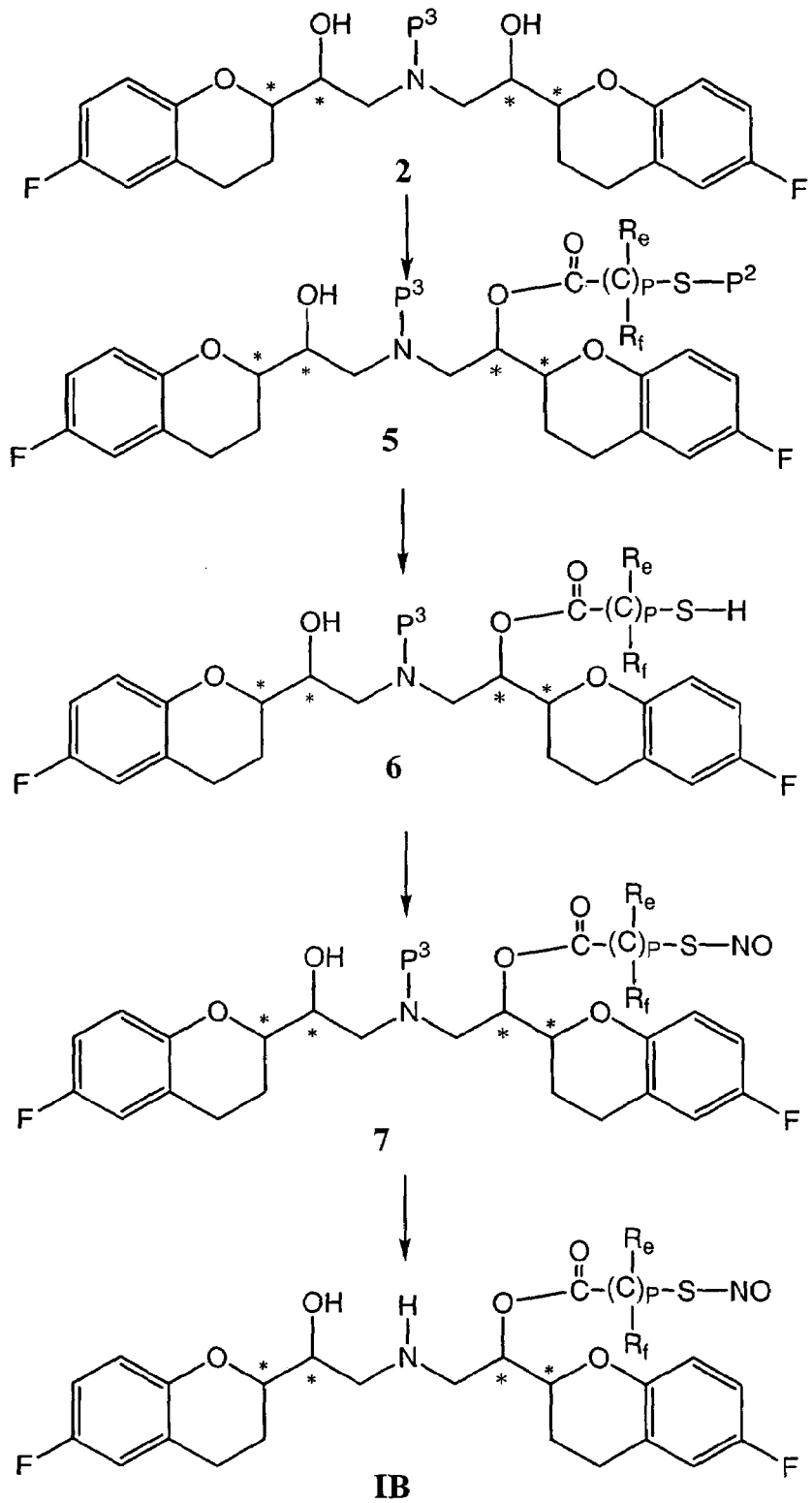
FIG. 2 is the synthetic scheme for the preparation of nitrosothiol containing compounds of Formula (I).

Nitroso compounds of Formula (I) wherein $P^3$, $R_e$, $R_f$, and p are as defined herein, $D^1$ is hydrogen, and a S-nitrosylated ester are representative of the D groups as defined herein, may be prepared as outlined in FIG. 2. The compound of Formula 2, wherein $P^3$ is as defined herein, with the preferred protecting group for the amine being a carbamate, such as, a t-butyl carbamate, is converted to the ester of Formula 5, wherein p, $R_e$ and $R_f$ are as defined herein, by reaction with an appropriate protected thiol containing activated acylating agent, wherein $P^2$ is as defined herein. Preferred methods for the formation of esters are reacting the alcohol with the preformed acid chloride or symmetrical anhydride of the protected thiol containing acid or condensing the alcohol and protected thiol containing acid in the presence of a dehydrating agent, such as, DCC or EDAC.HCl, with or without a catalyst, such as, DMAP or HOBt. Preferred protecting groups for the thiol moiety are as a thioester, such as, a thioacetate or thiobenzoate, as a disulfide, as a thiocarbamate, such as, N-methoxymethyl thiocarbamate, or as a thioether, such as, a paramethoxybenzyl thioether, a tetrahydropyranyl thioether or a 2,4,6-trimethoxybenzyl thioether. Deprotection of the thiol moiety (zinc in dilute aqueous acid, triphenylphosphine in water and sodium borohydride are the preferred methods for reducing disulfide groups, while aqueous base is typically utilized to hydrolyze thioesters, and N-methoxymethyl thiocarbamates and mercuric trifluoroacetate, or silver nitrate are the preferred methods to remove a paramethoxybenzyl thioether, a tetrahydropyranyl thioether or a 2,4,6-trimethoxybenzyl thioether group) affords a compound of Formula 6. Reaction of the compound of Formula 6 with an eqimolar equivalent, based upon thiol, of a suitable nitrosylating agent, such as, thionyl chloride nitrite, thionyl dinitrite, a lower alkyl nitrite, such as, tert-butyl nitrite, or nitrosonium tetrafluoroborate in a suitable anhydrous solvent, such as, methylene chloride, THF, DMF, or acetonitrile, with or without an amine base, such as, pyridine or triethylamine affords the compound of Formula 7. Alternatively, treatment of compound 6 with a stoichiometric quantity of sodium nitrite in an acidic aqueous or alcoholic solution affords the compound of Formula 7. The compound of Formula 7 is then converted to the compound of Formula IB by deprotecting the amine (strong acid, such as, HCl in dioxane or trifluoroacetic acid is used to remove a t-butyl carbamate).

Figure 3:
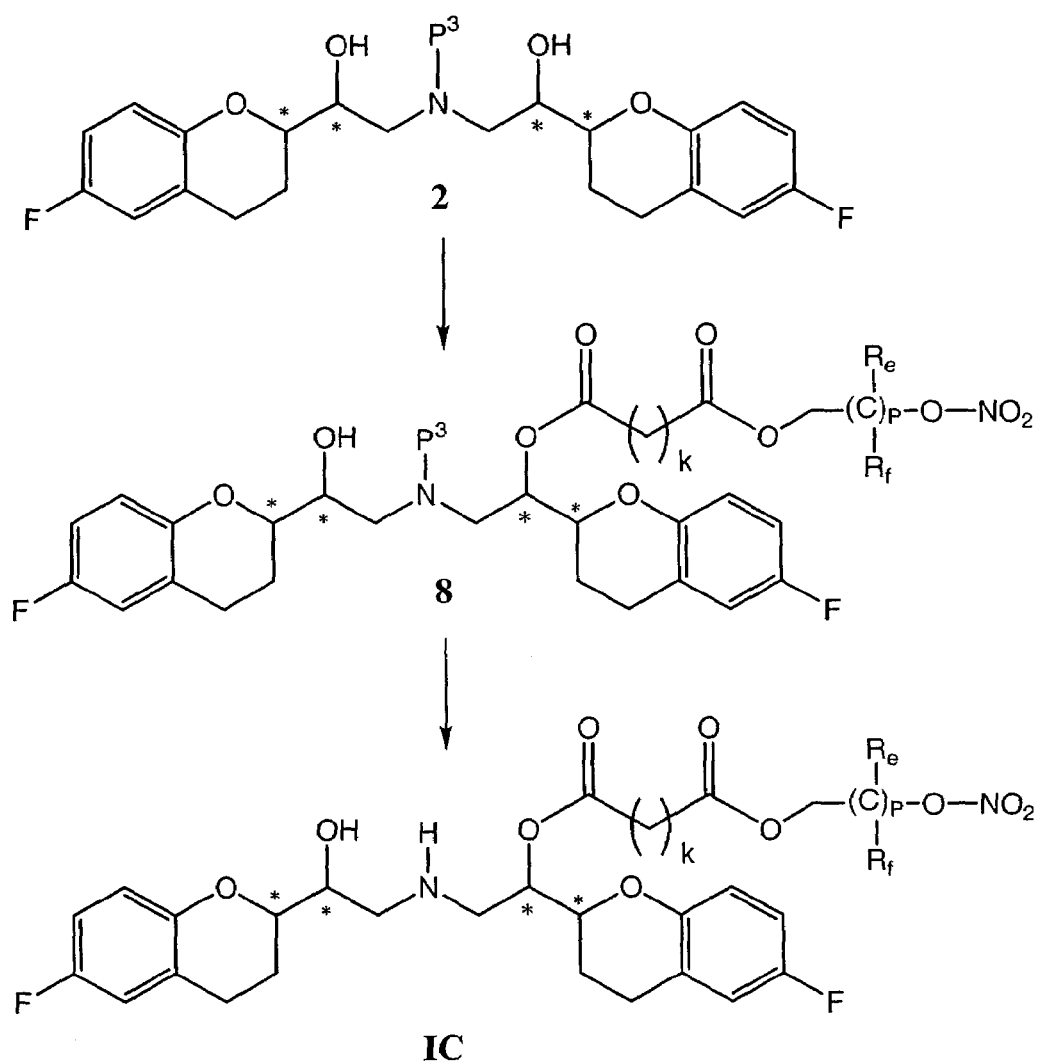
FIG. 3 is the synthetic scheme for the preparation of nitrate containing compounds of Formula (I).

Nitro compounds of Formula (I), wherein $R_e$, $R_f$, k, and p are as defined herein, $D^1$ is hydrogen and a O-nitrosated ester are representative of the D groups as defined herein, may be prepared as outlined in FIG. 3. The compound of Formula 2, wherein $P^3$ is as defined herein, with the preferred protecting group for the amine being a carbamate, such as, a t-butyl carbamate, is converted to the ester of Formula 8, wherein p, $R_e$ and $R_f$ are as defined herein, by reaction with an appropriate nitrate containing activated acylating agent. Preferred methods for the formation of esters are reacting the alcohol with the preformed acid chloride or symmetrical anhydride of the nitrate containing acid or condensing the alcohol and nitrate containing acid in the presence of a dehydrating agent, such as, DCC or EDAC.HCl, with or without a catalyst, such as, DMAP or HOBt. Deprotection of the amine (strong acid, such as, HCl in dioxane or trifluoroacetic acid is used to remove a t-butyl carbamate) affords a compound of Formula IC.

Figure 4:
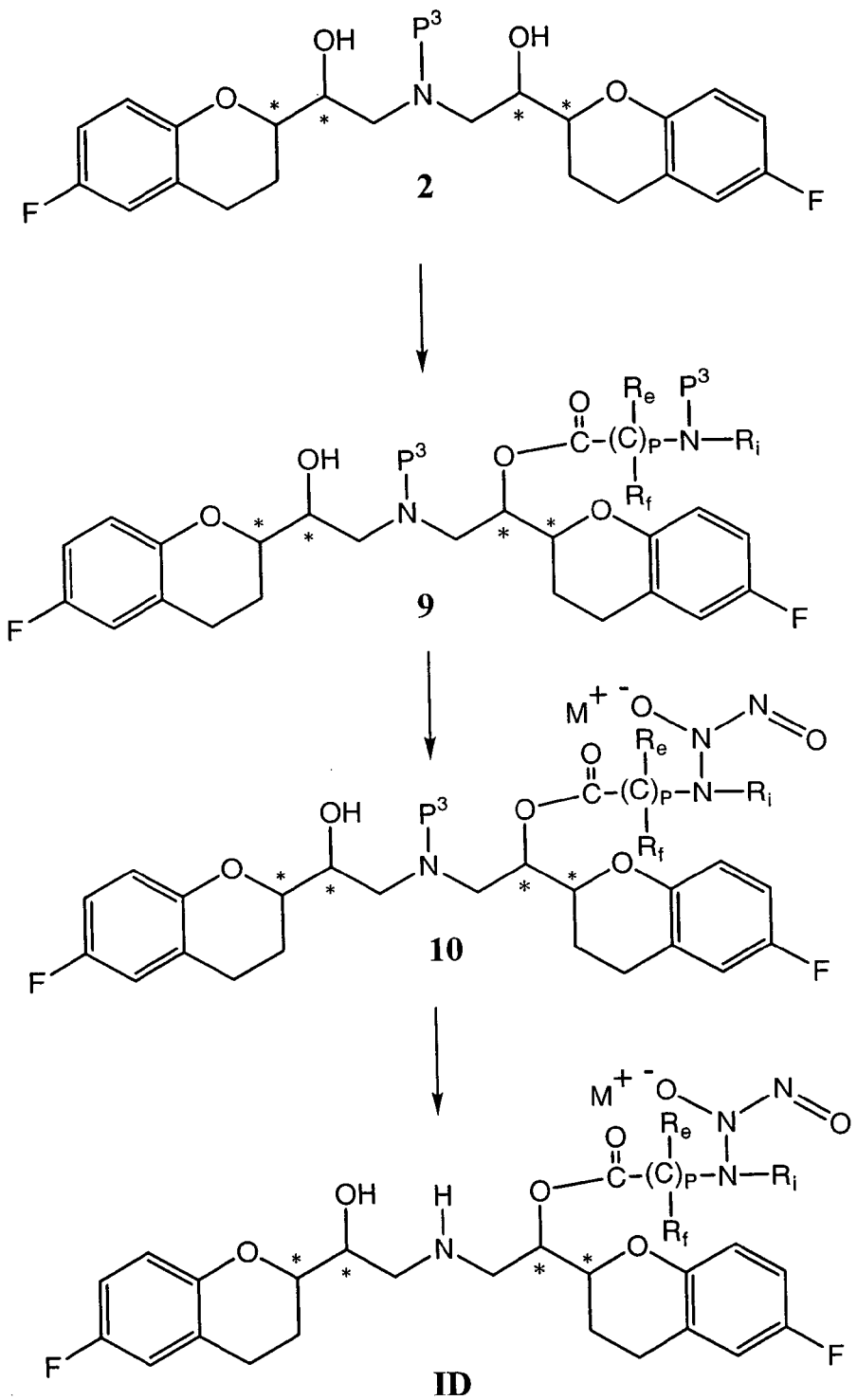
FIG. 4 is the synthetic scheme for the preparation of 2-hydroxy-2-nitrosohydrazine containing compounds of Formula (I).

2-Hydroxy-2-nitrosohydrazine compounds of Formula (I), wherein $R_e$, $R_f$, $R_i$, and p are as defined herein, $D^1$ is hydrogen and hydrogen and a 2-hydroxy-2-nitrosohydrazine ester are representative of the D groups as defined herein, may be prepared as outlined in FIG. 4. The compound of Formula 2, wherein $P^3$ is as defined herein, with the preferred protecting group for the amine being an amide, such as, a trifluoroacetamide, is converted to the ester of Formula 9, wherein p, $R_e$, $R_f$ and $R_i$ are as defined herein, by reaction with an appropriate protected amine containing activated acylating agent wherein $P^{3'}$ is an amine protecting group. Preferred $P^{3'}$ protecting groups for the amine are as a carbamate, such as, a benzyl or tert-butyl carbamate. Preferred methods for the formation of esters are reacting the alcohol with the preformed acid chloride or symmetrical anhydride of the protected amine containing acid or condensing the alcohol and protected amine containing acid in the presence of a dehydrating agent, such as, DCC or EDAC.HCl, with or without a catalyst, such as, DMAP or HOBt. Removal of the $P^{3'}$ amine protecting group (hydrogen in the presence of a transition metal catalyst, such as, palladium or platinum, is a preferred method for removing benzyl carbamate protecting groups, strong anhydrous acids, such as, trifluoroacetic acid or hydrochloric acid in methanol, dioxane or ethyl acetate are preferred for removing the t-butyl carbamate protecting group) followed by treatment of the amine with nitric oxide (1–5 atmospheres) in a dry inert solvent, such as, ether or tetrahydrofuran, affords the compound of Formula 10 wherein $M^+$, is as defined herein. The compound of Formula 10 is then converted to the compound of Formula ID by removing the remaining amine protecting group (mild base, such as, aqueous sodium or potassium carbonate or ammonia in methanol are the preferred methods for removing trifluoroacetamide protecting groups).

Figure 5:
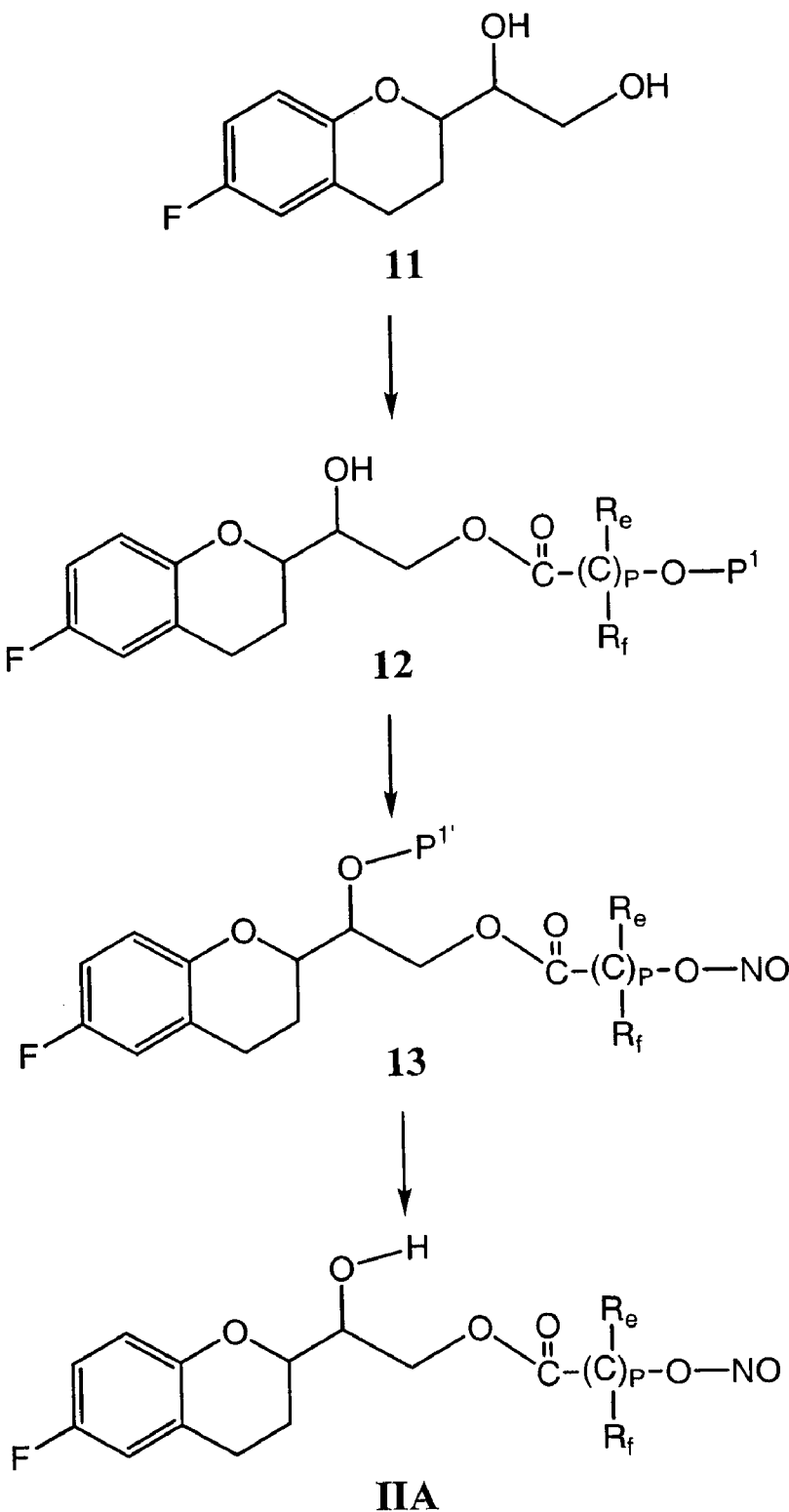
FIG. 5 is the synthetic scheme for the preparation of nitrite containing compounds of Formula (II).

Nitroso compounds of Formula (II) wherein $R_e$, $R_f$, and p are as defined herein, $P^{1'}$ is an acetyl or trifluoroacetyl ester or a benzyl ether, and hydrogen and an O-nitrosylated ester are representative of the D groups as defined above may be prepared as outlined in FIG. 5. An alcohol group of Formula 11 is converted to the ester of Formula 12 wherein p, $R_e$ and $R_f$ are as defined herein by reaction with an appropriate protected alcohol containing activated acylating agent, wherein $P^1$ is as defined herein. Preferred methods for the formation of esters are reacting the alcohol with the preformed acid chloride or symmetrical anhydride of the protected alcohol containing acid or condensing the alcohol and protected alcohol containing acid in the presence of a dehydrating agent, such as, DCC or EDAC.HCl, with or without a catalyst, such as, DMAP or HOBt. Preferred protecting groups for the alcohol moiety are silyl ethers, such as, a trimethylsilyl or tert-butyldimethylsilyl ether. Protection of the remaining secondary alcohol as an ester, such as, an acetyl or trifluoroacetyl ester, followed by deprotection of the silylated hydroxyl moiety (fluoride ion is the preferred method for removing silyl ether protecting groups) and then reaction a suitable nitrosylating agent, such as, thionyl chloride nitrite, thionyl dinitrite, or nitrosonium tetrafluoroborate, in a suitable anhydrous solvent, such as, dichloromethane, THF, DMF, or acetonitrile, with or without an amine base, such as, pyridine or triethylamine affords the compound of Formula 13. The compound of Formula 13 is then converted to the compound of Formula IIA by deprotecting the remaining hydroxyl group. Hydrogen in the presence of a transition metal catalyst, such as, palladium or platinum, is a preferred method for removing the benzyl ether protecting group, and mild base, such as, aqueous sodium or potassium carbonate or ammonia in methanol, are the preferred methods for removing, trifluoroacetyl ester or acetyl ester protecting groups.

Figure 6:
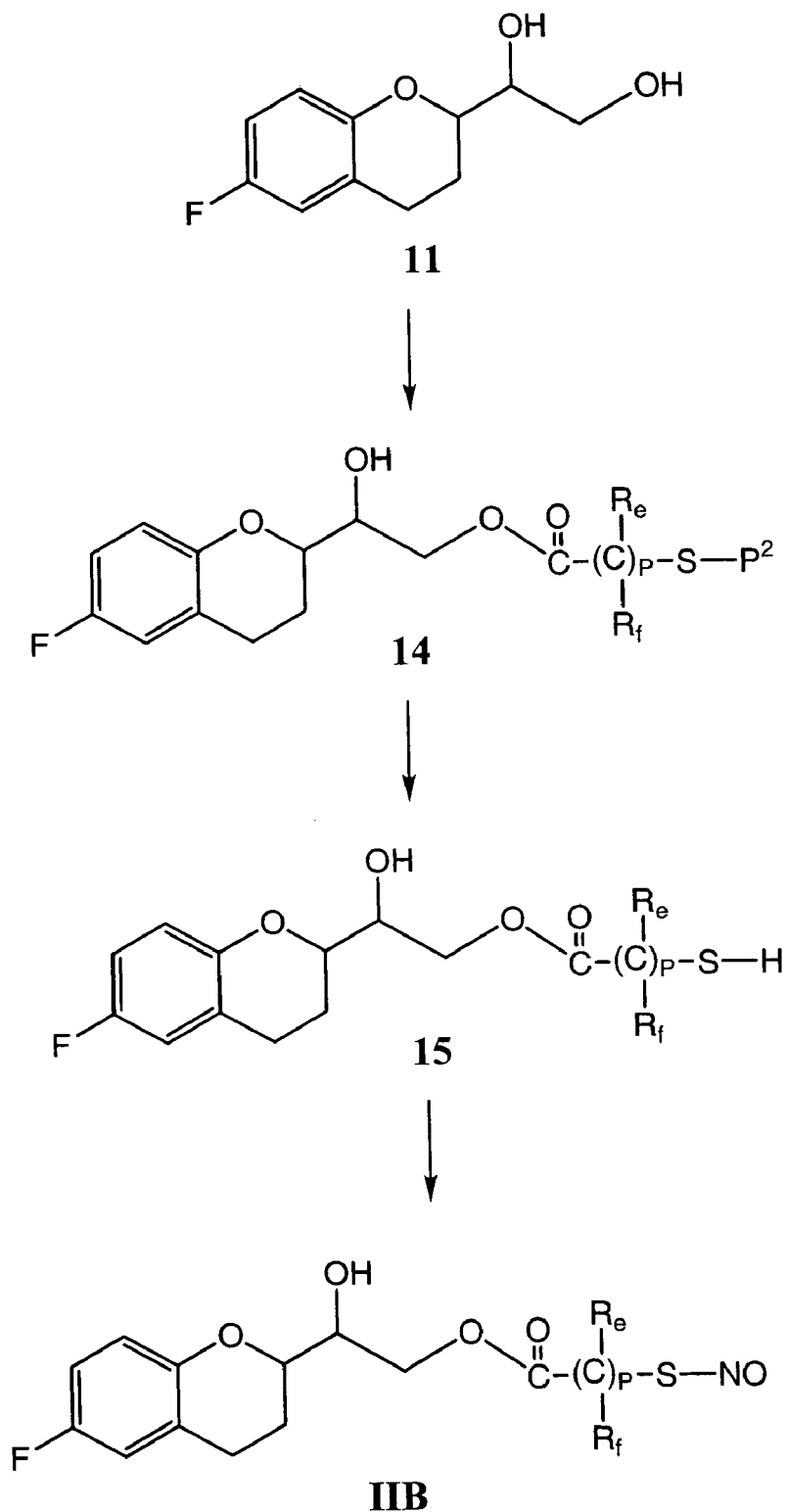
FIG. 6 is the synthetic scheme for the preparation of nitrosothiol containing compounds of Formula (II).

Nitroso compounds of Formula (II) wherein $R_e$, $R_f$, and p are as defined herein, and hydrogen and a S-nitrosylated ester are representative of the D groups as defined herein, may be prepared as outlined in FIG. 6. The compound of Formula 11 is converted to the ester of Formula 14, wherein p, $R_e$ and $R_f$, are as defined herein, by reaction with an appropriate protected thiol containing activated acylating agent, wherein $P^2$ is as defined herein. Preferred methods for the formation of esters are reacting the alcohol with the preformed acid chloride or symmetrical anhydride of the protected thiol containing acid or condensing the alcohol and protected thiol containing acid in the presence of a dehydrating agent, such as, DCC or EDAC.HCl, with or without a catalyst, such as, DMAP or HOBt. Preferred protecting groups for the thiol moiety are as a thioester, such as, a thioacetate or thiobenzoate, as a disulfide, as a thiocarbamate, such as, N-methoxymethyl thiocarbamate, or as a thioether, such as, a paramethoxybenzyl thioether, a tetrahydropyranyl thioether or a 2,4,6-trimethoxybenzyl thioether. Deprotection of the thiol moiety (zinc in dilute aqueous acid, triphenylphosphine in water and sodium borohydride are preferred methods for reducing disulfide groups. while aqueous base is typically utilized to hydrolyze thioesters and N-methoxymethyl thiocarbamates and mercuric trifluoroacetate, silver nitrate, or strong acids, such as, trifluoroacetic or hydrochloric acid and heat are used to remove a paramethoxybenzyl thioether, a tetrahydropyranyl thioether or a 2,4,6-trimethoxybenzyl thioether group) to afford a compound of Formula 15. Reaction of the compound of Formula 15 with an equimolar equivalent (based upon thiol) of a suitable nitrosylating agent, such as, thionyl chloride nitrite, thionyl dinitrite, or a lower alkyl nitrite, such as, tert-butyl nitrite, or nitrosonium tetrafluoroborate in a suitable anhydrous solvent, such as, methylene chloride, THF, DMF, or acetonitrile, with or without an amine base, such as, pyridine or triethylamine, affords the compound of Formula IIB. Alternatively, treatment of compound 15 with a stoichiometric quantity of sodium nitrite in an acidic aqueous or alcoholic solution affords the compound of Formula IIB.

Figure 7:
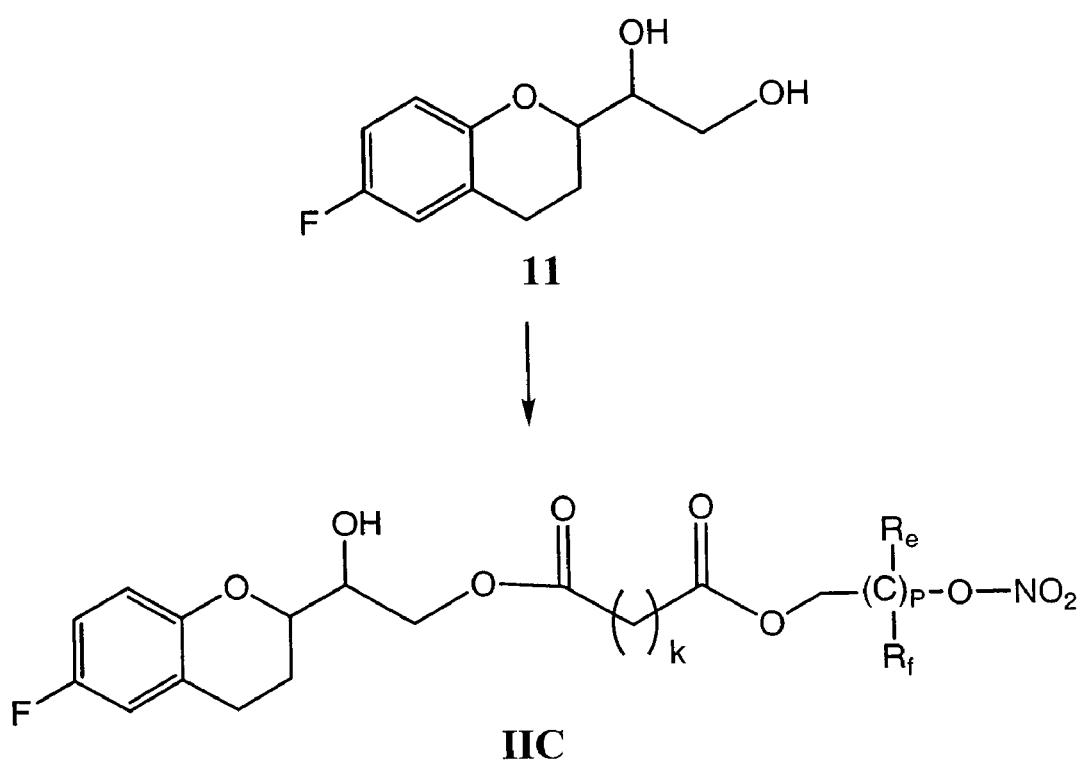
FIG. 7 is the synthetic scheme for the preparation of nitrate containing compounds of Formula (II).

Nitro compounds of Formula (II), wherein $R_e$, $R_f$, k, and p are as defined here, and hydrogen and an O-nitrosated ester are representative of the D groups as defined herein, may be prepared as outlined in FIG. 7. The compound of Formula 11 is converted to the ester of Formula IIC, wherein p, k, $R_e$ and $R_f$, are as defined herein, by reaction with an appropriate nitrate containing activated acylating agent. Preferred methods for the formation of esters are reacting the alcohol with the preformed acid chloride or symmetrical anhydride of the nitrate containing acid or condensing the alcohol and nitrate containing acid in the presence of a dehydrating agent, such as, DCC or EDAC.HCl, with or without a catalyst, such as, DMAP or HOBt.

Figure 8:
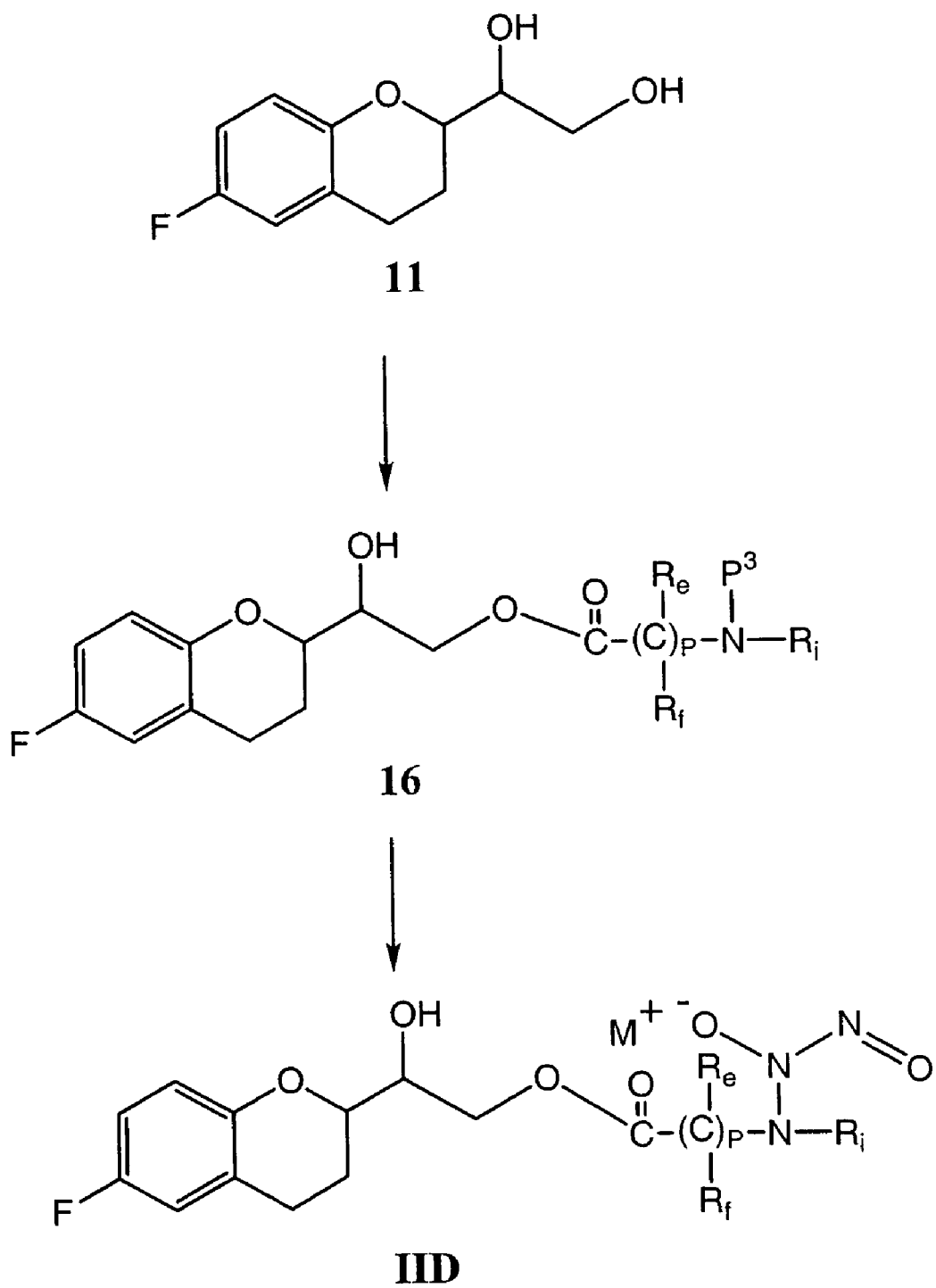
FIG. 8 is the synthetic scheme for the preparation of 2-hydroxy-2-nitrosohydrazine containing compounds of Formula (II).

2-Hydroxy-2-nitrosohydrazine compounds of Formula (II), wherein $R_e$, $R_f$ and $R_i$ and p, are as defined herein, and hydrogen and a 2-hydroxy-2-nitrosohydrazine ester are representative of the D groups, as defined herein, may be prepared as outlined in FIG. 8. The compound of Formula 11 is converted to the ester of Formula 16, wherein p, $R_i$, $R_e$ and $R_f$ are as defined herein, by reaction with an appropriate protected amine containing activated acylating agent, wherein $P^3$ is an amine protecting group. Preferred protecting groups for the amine are as a carbamate, such as, a benzyl or tert-butyl carbamate. Preferred methods for the formation of esters are reacting the alcohol with the preformed acid chloride or symmetrical anhydride of the protected amine containing acid or condensing the alcohol and protected amine containing acid in the presence of a dehydrating agent, such as, DCC or EDAC.HCl, with or without a catalyst, such as, DMAP or HOBt. Removal of the $P^3$ amine protecting group (hydrogen in the presence of a transition metal catalyst, such as, palladium or platinum, is a preferred method for removing benzyl carbamate protecting groups, while strong anhydrous acids, such as, trifluoroacetic acid or hydrochloric acid in methanol, dioxane or ethyl acetate, are preferred for removing the t-butyl carbamate protecting group) followed by treatment of the amine with nitric oxide (1–5 atmospheres) in a dry inert solvent, such as, ether or tetrahydrofuran, affords the compound of Formula IID, wherein $M^+$ is as defined herein.

Figure 9:
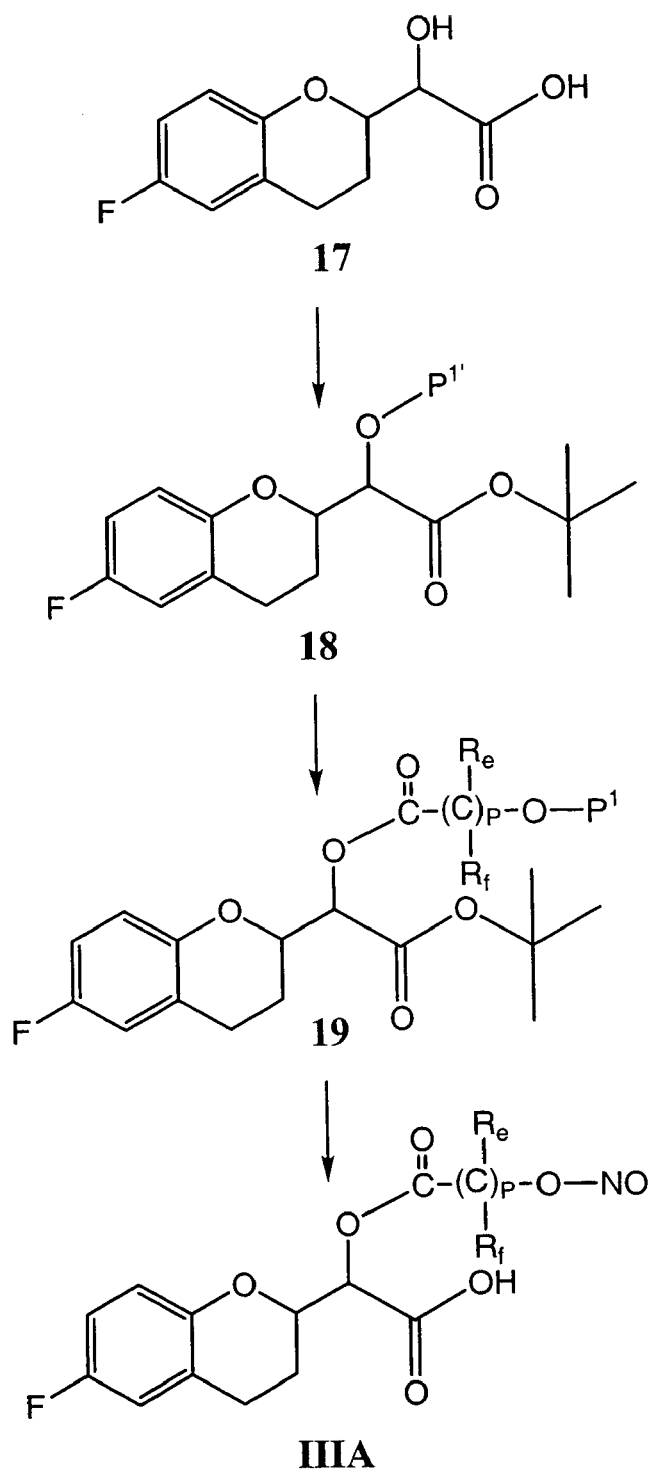
FIG. 9 is the synthetic scheme for the preparation of nitrite containing compounds of Formula (III).

Nitroso compounds of Formula (III) wherein $R_e$, $R_f$ and p are as defined herein, $P^{1'}$ is an acetyl ester or a benzyl carbonate, and hydrogen and an O-nitrosylated ester are representative of the D groups as defined herein, may be prepared as outlined in FIG. 9. The alcohol and acid groups of Formula 17 are protected to afford the compound of Formula 18. Preferred protecting groups for the alcohol are as a carbamate, such as, a benzyl carbonate or an ester, such as, a acetyl ester, while preferred protecting groups for the acids are as an ester, such as, t-butyl ester. Deprotection of the hydroxyl moiety (catalytic hydrogenation is the preferred method for cleaving benzyl carbonates while mild aqueous base removes the acetyl ester group) followed by reaction of the alcohol group with an appropriate protected alcohol containing activated acylating agent, wherein $R_e$, $R_f$ and p and $P^1$, are as defined herein, affords a compound of Formula 19. Preferred methods for the formation of esters are reacting the alcohol with the preformed acid chloride or symmetrical anhydride of the protected alcohol containing acid or condensing the alcohol and protected alcohol containing acid in the presence of a dehydrating agent, such as, DCC or EDAC. HCl, with or without, a catalyst, such as, DMAP or HOBt. Preferred protecting groups for the alcohol moiety are silyl ethers, such as, a tert-butyldimethylsilyl ether. Deprotection of the acid and hydroxyl moieties (strong acid, such as, HCl in dioxane or trifluoroacetic acid cleaves t-butyl esters while fluoride ion is the preferred method for removing silyl ether protecting groups) followed by reaction a suitable nitrosylating agent, such as, thionyl chloride nitrite, thionyl dinitrite, or nitrosonium tetrafluoroborate in a suitable anhydrous solvent, such as, dichloromethane, THF, DMF, or acetonitrile with or without an amine base, such as, pyridine or triethylamine affords the compound of Formula IIIA.

Figure 10:
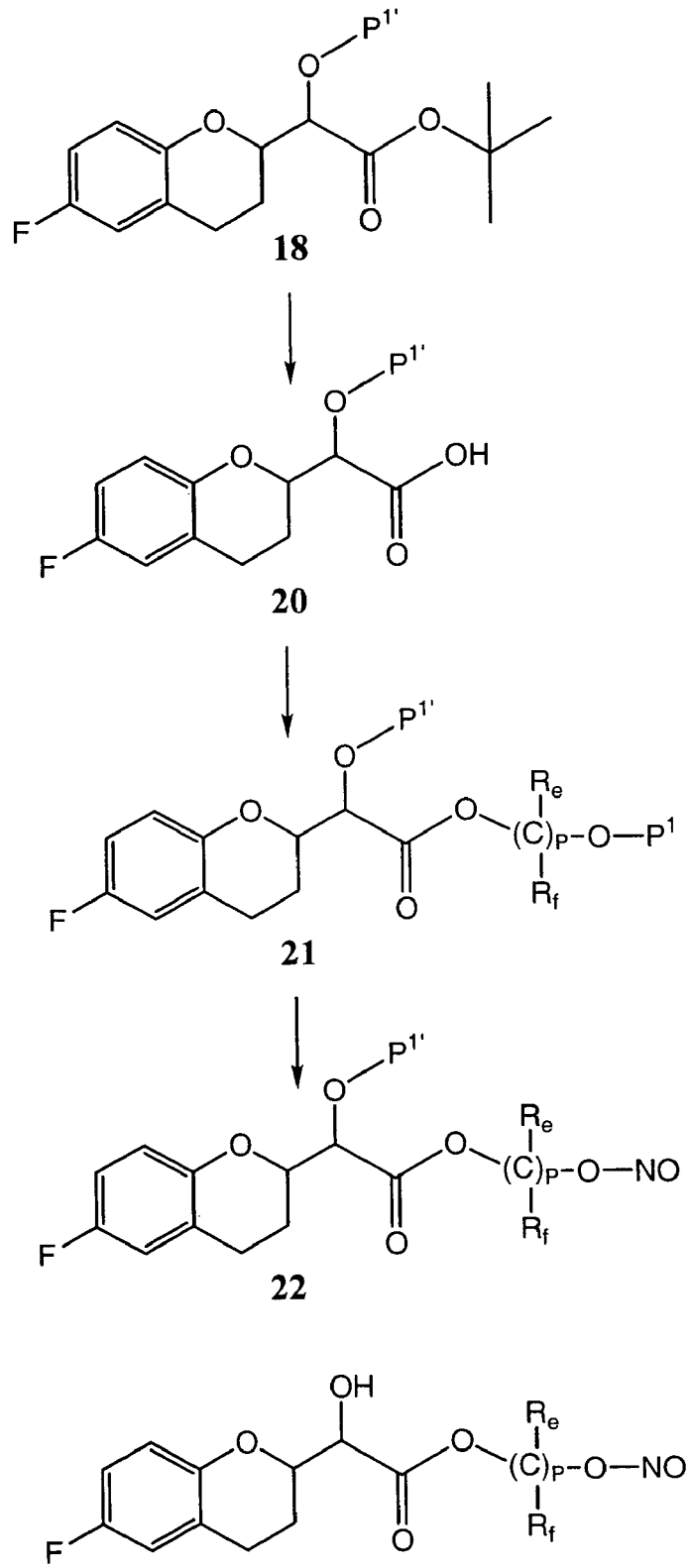
FIG. 10 is the synthetic scheme for the preparation of nitrite containing compounds of Formula (III).

Nitroso compounds of Formula (III) wherein $R_e$, $R_f$ and p are as defined herein, $P^{1'}$ is an acetyl ester or a benzyl carbonate, and hydrogen and an O-nitrosylated ester are representative of the D groups as defined herein, may be prepared as outlined in FIG. 10. The compound of Formula 18, wherein the preferred protecting groups for the alcohol are as a carbonate, such as, a benzyl carbonate or an ester, such as, a acetyl ester, while a preferred protecting group for the acid is as an ester, such as, t-butyl ester, is converted to the compound of Formula 20 by removal of the t-butyl ester moiety (strong acid, such as, HCl in dioxane or trifluoroacetic acid cleaves t-butyl esters). The compound of Formula 20 is converted to the ester of Formula 21 by reaction of the acid group with an appropriate protected alcohol containing alcohol, wherein $R_e$, $R_f$, p and $P^1$ are as defined herein. Preferred methods for the formation of esters are reacting the alcohol with the preformed acid chloride or symmetrical anhydride of the protected alcohol containing acid or condensing the alcohol and protected alcohol containing acid in the presence of a dehydrating agent, such as, DCC or EDAC.HCl with or without a catalyst, such as, DMAP or HOBt. Preferred protecting groups for the alcohol moiety on the protected alcohol containing alcohol are silyl ethers, such as, tert-butyldimethylsilyl ether. Deprotection of the silyl hydroxyl moiety (fluoride ion is the preferred method for removing silyl ether protecting groups) followed by reaction a suitable nitrosylating agent, such as, thionyl chloride nitrite, thionyl dinitrite, or nitrosonium tetrafluoroborate in a suitable anhydrous solvent, such as, dichloromethane, THF, DMF, or acetonitrile, with or without an amine base, such as, pyridine or triethylamine, affords the compound of Formula 22. Removal of the remaining hydroxylprotecting group (catalytic hydrogenation is the preferred method for cleaving benzyl carbonates while mild aqueous base removes the acetyl ester group) affords the compound of Formula IIIB.

Figure 11:
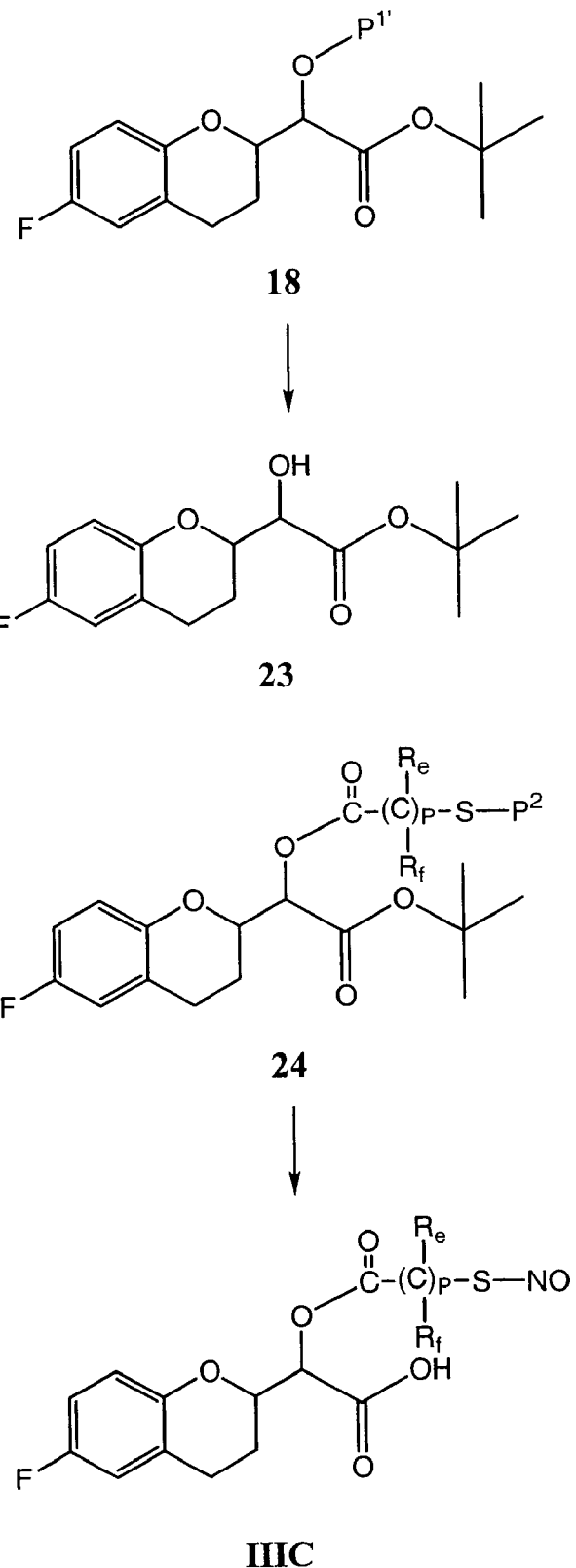
FIG. 11 is the synthetic scheme for the preparation of nitrosothiol containing compounds of Formula (III).

Nitroso compounds of Formula (III), wherein $R_e$, $R_f$, and p are as defined herein, and hydrogen and an S-nitrosylated ester are representative of the D group as defined herein, may be prepared as outlined in FIG. 11. The compound of Formula 18, wherein the preferred protecting groups for the alcohol are as a carbonate, such as, a benzyl carbonate or an ester, such as, a acetyl ester while preferred protecting groups for the acid is as an ester, such as, a t-butyl ester, is converted to the compound of Formula 23 by deprotection of the hydroxyl moiety (catalytic hydrogenation is the preferred method for cleaving benzyl carbonates while mild aqueous base removes the acetyl ester group). Reaction of the alcohol group with an appropriate protected thiol containing activated acylating agent, wherein $R_e$, $R_f$, and p and $P^2$, are as defined herein, afford the compound of Formula 24. Preferred methods for the formation of esters are reacting the alcohol with the preformed acid chloride or symmetrical anhydride of the protected thiol containing acid or condensing the alcohol and protected thiol containing acid in the presence of a dehydrating agent, such as, DCC or EDAC.HCl, with or without a catalyst, such as, DMAP or HOBt. Preferred protecting groups for the thiol moiety are as a thioester, such as, a thioacetate or thiobenzoate, as a disulfide, as a thiocarbamate, such as, N-methoxymethyl thiocarbamate, or as a thioether, such as, a paramethoxybenzyl thioether, a tetrahydropyranyl thioether or a 2,4,6-trimethoxybenzyl thioether. Deprotection of the thiol and acid moieties (zinc in dilute aqueous acid, triphenylphosphine in water and sodium borohydride are preferred methods for reducing disulfide groups, while aqueous base is typically utilized to hydrolyze thioesters and N-methoxymethyl thiocarbamates and mercuric trifluoroacetate, silver nitrate, or strong acids, such as, trifluoroacetic or hydrochloric acid and heat, are used to remove a paramethoxybenzyl thioether, a tetrahydropyranyl thioether, or a 2,4,6-trimethoxybenzyl thioether group as well as t-butyl esters) followed by reaction a suitable nitrosylating agent, such a,s thionyl chloride nitrite, thionyl dinitrite, a lower alkyl nitrite, such as, tert-butyl nitrite, or nitrosonium tetrafluoroborate in a suitable anhydrous solvent, such as, methylene chloride, THF, DMF, or acetonitrile, with or without an amine base, such as, pyridine or triethylamine, affords the compound of Formula IIIC. Alternatively, treatment of the deprotected compound with a stoichiometric quantity of sodium nitrite in an acidic aqueous or alcoholic solution affords the compound of Formula IIIC.

Figure 12:
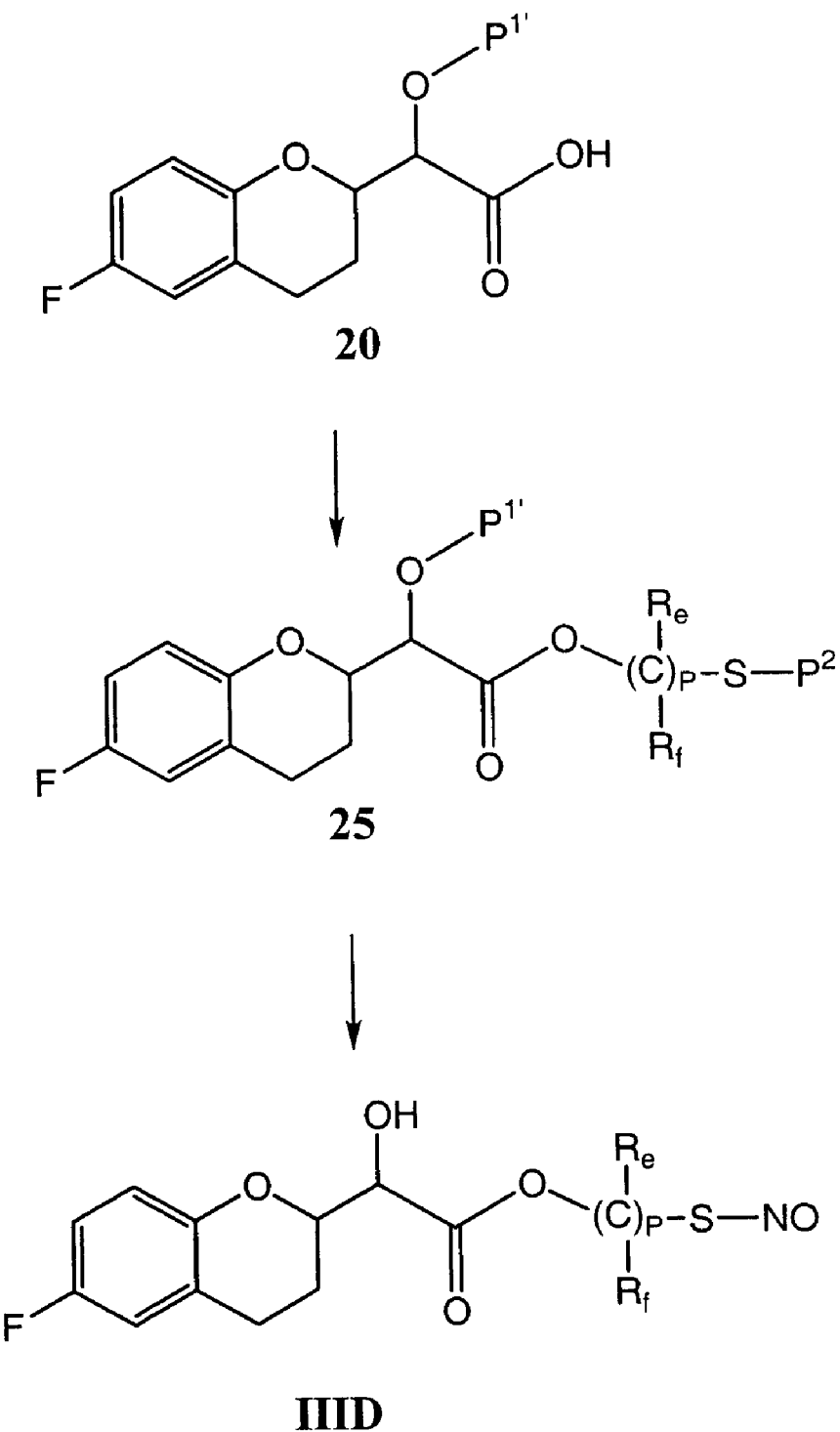
FIG. 12 is the synthetic scheme for the preparation of nitrosothiol containing compounds of Formula (III).

Nitroso compounds of Formula (III) wherein $R_e$, $R_f$, and p are as defined herein, $P^{1'}$ is an acetyl ester or a silyl ether, such as, trimethylsilyl ether or t-butyldimethylsilyl ether, and hydrogen and an S-nitrosylated ester are representative of the D groups as defined herein, may be prepared as outlined in FIG. 12. The compound of Formula 20 is converted to the ester of Formula 25 by reaction of the acid group with an appropriate protected thiol containing alcohol wherein $R_e$, $R_f$, and p and $P^2$, are as defined herein. Preferred methods for the formation of esters are reacting the alcohol with the preformed acid chloride or symmetrical anhydride of the protected alcohol containing acid or condensing the alcohol and protected alcohol containing acid in the presence of a dehydrating agent, such as, DCC or EDAC.HCl, with or without a catalyst, such as, DMAP or HOBt. Preferred protecting groups for the thiol moiety are as a thioester, such as, a thioacetate or thiobenzoate, as a disulfide, as a thiocarbamate such as, N-methoxymethyl thiocarbamate, or as a thioether, such as, a paramethoxybenzyl thioether, a tetrahydropyranyl thioether or a 2,4,6-trimethoxybenzyl thioether. Deprotection of the thiol and alcohol moieties (zinc in dilute aqueous acid, triphenylphosphine in water and sodium borohydride are preferred methods for reducing disulfide groups while aqueous base is typically utilized to hydrolyze thioesters, esters and N-methoxymethyl thiocarbamates and mercuric trifluoroacetate, silver nitrate, or strong acids, such as, trifluoroacetic or hydrochloric acid and heat, are used to remove a paramethoxybenzyl thioether, a tetrahydropyranyl thioether, or a 2,4,6-trimethoxybenzyl thioether group, while fluoride is the preferred method for removing silyl ether protecting groups) followed by reaction a suitable nitrosylating agent, such as, thionyl chloride nitrite, thionyl dinitrite, a lower alkyl nitrite, such as, tert-butyl nitrite, or nitrosonium tetrafluoroborate, in a suitable anhydrous solvent, such as, methylene chloride, THF, DMF, or acetonitrile, with or without an amine base, such as, pyridine or triethylamine, affords the compound of Formula IIID. Alternatively, treatment of the deprotected compound with a stoichiometric quantity of sodium nitrite in an acidic aqueous or alcoholic solution affords the compound of Formula IIID.

Figure 13:
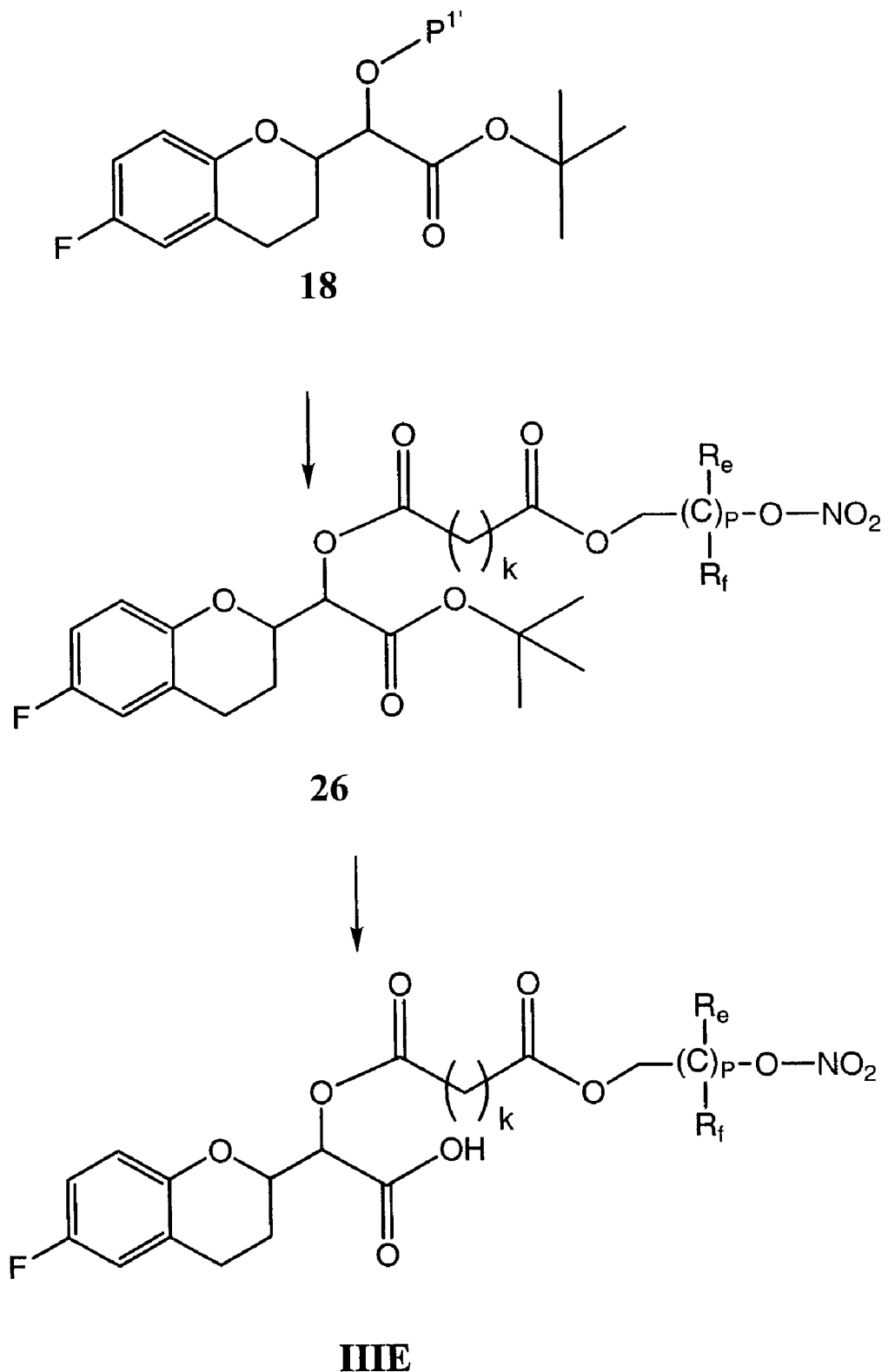
FIG. 13 is the synthetic scheme for the preparation of nitrate containing compounds of Formula (III).

Nitro compounds of Formula (III), wherein $R_e$, $R_f$, k, and p are as defined herein, and hydrogen and an O-nitrosated ester are representative of the D groups as defined herein, may be prepared as outlined in FIG. 13. The compound of Formula 23 is converted to the ester of Formula 26 wherein p, k, $R_e$ and $R_f$ are as defined herein, by reaction with an appropriate nitrate containing activated acylating agent. Preferred methods for the formation of esters are reacting the alcohol with the preformed acid chloride or symmetrical anhydride of the nitrate containing acid or condensing the alcohol and nitrate containing acid in the presence of a dehydrating agent, such as, DCC or EDAC.HCl, with or without a catalyst, such as, DMAP or HOBt. Deprotection of the acid (strong acid, such as, HCl in dioxane or trifluoroacetic acid cleaves t-butyl esters) affords the compound of Formula IIIE.

Figure 14:
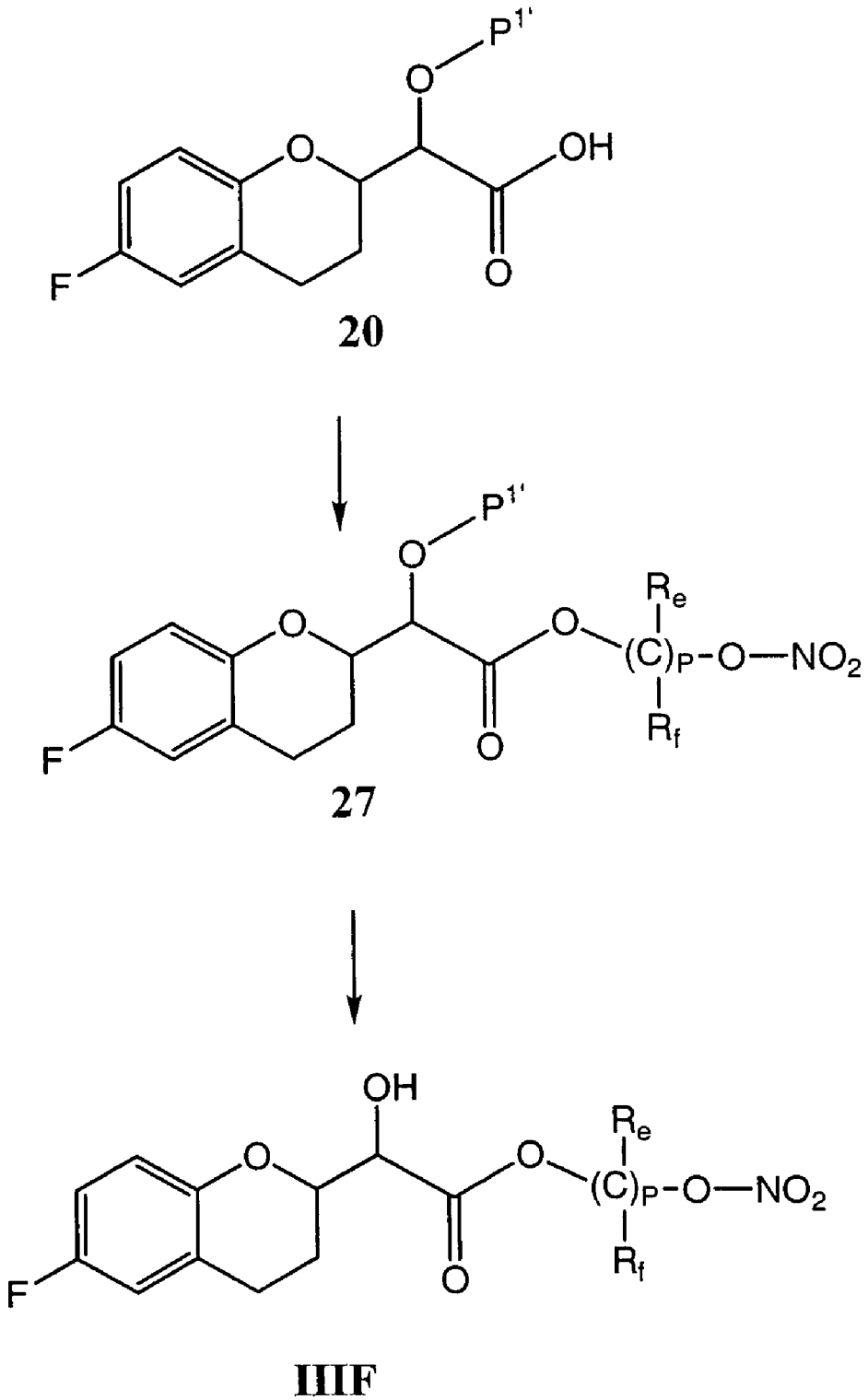
FIG. 14 is the synthetic scheme for the preparation of nitrate containing compounds of Formula (III).

Nitro compounds of Formula (III) wherein $R_e$, $R_f$, and p are as defined herein, and hydrogen and an O-nitrosated ester are representative of the D groups as defined herein, may be prepared as outlined in FIG. 14. The compound of Formula 20, wherein the preferred alcohol protecting group is an ester, such as, an acetyl ester or a silyl ether, such as, a trimethylsilyl of tert-butyldimethyl silyl ether is converted to the ester of Formula 27 wherein p, $R_e$ and $R_f$ are defined as herein, by reaction with an appropriate nitrate containing alcohol. Preferred methods for the formation of esters are reacting the nitrate containing alcohol with the preformed acid chloride or symmetrical anhydride or condensing the nitrate containing alcohol and acid in the presence of a dehydrating agent, such as, DCC or EDAC.HCl, with or without a catalyst, such as, DMAP or HOBt. Removal of the remaining hydroxylprotecting group (mild aqueous base removes the acetyl ester group while fluoride ion is the preferred method for removing silyl ether protecting groups) affords the compound of Formula IIIF.

Figure 15:
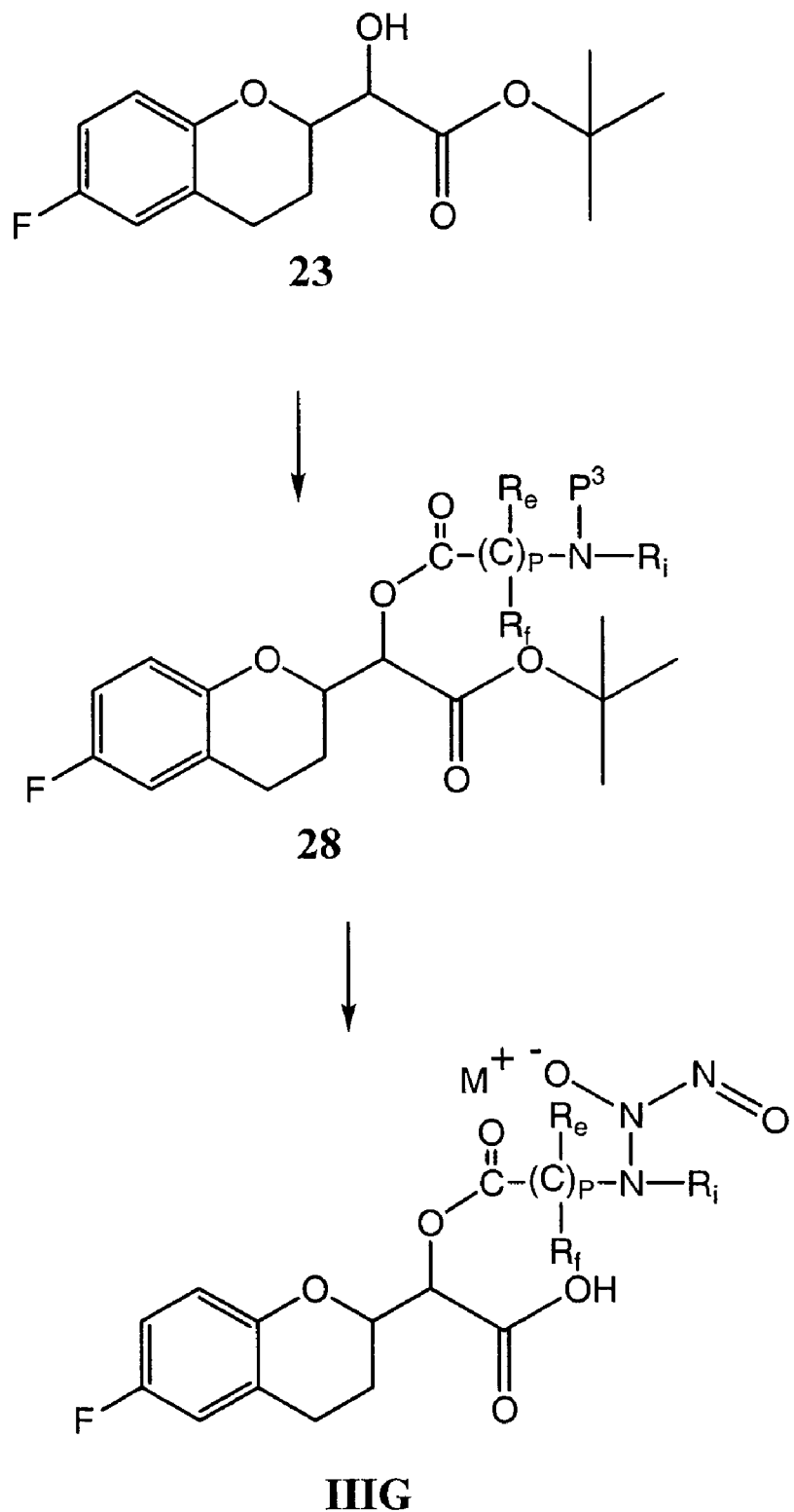
FIG. 15 is the synthetic scheme for the preparation of 2-hydroxy-2-nitrosohydrazine containing compounds of Formula (III).
Figure 16:
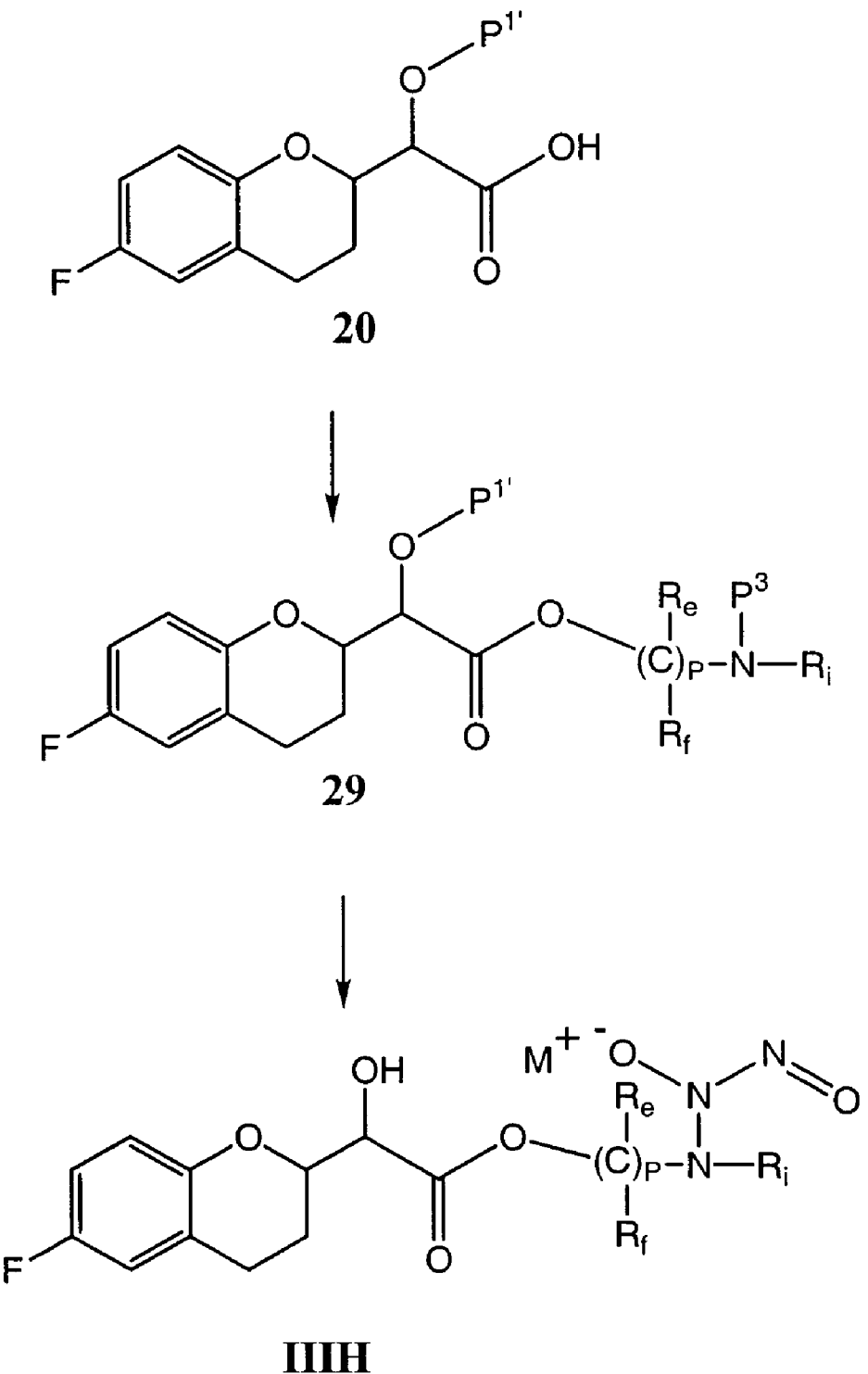
FIG. 16 is the synthetic scheme for the preparation of 2-hydroxy-2-nitrosohydrazine containing compounds of Formula (III).

2-Hydroxy-2-nitrosohydrazine compounds of Formula (III) wherein $R_e$, $R_f$ and $R_i$ and p are as defined herein, and hydrogen and a 2-hydroxy-2-nitrosohydrazine ester are representative of the D groups as defined herein, may be prepared as outlined in FIG. 15. The alcohol group of Formula 25 is converted to the ester of Formula 28 wherein p, $R_e$, $R_f$, $R_i$ and $P^3$ are as defined herein, by reaction with an appropriate protected amine containing activated acylating agent. Preferred methods for the formation of esters are reacting the alcohol with the preformed acid chloride or symmetrical anhydride of the protected amino containing acid or condensing the alcohol and protected amine containing acid in the presence of a dehydrating agent, such as, DCC or EDAC.HCl, with or without a catalyst, such as, DMAP or HOBt. Preferred protecting groups for the amine are as a carbamate, such as, a t-butyl carbamate or a 9-fluorenylmethyl carbamate or an amide, such as, a trifluoroacetamide. Deprotection of the amino and t-butyl ester moieties (strong acid, such as, HCl in dioxane or trifluoroacetic acid, is used to remove a t-butyl carbamate as well as the t-butyl ester groups, while piperidine is used to remove 9-fluorenylmethyl carbamate, and mild aqueous or alcoholic base may be used to cleave a trifluoroacetamide group) followed by treatment of the amine with nitric oxide (1–5 atmospheres) in a dry inert solvent, such as, ether or tetrahydrofuran, affords the compound of Formula IIIG wherein $M^+$ is as defined herein.

2-Hydroxy-2-nitrosohydrazine compounds of Formula (III) wherein $R_e$, $R_f$, $R_i$, and p are as defined herein. $P^1$ is preferably an acetyl ester or silyl protecting group, such as, trimethylsilyl ether or t-butyldimethylsilyl ether, and hydrogen and a 2-hydroxy-2-nitrosohydrazine ester are representative of the D groups as defined herein, may be prepared as outlined in FIG. 16. The acid group of Formula 20 is converted to the ester of Formula 29 wherein p, $R_e$, $R_f$, $R_i$ and $P^3$ are as defined herein, by reaction with an appropriate protected amine containing alcohol. Preferred methods for the formation of esters are reacting the protected amine containing alcohol with the preformed acid chloride or symmetrical anhydride of the acid or condensing the protected amine containing alcohol and acid in the presence of a dehydrating agent, such as, DCC or EDAC.HCl, with or without a catalyst, such as, DMAP or HOBt. Preferred protecting groups for the amine are as a carbamate, such as, a t-butyl carbamate or a 9-fluorenylmethyl carbamate or an amide, such as, a trifluoroacetamide. Deprotection of the amino and alcohol moieties (strong acid, such as, HCl in dioxane or trifluoroacetic acid, is used to remove a t-butyl carbamat, while piperidine is used to remove 9-fluorenylmethyl carbamate, while mild aqueous or alcoholic base may be used to cleave a acetyl ester group, and fluoride is used for removing silyl ethers) followed by treatment of the amine with nitric oxide (1–5 atmospheres) in a dry inert solvent, such as, ether or tetrahydrofuran affords the compound of Formula IIIH, wherein $M^+$ is as defined herein.

The nitrosated and/or nitrosylated nebivolol and the nitrosated and/or nitrosylated metabolites of nebivolol of the invention donate, transfer or release a biologically active form of nitrogen monoxide (nitric oxide). Nitrogen monoxide can exist in three forms: NO– (nitroxyl), NO• (nitric oxide) and $NO^+$ (nitrosonium). NO• is a highly reactive short-lived species that is potentially toxic to cells. This is critical because the pharmacological efficacy of NO depends upon the form in which it is delivered. In contrast to the nitric oxide radical (NO•), nitrosonium ($N^+$) does not react with $O_2$ or $O_2$— species, and functionalities capable of transferring and/or releasing $NO^+$ and NO– are also resistant to decomposition in the presence of many redox metals. Consequently, administration of charged NO equivalents (positive and/or negative) does not result in the generation of toxic by-products or the elimination of the active NO moiety.

Compounds contemplated for use in the invention (e.g., nebivolol and/or nitrosated and/or nitrosylated nebivolol and/or metabolites of nebivolol and/or metabolites of nitrosated and/or nitrosylated nebivolol) are, optionally, used in combination with nitric oxide and compounds that release nitric oxide or otherwise directly or indirectly deliver or transfer nitric oxide to a site of its activity, such as on a cell membrane in vivo.

The term "nitric oxide" encompasses uncharged nitric oxide (NO•) and charged nitrogen monoxide species, preferably charged nitrogen monoxide species, such as nitrosonium ion ($NO^+$) and nitroxyl ion (NO–). The reactive form of nitric oxide can be provided by gaseous nitric oxide. The nitrogen monoxide releasing, delivering or transferring compounds have the structure F—NO, wherein F is a nitrogen monoxide releasing, delivering or transferring moiety, and include any and all such compounds which provide nitrogen monoxide to its intended site of action in a form active for its intended purpose. The term "NO adducts" encompasses any nitrogen monoxide releasing, delivering or transferring compounds, including, for example, S-nitrosothiols, nitrites, nitrates, S-nitrothiols, sydnonimines, 2-hydroxy-2-nitrosohydrazines, (NONOates), (E)-alkyl-2-((E)-hydroxyimino)-5-nitro-3-hexeneamide (FK-409), (E)-alkyl-2-((E)-hydroxyimino)-5-nitro-3-hexeneamines, N-((2Z,3E)-4-ethyl-2-(hydroxyimino)-6-methyl-5-nitro-3-heptenyl)-3-pyridinecarboxamide (FR 146801), nitrosoamines, furoxans as well as substrates for the endogenous enzymes which synthesize nitric oxide. NONOates include, but are not limited to, (Z)-1-(N-methyl-N-(6-(N-methyl-ammoniohexyl)amino))diazen-1-ium-1,2-diolate ("MAHMA/NO"), (Z)-1-(N-(3-ammoniopropyl)-N-(n-propyl)amino)diazen-1-ium-1,2-diolate ("PAPA/NO"), (Z)-1-(N-(3-aminopropyl)-N-(4-(3-aminopropylammonio) butyl)-amino)diazen-1-ium-1,2-diolate (spermine NONOate or "SPER/NO") and sodium (Z)-1-(N,N-diethylamino) diazenium-1,2-diolate (diethylamine NONOate or "DEA/NO") and derivatives thereof. NONOates are also described in U.S. Pat. Nos. 6,232,336, 5,910,316 and 5,650,447, the disclosures of which are incorporated herein by reference in their entirety. The "NO adducts" can be mono-nitrosylated, poly-nitrosylated, mono-nitrosated and/or poly-nitrosated at a variety of naturally susceptible or artificially provided binding sites for biologically active forms of nitrogen monoxide.

One group of NO adducts is the S-nitrosothiols, which are compounds that include at least one —S—NO group. These compounds include S-nitroso-polypeptides (the term "polypeptide" includes proteins and polyamino acids that do not possess an ascertained biological function, and derivatives thereof); S-nitrosylated amino acids (including natural and synthetic amino acids and their stereoisomers and racemic mixtures and derivatives thereof); S-nitrosylated sugars; S-nitrosylated, modified and unmodified, oligonucleotides (preferably of at least 5, and more preferably 5–200 nucleotides); straight or branched, saturated or unsaturated, aliphatic or aromatic, substituted or unsubstituted S-nitrosylated hydrocarbons; and S-nitroso heterocyclic compounds. S-nitrosothiols and methods for preparing them are described in U.S. Pat. Nos. 5,380,758 and 5,703,073; WO 97/27749; WO 98/19672; and Oae et al, Org. Prep. Proc. Int., 15(3):165–198 (1983), the disclosures of each of which are incorporated by reference herein in their entirety.

Another embodiment of the invention is S-nitroso amino acids where the nitroso group is linked to a sulfur group of a sulfur-containing amino acid or derivative thereof. Such compounds include, for example, S-nitroso-N-acetylcysteine, S-nitroso-captopril, S-nitroso-N-acetylpenicillamine, S-nitroso-homocysteine, S-nitroso-cysteine, S-nitroso-glutathione, S-nitroso-cysteinyl-glycine, and the like.

Suitable S-nitrosylated proteins include thiol-containing proteins (where the NO group is attached to one or more sulfur groups on an amino acid or amino acid derivative thereof) from various functional classes including enzymes, such as tissue-type plasminogen activator (TPA) and cathepsin B; transport proteins, such as lipoproteins; heme proteins, such as hemoglobin and serum albumin; and biologically protective proteins, such as immunoglobulins, antibodies and cytokines. Such nitrosylated proteins are described in WO 93/09806, the disclosure of which is incorporated by reference herein in its entirety. Examples include polynitrosylated albumin where one or more thiol or other nucleophilic centers in the protein are modified.

Other examples of suitable S-nitrosothiols include:

(i) $HS(C(R_e)(R_f))_m SNO$;
(ii) $ONS(C(R_e)(R_f))_m R_e$; and
(iii) $H_2N-CH(CO_2H)-(CH_2)_m-C(O)NH-CH(CH_2SNO)-C(O)NH-CH_2-CO_2H$;

wherein m is an integer from 2 to 20; $R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, an alkylcycloalkyl, an alkylheterocyclic ring, a cycloalkylalkyl, a cycloalkylthio, a cycloalkenyl, an heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cyano an aminoalkyl, an aminoaryl, an aryl, an arylalkyl, an alkylaryl, a carboxamido, a alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, an alkylsulfonyl, an alkylsulfonyloxy, an arylsulfonyl, arylsulphonyloxy, a sulfonic ester, a urea, a phosphoryl, a nitro, $W_h$, -T-Q, or $-(C(R_e)(R_f))_k$-T-Q, or $R_e$ and $R_f$ taken together with the carbons to which they are attached form a carbonyl, a methanthial, a heterocyclic ring, a cycloalkyl group, an aryl group, an oxime or a bridged cycloalkyl group; Q is —NO or —$NO_2$; and T is independently a covalent bond, a carbonyl, an oxygen, —$S(O)_n$— or —$N(R_a)R_i$—, wherein o is an integer from 0 to 2, $R_a$ is a lone pair of electrons, a hydrogen or an alkyl group; $R_i$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylaryl, an alkylsulfinyl, an alkylsulfonyl, an alkylsulfonyloxy, an arylsulfinyl, an arylsulfonyl, arylsulphonyloxy, a sulfonamido, a carboxamido, a carboxylic ester, an aminoalkyl, an aminoaryl, —$CH_2$—C(T-Q)($R_e$)($R_f$), a bond to an adjacent atom creating a double bond to that atom, —$(N_2O_2$—)⁻.$M^+$, wherein $M^+$ is an organic or inorganic cation; with the proviso that when $R_i$ is —$CH_2$—C(T-Q)($R_e$)($R_f$) or —$(N_2O_2$—).$M^+$; then "-T-Q" can be a hydrogen, an alkyl group, an alkoxyalkyl group, an aminoalkyl group, a hydroxy group or an aryl group.

In cases where $R_e$ and $R_f$ are a heterocyclic ring or $R_e$ and $R_f$ taken together with the hetero atom to which they are attached are a heterocyclic ring, then $R_i$ can be a substituent on any disubstituted nitrogen contained within the radical wherein $R_i$ is as defined herein.

Nitrosothiols can be prepared by various methods of synthesis. In general, the thiol precursor is prepared first, then converted to the S-nitrosothiol derivative by nitrosation of the thiol group with $NaNO_2$ under acidic conditions (pH is about 2.5) which yields the S-nitroso derivative. Acids which can be used for this purpose include aqueous sulfuric, acetic and hydrochloric acids. The thiol precursor can also be nitrosylated by reaction with an organic nitrite such as tert-butyl nitrite, or a nitrosonium salt such as nitrosonium tetrafluoroborate in an inert solvent.

Another group of NO adducts for use in the invention, where the NO adduct is a compound that donates, transfers or releases nitric oxide, include compounds comprising at least one ON—O—, ON—N— or ON—C— group. The compounds that include at least one ON—O—, ON—N— or ON—C— group are preferably ON—O—, ON—N— or ON—C-polypeptides (the term "polypeptide" includes proteins and polyamino acids that do not possess an ascertained biological function, and derivatives thereof); ON—O—, ON—N— or ON—C-amino acids (including natural and synthetic amino acids and their stereoisomers and racemic mixtures); ON—O—, ON—N— or ON—C-sugars; ON—O—, ON—N— or ON—C— modified or unmodified oligonucleotides (comprising at least 5 nucleotides, preferably 5–200 nucleotides); ON—O—, ON—N— or ON—C— straight or branched, saturated or unsaturated, aliphatic or aromatic, substituted or unsubstituted hydrocarbons; and ON—O—, ON—N— or ON—C-heterocyclic compounds.

Another group of NO adducts for use in the invention include nitrates that donate, transfer or release nitric oxide, such as compounds comprising at least one $O_2N$—O—, $O_2N$—N—, $O_2N$—S— or $O_2N$—C— group. Preferred among these compounds are $O_2N$—O—, $O_2N$—N—, $O_2N$—S— or $O_2N$—C— polypeptides (the term "polypeptide" includes proteins and also polyamino acids that do not possess an ascertained biological function, and derivatives thereof); $O_2N$—O—, $O_2N$—N—, $O_2N$—S— or $O_2N$—C— amino acids (including natural and synthetic amino acids and their stereoisomers and racemic mixtures); $O_2N$—O—, $O_2N$—N—, $O_2N$—S— or $O_2N$—C-sugars; $O_2N$—O—, $O_2N$—N—, $O_2N$—S— or $O_2N$—C— modified and unmodified oligonucleotides (comprising at least 5 nucleotides, preferably 5–200 nucleotides); $O_2N$—O—, $O_2N$—N—, $O_2N$—S— or $O_2N$—C— straight or branched, saturated or unsaturated, aliphatic or aromatic, substituted or unsubstituted hydrocarbons; and $O_2N$—O—, $O_2N$—N—, $O_2N$—S— or $O_2N$—C— heterocyclic compounds. Preferred examples of compounds comprising at least one $O_2N$—O—, $O_2N$—N—, $O_2N$—S— or $O_2N$—C— group include isosorbide dinitrate, isosorbide mononitrate, clonitrate, erythrityl tetranitrate, mannitol hexanitrate, nitroglycerin, pentaerythritoltetranitrate, pentrinitrol, propatylnitrate and organic nitrates with a sulfhydryl-containing amino acid such as, for example SPM 3672, SPM 5185, SPM 5186 and those disclosed in U.S. Pat. Nos. 5,284,872, 5,428,061, 5,661,129, 5,807,847 and 5,883,122 and in U.S. Provisional Application No. 60/311,175 and in WO 97/46521 and WO 00/54756, the disclosures of each of which are incorporated by reference herein in their entirety.

Another group of NO adducts are N-oxo-N-nitrosoamines that donate, transfer or release nitric oxide and are represented by the Formula: $R^1R^2N$—N(O—$M^+$)—NO, where $R^1$ and $R^2$ are each independently a polypeptide, an amino acid, a sugar, a modified or unmodified oligonucleotide, a straight or branched, saturated or unsaturated, aliphatic or aromatic, substituted or unsubstituted hydrocarbon, or a heterocyclic group, and where $M^+$ is an organic or inorganic cation, such as, for example, an alkyl substituted ammonium cation or a Group I metal cation.

Another group of NO adducts are thionitrates that donate, transfer or release nitric oxide and are represented by the formula: $R^1$—(S)—$NO_2$, where $R^1$ is a polypeptide, an amino acid, a sugar, a modified or unmodified oligonucleotide, a straight or branched, saturated or unsaturated, aliphatic or aromatic, substituted or unsubstituted hydrocarbon, or a heterocyclic group. Preferred are those compounds where $R^1$ is a polypeptide or hydrocarbon with a pair or pairs of thiols that are sufficiently structurally proximate, i.e., vicinal, that the pair of thiols will be reduced to a disulfide. Compounds which form disulfide species release nitroxyl ion (NO–) and uncharged nitric oxide (NO•).

The invention is also directed to compounds that stimulate endogenous NO or elevate levels of endogenous endothelium-derived relaxing factor (EDRF) in vivo or are substrates for the enzyme, nitric oxide synthase. Such compounds include, for example, L-arginine, L-homoarginine, and N-hydroxy-L-arginine, including their nitrosated and nitrosylated analogs (e.g., nitrosated L-arginine, nitrosylated L-arginine, nitrosated N-hydroxy-L-arginine, nitrosylated N-hydroxy-L-arginine, nitrosated L-homoarginine and nitrosylated L-homoarginine), precursors of L-arginine and/or physiologically acceptable salts thereof, including, for example, citrulline, ornithine, glutamine, lysine, polypeptides comprising at least one of these amino acids, inhibitors of the enzyme arginase (e.g., N-hydroxy-L-arginine and 2(S)-amino-6-boronohexanoic acid) and the substrates for nitric oxide synthase, cytokines, adenosin, bradykinin, calreticulin, bisacodyl, and phenolphthalein. EDRF is a vascular relaxing factor secreted by the endothelium, and has been identified as nitric oxide (NO) or a closely related derivative thereof (Palmer et al, *Nature*, 327:524–526 (1987); Ignarro et al, *Proc. Natl. Acad. Sci. USA*, 84:9265–9269 (1987)).

The invention is also based on the discovery that the administration of a therapeutically effective amount of the compounds and compositions described herein is effective for treating and/or preventing vascular diseases characterized by nitric oxide (NO) insufficiency. For example, the patient can be administered a therapeutically effective amount of at least one nitrosated and/or nitrosylated nebivolol of the invention. In another embodiment, the patient can be administered a therapeutically effective amount of at least one nitrosated and/or nitrosylated metabolite of nebivolol. In yet another embodiment, the patient can be administered a therapeutically effective amount of nebivolol, optionally substituted with at least one NO and/or $NO_2$ group, and/or at least one metabolite of nebivolol, optionally substituted with at least one NO and/or $NO_2$ group, and at least one compound that donates, transfers or releases nitric oxide as a charged species, or elevates levels of endogenous EDRF or nitric oxide, or is a substrate for nitric oxide synthase. In another embodiment, the patient can be administered a therapeutically effective amount of nebivolol, optionally substituted with at least one NO and/or $NO_2$ group, and/or at least one metabolite of nebivolol, optionally substituted with at least one NO and/or $NO_2$ group, and, optionally, at least one compound that donates, transfers or releases nitric oxide as a charged species, or elevates levels of endogenous EDRF or nitric oxide, or is a substrate for nitric oxide synthase and/or at least one antioxidant or a pharmaceutically acceptable salt thereof, and/or at least one compound used to treat cardiovascular diseases, or a pharmaceutically acceptable salt thereof. The compound used to treat cardiovascular diseases can optionally be substituted with at least one $NO_2$ group (i.e. nitrosated). The compounds can be administered separately or as a composition.

In the invention the compound that donates, transfers or releases nitric oxide as a charged species, or elevates levels of endogenous EDRF or nitric oxide, or is a substrate for nitric oxide synthase may preferably be isosorbide dinitrate and/or isosorbide mononitrate, more preferably isosorbide dinitrate. Diluted isosorbide dinitrate(1,4,3,6-dianhydro-D-glucitol-2,5-dinitrate), USP, is a white to off-white powder that has a melting point of 70° C. and has an optical rotation of +135° (3 mg/mL, ethanol). It is freely soluble in organic solvents such as ethanol, ether and chloroform, but is sparingly soluble in water. Isosorbide dinitrate is commercially available, for example, under the trade names DILATRATE®-SR (Schwarz Pharma, Milwaukee, Wis.); ISORDIL® and ISORDILR TITRADOSE® (Wyeth Laboratories Inc., Philadelphia, Pa.); and SORBITRATE® (Zeneca Pharmaceuticals, Wilmington, Del.). Isosorbide mononitrate is commercially available, for example, under the trade names IMDUR® (A. B. Astra, Sweden); MONOKET® (Schwarz Pharma, Milwaukee, Wis.); and ISMO® (Wyeth-Ayerst company, Philadelphia, Pa.).

In the invention, the antioxidants include small-molecule antioxidants and antioxidant enzymes. Antioxidant refers to and includes any compound that can react and quench a free radical. Suitable small-molecule antioxidants include, but are not limited to, hydralazine compounds, glutathione, vitamin C, vitamin E, cysteine, N-acetyl-cysteine, β-carotene, ubiquinone, ubiquinol-10, tocopherols, coenzyme Q, and the like. Suitable antioxidant enzymes include, but are not limited to, superoxide dismutase, catalase, glutathione peroxidase, and the like. Suitable antioxidants are described more fully in the literature, such as in Goodman and Gilman, The Pharmacological Basis of Therapeutics (9th Edition), McGraw-Hill, 1995; and the Merck Index on CD-ROM, Twelfth Edition, Version 12:1, 1996; and on STN Express, file phar and file reg. The preferred antioxidant is a hydralazine compound that may preferably be administered as a pharmaceutically acceptable salt; more preferably as hydralazine hydrochloride. Hydralazine hydrochloride is commercially available from, for example, Lederle Standard Products (Pearl River, N.Y.), and Par Pharmaceuticals Inc. (Spring Valley, N.Y.).

The compound used to treat cardiovascular diseases, or a pharmaceutically acceptable salt, include, but are not limited to, angiotensin-converting enzyme (ACE) inhibitors, beta-adrenergic blockers, cholesterol reducers, calcium channel blockers, angiotensin II receptor antagonists, endothelin antagonists, renin inhibitors, and the like, and mixtures thereof.

Suitable angiotensin-converting enzyme inhibitors, include, but are not limited to, alacepril, benazepril, captopril, ceronapril, cilazapril, delapril, duinapril, enalapril, enalaprilat, fosinopril, imidapril, lisinopril, losartan, moveltipril, naphthopidil, pentopril, perindopril, quinapril, ramipril, rentipril, spirapril, temocapril, trandolapril, urapidil, zofenopril, and the like. Suitable angiotensin-converting enzyme inhibitors are described more fully in the literature, such as in Goodman and Gilman, The Pharmacological Basis of Therapeutics (9th Edition), McGraw-Hill, 1995; and the Merck Index on CD-ROM, Twelfth Edition, Version 12:1, 1996; and on STN Express, file phar and file registry.

Suitable beta-adrenergic blockers, include, but are not limited to, acebutolol, alprenolol, amosulalol, arotinolol, atenolol, betaxolol, bethanidine, bevantolol, bisoprolol, bopindolol, bucumolol, bufetolol, bufuralol, bunitrolol, bupranolol, butafilolol, carazolol, carteolol, carvedilol, celiprolol, cetamolol, dilevalol, epanolol, esmolol, indenolol, labetalol, mepindolol, metipranolol, metoprolol, moprolol, nadolol, nadoxolol, nifenalol, nipradilol, oxprenolol, penbutolol, pindolol, practolol, pronethalol, propranolol, sotalol, sulfinalol, talinolol, tertatolol, tilisolol, timolol, toliprolol, xibenolol, and the like. Suitable beta-adrenergic blockers are described more fully in the literature, such as in Goodman and Gilman, The Pharmacological Basis of Therapeutics (9th Edition), McGraw-Hill, 1995; and the Merck Index on CD-ROM, Twelfth Edition, Version 12:1, 1996; and on STN Express, file phar and file registry.

Suitable cholesterol reducers include but are not limited to HMG-CoA reductase inhibitors, such as, for example, lovastatin (MEVACOR®), simvastatin (ZOCOR®), pravastatin (PRAVACHOL®), fluvastatin, cerivastatin (BAYCOL®), atorvastatin (LIPITOR®), and the like; sequestrants such as, for example, cholestyramine, colestipol, sialkylaminoalkyl derivatives of cross-linked dextran, and the like; inhibitors of cholesterol absorption, such as, for example, beta-sitosterol, acyl CoA-cholersterol acyltransferase inhibitors, melinamide, and the like. Suitable calcium channel blockers are described more fully in the literature, such as in Goodman and Gilman, The Pharmacological Basis of Therapeutics (9th Edition), McGraw-Hill, 1995; and the Merck Index on CD-ROM, Twelfth Edition, Version 12:1, 1996; and on STN Express, file phar and file registry.

Suitable calcium channel blockers, include, but are not limited to, amlodipine, aranidipine, barnidipine, benidipine, cilnidipine, clentiazem, diltiazen, efonidipine, fantofarone, felodipine, isradipine, lacidipine, lercanidipine, manidipine, mibefradil, nicardipine, nifedipine, nilvadipine, nisoldipine, nitrendipine, semotiadil, veraparmil, and the like. Suitable calcium channel blockers are described more fully in the literature, such as in Goodman and Gilman, The Pharmacological Basis of Therapeutics (9th Edition), McGraw-Hill, 1995; and the Merck Index on CD-ROM, Twelfth Edition, Version 12:1, 1996; and on STN Express, file phar and file registry.

Suitable endothelin antagonists, include, but are not limited to, bosentan, sulfonamide endothelin antagonists, BQ-123, SQ 28608, and the like. Suitable endothelin antagonists are described more fully in the literature, such as in Goodman and Gilman, The Pharmacological Basis of Therapeutics (9th Edition), McGraw-Hill, 1995; and the Merck Index on CD-ROM, Twelfth Edition, Version 12:1, 1996; and on STN Express, file phar and file registry.

Suitable angiotensin II receptor antagonists, include, but are not limited to, ciclosidomine, eprosartan, furosemide, irbesartan, losartan, saralasin, valsartan, and the like. Suitable angiotensin II receptor antagonists are described more fully in the literature, such as in Goodman and Gilman, The Pharmacological Basis of Therapeutics (9th Edition), McGraw-Hill, 1995; and the Merck Index on CD-ROM, Twelfth Edition, Version 12:1, 1996; and on STN Express, file phar and file registry.

Suitable renin inhibitors, include, but are not limited to, enalkrein, RO 42-5892, A 65317, CP 80794, ES 1005, ES 8891, SQ 34017, and the like). Suitable renin inhibitors are described more fully in the literature, such as in Goodman and Gilman, The Pharmacological Basis of Therapeutics (9th Edition), McGraw-Hill, 1995; and the Merck Index on CD-ROM, Twelfth Edition, Version 12:1, 1996; and on STN Express, file phar and file registry.

The compound used to treat cardiovascular diseases, or a pharmaceutically acceptable salt, can be nitrosated through one or more sites such as oxygen (hydroxyl condensation), sulfur (sulfhydryl condensation), and/or nitrogen. The nitrosated angiotensin-converting enzyme inhibitors, nitrosated beta-adrenergic blockers, nitrosated cholesterol reducer, nitrosated calcium channel blockers, nitrosated endothelin antagonists, nitrosated angiotensin II receptor antagonists and nitrosated renin inhibitors of the invention include any known angiotensin-converting enzyme inhibitors, beta-adrenergic blockers, cholesterol reducer, calcium channel blockers, endothelin antagonists, angiotensin II receptor antagonists and renin inhibitors that have been nitrosated through one or more sites such as oxygen (hydroxyl condensation), sulfur (sulfhydryl condensation), and/or nitrogen. The nitrosated compounds of the invention can be prepared using conventional methods known to one skilled in the art. For example, known methods for nitrosating compounds are described in U.S. Pat. Nos. 5,380,758 and 5,703,073; WO 97/27749; WO 98/19672; and Oae et al, Org. Prep. Proc. Int., 15(3):165–198 (1983), the disclosures of each of which are incorporated by reference herein in their entirety. WO 98/21193 discloses nitrosated ACE inhibitors and nitrosated beta-adrenergic blockers, the disclosure of which is incorporated by reference herein in its entirety. WO 99/00361 discloses nitrate salts of ACE inhibitors, the disclosure of which is incorporated by reference herein in its entirety.

In addition to the administration of the combination of nebivolol, optionally substituted with at least one NO and/or $NO_2$ group, and/or at least one metabolite of nebivolol, optionally substituted with at least one NO and/or $NO_2$ group, and at least one compound that donates, transfers or releases nitric oxide as a charged species, or elevates levels of endogenous EDRF or nitric oxide, or is a substrate for nitric oxide synthase and the antioxidant and/or the compound used to treat cardiovascular diseases, for the treatment of vascular diseases characterized by nitric oxide insufficiency, the patients can receive digitalis such as digoxin and/or diuretics.

The digoxin may preferably be administered orally to achieve a steady state blood serum concentration of at least about 0.7 nanograms per ml to about 2.0 nanograms per ml. The diuretic is administered, preferably orally, to manage edema. Suitable diuretics include, but are not limited to, thiazides (such as, for example, chlorothiazide, hydrochlorothiazide); ethacrynic acid, furosemide, spironalactone, triamterene or mixtures thereof. Depending on the diuretic used, potassium may also be administered to the patient in order to optimize the fluid balance while avoiding hypokalemic alkalosis. The administration of potassium can be as potassium chloride or by the daily ingestion of foods with high potassium content such as, for example, bananas, orange juice, and the like. The method of administration of these compounds is described in further detail in U.S. Pat. No. 4,868,179, the disclosure of which is incorporated by reference herein in its entirety.

The invention also provides methods of preventing and treating Raynaud's syndrome by administering a therapeutically effective amount of at least one nebivolol, optionally substituted with at least one NO and/or $NO_2$ group, and/or at least one metabolite of nebivolol, optionally substituted with at least one NO and/or $NO_2$ group, and, optionally, at least one compound that donates, transfers or releases nitric oxide as a charged species, or elevates levels of endogenous EDRF or nitric oxide, or is a substrate for nitric oxide synthase and/or at least one antioxidant or a pharmaceutically acceptable salt thereof, and/or at least one nitrosated compound used to treat cardiovascular diseases such as, for example, nitrosated angiotensin-converting enzyme inhibitor, nitrosated beta-adrenergic blocker, nitrosated cholesterol reducer, nitrosated calcium channel blocker, nitrosated endothelin antagonist, nitrosated angiotensin II receptor antagonist and/or nitrosated renin inhibitor. For example, the patient can be administered a therapeutically effective amount of at least one nitrosated and/or nitrosylated nebivolol of the invention. In another embodiment, the patient can be administered a therapeutically effective amount of at least one nitrosated and/or nitrosylated metabolite of nebivolol. In yet another embodiment, the patient can be administered a therapeutically effective amount of nebivolol, optionally substituted with at least one NO and/or $NO_2$ group, and/or at least one metabolite of nebivolol, optionally substituted with at least one NO and/or $NO_2$ group, and at least one compound that donates, transfers or releases nitric oxide as a charged species, or elevates levels of endogenous EDRF or nitric oxide, or is a substrate for nitric oxide synthase. In another embodiment, the patient can be administered a therapeutically effective amount of nebivolol, optionally substituted with at least one NO and/or $NO_2$ group, and/or at least one metabolite of nebivolol, optionally substituted with at least one NO and/or $NO_2$ group, and, optionally, at least one compound that donates, transfers or releases nitric oxide as a charged species, or elevates levels of endogenous EDRF or nitric oxide, or is a substrate for nitric oxide synthase and/or at least one antioxidant or a pharmaceutically acceptable salt thereof, and/or at least one nitrosated compound used to treat cardiovascular diseases. For example, the patient can be administered a nitrosated and/or nitrosylated nebivolol, a nitric oxide donor and an antioxidant, or the patient can be administered a nitrosated and/or nitrosylated metabolite of nebivolol, a nitric oxide donor and an antioxidant, or the patient can be administered nebivolol, a nitric oxide donor and an antioxidant. The nebivolol, nitric oxide donor, antioxidant and nitrosated compound used to treat cardiovascular diseases can be administered separately or as components of the same composition. Raynaud's syndrome is a condition that causes a loss of blood flow to the fingers, toes, nose and/or ears. The affected area turns white from the lack of circulation, then blue and cold, and finally numb. The affected area may also turn red, and may throb, tingle or swell.

In the methods of the invention nebivolol, optionally substituted with at least one NO and/or $NO_2$ group, the metabolites of nebivolol, optionally substituted with at least one NO and/or $NO_2$ group, and, optionally, nitric oxide donor, antioxidant and/or compound used to treat cardiovascular diseases, optionally substituted with at least one $NO_2$ group, can be administered as separate components or as components of the same composition. When the nebivolol, optionally substituted with at least one NO and/or $NO_2$ group, metabolite of nebivolol, optionally substituted with at least one NO and/or $NO_2$ group, and, optionally, nitric oxide donor, antioxidant, and/or compound used to treat cardiovascular diseases, optionally substituted with at least one $NO_2$ group, are administered as separate components for the treatment of vascular diseases characterized by nitric oxide insufficiency or Raynaud's syndrome, they are preferably administered to the patient at about the same time. "About the same time" includes after administering one compound (e.g., nebivolol or metabolite of nebivolol or nitric oxide donor or antioxidant or compound used to treat cardiovascular diseases) to the patient, the other compound (e.g., nitric oxide donor or antioxidant or compound used to treat cardiovascular diseases or nebivolol or metabolite of nebivolol) is administered to the patient. "About the same time" also includes simultaneous administration of the compounds or administering the compounds at the same time, at different times on the same day, or on different days, as long as they are administered as part of an overall treatment regimen.

Another embodiment of the invention provides compositions comprising nebivolol, optionally substituted with at least one NO and/or $NO_2$ group, and/or at least one metabolite of nebivolol, that are optionally nitrosated and/or nitrosylated, and, optionally, at least one compound that donates, transfers or releases nitric oxide and/or stimulates the endogenous production of NO or EDRF in vivo and/or is a substrate for nitric oxide synthase and/or at least one therapeutic agent and/or at least one nitrosated and/or nitrosylated therapeutic agent, bound to a matrix.

The nitrosated and/or nitrosylated nebivolol and/or nitrosated and/or nitrosylated metabolite of nebivolol and, optionally, NO donors and/or therapeutic agent and/or nitrosated and/or nitrosylated therapeutic agent, can be incorporated into a natural or synthetic matrix which can then be applied with specificity to a biological site of interest. Accordingly the optionally substituted nebivolol and/or metabolite of nebivolol, and, optionally, NO donor is "bound to the matrix" which means that the nitrosated and/or nitrosylated nebivolol and/or nitrosated and/or nitrosylated metabolite of nebivolol, and, optionally, NO donors and/or therapeutic agent and/or nitrosated and/or nitrosylated therapeutic agent, are physically and/or chemically associated with part of, incorporated with, attached to, or contained within the natural or synthetic matrix. In one embodiment, physical association or bonding can be achieved, for example, by coprecipitation of the nitrosated and/or nitrosylated nebivolol and/or nitrosated and/or nitrosylated metabolite of nebivolol, and, optionally, NO donor and/or therapeutic agent and/or nitrosated and/or nitrosylated therapeutic agent, with the matrix. In another embodiment, chemical association or bonding can be achieved by, for example, covalent bonding of a nucleophilic moiety of the nitrosated and/or nitrosylated nebivolol and/or nitrosated and/or nitrosylated metabolite of nebivolol, and, optionally, NO donor and/or therapeutic agent and/or nitrosated and/or nitrosylated therapeutic agent, to the matrix, such that nebivolol and/or metabolite of nebivolol is part of the matrix itself. In yet another embodiment, the nitrosated and/or nitrosylated nebivolol and/or nitrosated and/or nitrosylated metabolite of nebivolol, and, optionally, NO donor and/or therapeutic agent and/or nitrosated and/or nitrosylated therapeutic agent, can be incorporated into a porous layer of the matrix or into pores included in the natural or synthetic matrix. The manner in which the nitrosated and/or nitrosylated nebivolol and/or nitrosated and/or nitrosylated metabolite of nebivolol, and, optionally, NO donor and/or therapeutic agent and/or nitrosated and/or nitrosylated therapeutic agent, is associated, part of, attached to, incorporated with or contained within (i.e. "bound to") the matrix is inconsequential to the invention and all means of association, incorporation, attachment, and bonding are contemplated herein. Incorporation of the nitrosated and/or nitrosylated nebivolol and/or nitrosated and/or nitrosylated metabolite of nebivolol, and, optionally, NO donors and/or therapeutic agent and/or nitrosated and/or nitrosylated therapeutic agent, into the matrix results in site-specific application, thereby enhancing selectivity of action for the released nitric oxide and nebivolol and/or metabolite of nebivolol. Additionally, incorporation of the nitrosated and/or nitrosylated nebivolol and/or nitrosated and/or nitrosylated metabolite of nebivolol into the matrix reduces the rate of release of the nitric oxide and nebivolol and/or metabolite of nebivolol. This prolongs the release of the nitric oxide and nebivolol and/or metabolite of nebivolol thereby allowing for efficient dosing to achieve a desired biological effect so that the frequency of dosing can be reduced.

Any of a wide variety of natural or synthetic polymers can be used as the matrix in the context of the invention. It is only necessary for the matrix to be biologically acceptable. Exemplary matrixes suitable for use in the invention are polymers including, for example, polyolefins (such as polystyrene, polypropylene, polyethylene, high density polyethylene, polytetrafluorethylene, polyvinylidene diflouride and polyvinylchloride), polyethylenimine or derivatives thereof, polyethers (such as polyethylene glycol), polyesters (such as poly-L-lactic acid, poly-D, L-lactic, poly-D-lactic, polyglycolic, poly-(lactide/glycolide)), polyanhydrides, polyhydroxybutyrates, polyamides (such as nylon), polyurethanes, polyurethane copolymers (such as pellethane polymers), polyacrylates (such as polymethacrylate, poly (2-(methacryloyloxyethyl)-2'-(trimethylammonium)ethyl phosphate inner salt-co-n-dodecyl methacrylate), mixtures of polymers (such as polylactic acid/polylysine copolymers, polyurethane/polyester copolymers, polyurethane/polyether copolymers, nylon/polyether copolymers, such as vestamid), biopolymers (such as peptides, proteins, oligonucleotides, antibodies, peptide hormones, glycoproteins, glycogen and nucleic acids), starburst dendrimers, natural fibrous matrix (such as filter paper), synthetic fibrous matrix materials (such as three-dimensional lattice of synthetic polymers and copolymers) and the like. Exemplary polymers are described in U.S. Pat. Nos. 5,705,583, 5,770,645 and 5,994,444 and application Ser. No. 08/460,465, the disclosures of which are incorporated by reference herein in their entirety.

The physical and structural characteristics of the matrixes suitable for use in the invention are not critical, but depend on the application. It will be appreciated by one skilled in the art that where the matrix-nebivolol and/or matrix-metabolite of nebivolol composition of the invention is intended for local, relatively short term administration or similar administration they need not be biodegradable. For some uses, such as postangioplasty, coronary bypass surgery or intimal hyperplasia associated with vascular graft implants or the like, it may be desirable for the matrix to slowly dissolve in a physiological environment or to be biodegradable or bioresorbable.

The nitrosated and/or nitrosylated nebivolol and/or nitrosated and/or nitrosylated metabolite of nebivolol and/or nebivolol and, optionally, the compound that donates, transfers or releases nitric oxide and/or stimulates the endogenous production of NO or EDRF in vivo and/or is a substrate for nitric oxide synthase and/or therapeutic agent and/or nitrosated and/or nitrosylated therapeutic agent, bound to the matrix may be administered in a wide variety of forms or delivery means. Any delivery means should adequately protect the integrity of the nitric oxide prior to its release and should control the release of the nitric oxide at such a rate, in such an amount, and in such a location as to serve as an effective means for prevention and/or treatment of cardiovascular diseases or disorders, including restenosis. Delivery means for local administration include, for example, sutures, vascular implants, stents, heart valves, drug pumps, drug delivery catheters and the like. Delivery means for systemic administration include, for example, solutions, suspensions, emulsions, capsules, powders, sachets, tablets, effervescent tablets, topical patches, lozenges, aerosols, liposomes, microparticles, microspheres, beads and the like. The matrix itself may be structurally sufficient to serve as a delivery means.

The nitrosated and/or nitrosylated nebivolol and/or nitrosated and/or nitrosylated metabolite of nebivolol and/or nebivolol and, optionally, the compound that donates, transfers or releases nitric oxide and/or stimulates the endogenous production of NO or EDRF in vivo and/or is a substrate for nitric oxide synthase, and/or therapeutic agent and/or nitrosated and/or nitrosylated therapeutic agent, bound to the matrix can also be used to coat the surface of a medical device or instrument that comes into contact with blood (including blood components and blood products) or vascular tissue thereby rendering the surface passive. Alternatively the nitrosated and/or nitrosylated nebivolol and/or nitrosated and/or nitrosylated metabolite of nebivolol and/or nebivolol and the compound that donates, transfers or releases nitric oxide and/or stimulates the endogenous production of NO or EDRF in vivo and/or is a substrate for nitric oxide synthase, and/or therapeutic agent and/or nitrosated and/or nitrosylated therapeutic agent, bound to the matrix can also be used to coat the surface of a medical device or instrument that comes into contact with blood (including blood components and blood products) or vascular tissue thereby rendering the surface passive. U.S. Pat. Nos. 5,837,008, 5,665,077, 5,797,887 and 5,824,049, the disclosures of each of which are incorporated by reference herein in their entirety, describe methods for coating a surface of a medical device or instrument. Thus, for example, (i) all or a portion of the medical device may be coated with the nitrosated and/or nitrosylated nebivolol, and, optionally, NO donors and/or therapeutic agents and/or nitrosated and/or nitrosylated therapeutic agents, either as the coating per se or bound to a matrix, as described herein; or (ii) all or a portion of the medical device may be produced from a material which includes the nitrosated and/or nitrosylated nebivolol, and, optionally, NO donor, therapeutic agent and nitrosated and/or nitrosylated therapeutic agent, per se or bound to a matrix, as described herein.

It is also contemplated that artificial surfaces will vary depending on the nature of the surface, and such characteristics including contour, crystallinity, hydrophobicity, hydrophilicity, capacity for hydrogen bonding, and flexibility of the molecular backbone and polymers. Therefore, using routine methods, one of ordinary skill will be able to customize the coating technique by adjusting such parameters as the amount of adduct, length of treatment, temperature, diluents, and storage conditions, in order to provide optimal coating of each particular type of surface.

After the device or artificial material has been coated with the nitrosated and/or nitrosylated nebivolol and/or nitrosated and/or nitrosylated metabolite of nebivolol, and, optionally, NO donor, and/or therapeutic agent and/or nitrosated and/or nitrosylated therapeutic agent, or with nebivolol and/or metabolite of nebivolol and NO donor, and, optionally, therapeutic agent and/or nitrosated and/or nitrosylated therapeutic agent, it will be suitable for its intended use, including, for example, implantation as a heart valve, insertion as a catheter, insertion as a stent, or for cardiopulmonary oxygenation or hemodialysis.

Therapeutic agents useful in the invention include, but is not limited to, agents which biologically stent a vessel and/or reduce or inhibit vascular remodeling and/or inhibit or reduce vascular smooth muscle proliferation following a procedural vascular trauma. The "therapeutic agents" of the invention include agents that inhibit the cellular activity of a vascular smooth muscle cell, for example, proliferation, migration, increase in cell volume, increase in extracellular matrix synthesis (e.g., collagens, proteoglycans, and the like), or secretion of extracellular matrix materials by the cell. Suitable "therapeutic agents" include, but are not limited to, antithrombogenic agents (such as, for example, heparin, covalent heparin, hirudin, hirulog, coumadin, protamine, argatroban, D-phenylalanyl-L-poly-L-arginyl chloromethyl ketone, and the like); thrombolytic agents (such as, for example, urokinase, streptokinase, tissueplasminogen activators, and the like); fibrinolytic agents; vasospasm inhibitors; potassium channel activators (such as, for example, nicorandil, pinacidil, cromakalim, minoxidil, aprilkalim, loprazolam and the like); calcium channel blockers (such as, for example, nifedipine, veraparmil, diltiazem, gallopamil, niludipine, nimodipins, nicardipine, and the like); antihypertensive agents (such as, for example, HYTRIN®, and the like); antimicrobial agents or antibiotics (such as, for example, adriamycin, and the like); antiplatelet agents (such as, for example, aspirin, ticlopidine, a glycoprotein IIb/IIIa inhibitor, surface glycoprotein receptors and the like); antimitotic, antiproliferative agents or microtubule inhibitors (such as, for example, taxanes, colchicine, methotrexate, azathioprine, vincristine, vinblastine, cytochalasin, fluorouracil, adriamycin, mutamycin, tubercidin, epothilone A or B, discodermolide, and the like); antisecretory agents (such as, for example, retinoid, and the like); remodelling inhibitors; antisense nucleotides (such as, for example, deoxyribonucleic acid, and the like); anti-cancer agents (such as, for example, tamoxifen citrate, acivicin, bizelesin, daunorubicin, epirubicin, mitoxantrone, and the like); steroids (such as, for example, dexamethasone, dexamethasone sodium phosphate, dexamethasone acetate, and the like); non-steroidal antiinflammatory agents (NSAID); COX-2 inhibitors; immunosuppressive agents (such as, for example cyclosporin, rapamycin, everolimus, actinomycin D and the like); growth factor antagonists or antibodies (such as, for example, trapidal (a PDGF antagonist), angiopeptin (a growth hormone antagonist), angiogenin, and the like); dopamine agonists (such as, for example, apomorphine, bromocriptine, testosterone, cocaine, strychnine, and the like); radiotherapeutic agents (such as, for example, $^{60}$Co (5.3 year half life), $^{192}$Ir (73.8 days), $^{32}$P (14.3 days), $^{111}$In (68 hours), $^{90}$Y (64 hours), $^{99m}$Tc (6 hours), and the like); heavy metals functioning as radiopaque agents (such as, for example, iodine-containing compounds, barium-containing compounds, gold, tantalum, platinum, tungsten, and the like); biologic agents (such as, for example, peptides, proteins, enzymes, extracellular matrix components, cellular components, and the like); angiotensin converting enzyme (ACE) inhibitors; angiotensin II receptor antagonists; renin inhibitiors; free radical scavengers, iron chelators or antioxidants (such as, for example, ascorbic acid, alpha tocopherol, superoxide dismutase, deferoxamine, 21-aminosteroid, and the like); sex hormones (such as, for example, estrogen, and the like); antipolymerases (such as, for example, AZT, and the like); antiviral agents (such as, for example, acyclovir, famciclovir, rimantadine hydrochloride, ganciclovir sodium, Norvir®, Crixivan®, and the like); photodynamic therapy agents (such as, for example, 5-aminolevulinic acid, meta-tetrahydroxyphenylchlorin, hexadecafluoro zinc phthalocyanine, tetramethyl hematoporphyrin, rhodamine 123, and the like); antibody targeted therapy agents (such as, for example, IgG2 Kappa antibodies against *Pseudomonas aeruginosa* exotoxin A and reactive with A431 epidermoid carcinoma cells, monoclonal antibody against the noradrenergic enzyme dopamine beta-hydroxylase conjugated to saporin, and the like); and gene therapy agent. Preferred therapeutic agents, include antiproliferative agents, such as, for example, taxanes; steroids such as, for example, dexamethasone, immunosuppressive agents, such as for example, rapamycin, everolimus, actinomycin D and the like. The therapeutic agent can optionally be substituted with at least one NO and/or $NO_2$ group (i.e., nitrosylated and/or nitrosated) through one or more sites such as oxygen (hydroxyl condensation), sulfur (sulfhydryl condensation), and/or nitrogen. The compounds and compositions of the invention can also be administered in combination with other medications used for the treatment of these diseases or disorders.

Suitable taxanes, include, but are not limited to, for example, paclitaxel and docetaxel, water soluble compositions of paclitaxel and docetaxel, pro-drugs of paclitaxel and docetaxel, as well as functional analogs, equivalents or derivatives of taxanes, and the like. For example, derivatives and analogs of taxanes include, but are not limited to, baccatin III, 10-deacetyltaxol, 7-xylosyl-10-deacetyltaxol, cephalomannine, 10-deacetyl-7-epitaxol, 7-epitaxol, 10-deacetylbaccatin III, 10-deacetylcephaolmannine and analogs or derivatives, and the like. Taxanes are disclosed in, for example, U.S. Pat. Nos. 4,960,790, 5,157,049, 5,284,864, 5,399,726, 5,550,261, 5,616,608, 5,629,433, 5,646,176, 5,688,977, 5,703,117, 5,760,072, 5,808,113, 5,912,263, 5,919,815, 5,965,739, 5,977,163, 5,981,564, 5,998,656, 6,017,935, 6,017,948, 6,028,205 and in WO 93/17121, WO 94/15599, WO 95/20582, WO 96/00724, WO 96/40091, WO 97/10234, WO 97/19938, WO 97/32578, WO 97/33552, WO 98/00419, WO 98/28288, WO 98/37765, WO 98/38862, WO 99/14209, WO 99/49901, WO 99/57105, WO 00/10988 and in EP 0 558 959 B1, EP 0 624 377 A2, EP 0 639 577 A1, the disclosures of each of which are incorporated by reference herein in their entirety. Taxanes and their nitrosating and/or nitrosylated derivatives are also disclosed in U.S. application Ser. No. 09/886,494, assigned to NitroMed Inc.; and in WO 00/61537, WO 00/61541 and WO 01/12584; the disclosure of each of which are incorporated by reference herein in its entirety.

Suitable anticoagulants include, but are not limited to, heparin, coumarin, aspirin, protamine, warfarin, dicumarol, phenprocoumon, indan-1,3-dione, acenocoumarol, ansindione, and the like. Suitable anticoagulants are described more fully in the literature, such as in Goodman and Gilman, The Pharmacological Basis of Therapeutics (9th Edition), McGraw-Hill, 1995, Pgs. 1341–1359; the Merck Index on CD-ROM, Twelfth Edition, Version 12:1, 1996; STN express file reg and file phar.

Another embodiment of the invention provides methods for the prevention of platelet aggregation and platelet adhesion caused by the exposure of blood (including blood components or blood products) to a medical device or instrument by incorporating at least one nitrosated and/or nitrosylated nebivolol and/or nitrosated and/or nitrosylated metabolite of nebivolol and/or nebivolol, and, optionally, at least one compound that donates, transfers or releases nitric oxide and/or stimulates the endogenous production of NO or EDRF in vivo and/or is a substrate for nitric oxide synthase, and/or therapeutic agent and/or nitrosated and/or nitrosylated therapeutic agent, capable of releasing a therapeutically effective amount of nitric oxide, into and/or on the portion(s) of the medical device that come into contact with blood (including blood components or blood products) or vascular tissue. The nitrosated and/or nitrosylated nebivolol and/or nitrosated and/or nitrosylated metabolite of nebivolol and/or nebivolol, and, optionally, NO donors, therapeutic agents and/or nitrosated and/or nitrosylated therapeutic agents, may be directly or indirectly linked to the natural or synthetic polymeric material from which all or a portion of the device is made, as disclosed in U.S. Pat. Nos. 6,087,479 and 6,174,539, assigned to NitroMed, the disclosure of each of which are incorporated by reference herein in its entirety. Alternatively, the nitrosated and/or nitrosylated nebivolol, and/or nitrosated and/or nitrosylated metabolite of nebivolol and/or nebivolol, and, optionally, NO donors, therapeutic agents and/or nitrosated and/or nitrosylated therapeutic agents, may be incorporated into the body of the device that is formed of a biodegradable or bioresorbable material, including the matrix described herein. Thus the nitric oxide is released over a sustained period of the resorption or degradation of the body of the device.

Another embodiment of the invention relates to local administration of the nitrosated and/or nitrosylated nebivolol and/or nitrosated and/or nitrosylated metabolite of nebivolol and/or nebivolol, and, optionally, at least one compound that donates, transfers or releases nitric oxide and/or stimulates the endogenous production of NO or EDRF in vivo and/or is a substrate for nitric oxide synthase, and/or at least one therapeutic agent and/or at least one nitrosated and/or nitrosylated therapeutic agent, to the site of injured or damaged tissue (e.g., damaged blood vessels) for the treatment of the injured or damaged tissue. Such damage may result from the use of a medical device in an invasive procedure. Thus, for example, in treating blocked vasculature by, for example, angioplasty, damage can result to the blood vessel. Such damage may be treated by use of the compounds and compositions described herein. In addition to repair of the damaged tissue, such treatment can also be used to prevent and/or alleviate and/or delay re-occlusions, for example, restenosis. The compounds and compositions can be locally delivered using any of the methods known to one skilled in the art, including but not limited to, a drug delivery catheter, an infusion catheter, a drug delivery guidewire, an implantable medical device, and the like. In one embodiment, all or most of the damaged area is coated with the nitrosated and/or nitrosylated nebivolol described herein per se or in a pharmaceutically acceptable carrier or excipient which serves as a coating matrix, including the matrix described herein. This coating matrix can be of a liquid, gel or semisolid consistency. The carrier or matrix can be made of or include agents which provide for metered or sustained release of the therapeutic agents.

In preventing and/or treating cardiovascular diseases or disorders, the nitrosated and/or nitrosylated nebivolol and/or nitrosated and/or nitrosylated metabolite of nebivolol and/or nebivolol, and, optionally, at least one compound that donates, transfers or releases nitric oxide and/or stimulates the endogenous production of NO or EDRF in vivo and/or is a substrate for nitric oxide synthase and/or at least one therapeutic agent and/or at least one nitrosated and/or nitrosylated therapeutic agent, can be administered directly to the damaged vascular surface intravenously by using an intraarterial or intravenous catheter, suitable for delivery of the compounds to the desired location. The location of damaged arterial surfaces is determined by conventional diagnostic methods, such as X-ray angiography, performed using routine and well-known methods available to one skilled in the art. In addition, administration of the nitrosated and/or nitrosylated nebivolol, and/or nitrosated and/or nitrosylated metabolite of nebivolol and/or nebivolol, and, optionally, NO donors, therapeutic agents and/or nitrosated and/or nitrosylated therapeutic agents, using an intraarterial or intravenous catheter is performed using routine methods well known to one skilled in the art. Typically, the compound or composition is delivered to the site of angioplasty through the same catheter used for the primary procedure, usually introduced to the carotid or coronary artery at the time of angioplasty balloon inflation. The nitrosated and/or nitrosylated nebivolol and/or nitrosated and/or nitrosylated metabolite of nebivolol and/or nebivolol, and, optionally, NO donors, therapeutic agents and nitrosated and/or nitrosylated therapeutic agents, slowly decompose at body temperature over a prolonged period of time releasing nitric oxide at a rate effective to prevent and/or treat cardiovascular diseases or disorders including, for example, restenosis.

When administered in vivo, the compounds and compositions of the invention can be administered in combination with pharmaceutically acceptable carriers and in dosages described herein. When the compounds and compositions of the invention are administered as a mixture of at least one nitrosated and/or nitrosylated nebivolol or at least one nitrosated and/or nitrosylated metabolite of nebivolol or nebivolol or at least one metabolite of nebivolol and at least one nitric oxide donor, or at least one therapeutic agent or at least one nitrosated and/or nitrosylated therapeutic agent, they can also be used in combination with one or more additional therapeutic agents which are known to be effective against the specific disease state targeted for treatment. The nitric oxide donors and/or therapeutic agents can be administered simultaneously with, subsequently to, or prior to administration of nebivolol, including those that are substituted with one or more NO and/or $NO_2$ groups, and/or other additional compounds.

The compounds and compositions of the invention can be administered by any available and effective delivery system including, but not limited to, orally, bucally, parenterally, by inhalation spray, by topical application, by injection, transdermally, or rectally (e.g., by the use of suppositories) in dosage unit formulations containing conventional nontoxic pharmaceutically acceptable carriers, adjuvants, and vehicles, as desired. Parenteral includes subcutaneous injections, intravenous, intramuscular, intrasternal injection, or infusion techniques.

Topical compound administration, which is known to one skilled in the art, involves the delivery of pharmaceutical compounds via percutaneous passage of the compound into the systemic circulation of the patient. Topical administration can also involve the use of transdermal administration such as transdermal patches or iontophoresis devices. Other components can be incorporated into the transdermal patches as well. For example, compositions and/or transdermal patches can be formulated with one or more preservatives or bacteriostatic agents including, but not limited to, methyl hydroxybenzoate, propyl hydroxybenzoate, chlorocresol, benzalkonium chloride, and the like. Dosage forms for topical administration of the compounds and compositions can include creams, pastes, sprays, lotions, gels, ointments, eye drops, nose drops, ear drops, and the like. In such dosage forms, the compositions of the invention can be mixed to form white, smooth, homogeneous, opaque cream or lotion with, for example, benzyl alcohol 1% or 2% (wt/wt) as a preservative, emulsifying wax, glycerin, isopropyl palmitate, lactic acid, purified water and sorbitol solution. In addition, the compositions can contain polyethylene glycol 400. They can be mixed to form ointments with, for example, benzyl alcohol 2% (wt/wt) as preservative, white petrolatum, emulsifying wax, and tenox II (butylated hydroxyanisole, propyl gallate, citric acid, propylene glycol). Woven pads or rolls of bandaging material, e.g., gauze, can be impregnated with the compositions in solution, lotion, cream, ointment or other such form can also be used for topical application. The compositions can also be applied topically using a transdermal system, such as one of an acrylic-based polymer adhesive with a resinous crosslinking agent impregnated with the composition and laminated to an impermeable backing.

Solid dosage forms for oral administration can include capsules, tablets, effervescent tablets, sustain release tablets, sustain release capsules, chewable tablets, pills, powders, sachets, granules and gels. In such solid dosage forms, the active compounds can be admixed with at least one inert diluent such as sucrose, lactose or starch. Such dosage forms can also comprise, as in normal practice, additional substances other than inert diluents, e.g., lubricating agents such as magnesium stearate. In the case of capsules, tablets, effervescent tablets, and pills, the dosage forms can also comprise buffering agents. Soft gelatin capsules can be prepared to contain a mixture of the active compounds or compositions of the invention and vegetable oil. Hard gelatin capsules can contain granules of the active compound in combination with a solid, pulverulent carrier such as lactose, saccharose, sorbitol, mannitol, potato starch, corn starch, amylopectin, cellulose derivatives of gelatin. Tablets and pills can be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

Suppositories for vaginal or rectal administration of the compounds and compositions of the invention can be prepared by mixing the compounds or compositions with a suitable nonirritating excipient such as cocoa butter and polyethylene glycols which are solid at room temperature but liquid at body temperature, such that they will melt and release the drug.

Injectable preparations, for example, sterile injectable aqueous or oleaginous suspensions can be formulated according to the known art using suitable dispersing agents, wetting agents and/or suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be used are water, Ringer's solution, and isotonic sodium chloride solution. Sterile fixed oils are also conventionally used as a solvent or suspending medium.

The compositions of this invention can further include conventional excipients, i.e., pharmaceutically acceptable organic or inorganic carrier substances suitable for parenteral application which do not deleteriously react with the active compounds. Suitable pharmaceutically acceptable carriers include, for example, water, salt solutions, alcohol, vegetable oils, polyethylene glycols, gelatin, lactose, amylose, magnesium stearate, talc, surfactants, silicic acid, viscous paraffin, perfume oil, fatty acid monoglycerides and diglycerides, petroethral fatty acid esters, hydroxymethylcellulose, polyvinylpyrrolidone, and the like. The pharmaceutical preparations can be sterilized and if desired, mixed with auxiliary agents, e.g., lubricants, preservatives, stabilizers, wetting agents, emulsifiers, salts for influencing osmotic pressure, buffers, colorings, flavoring and/or aromatic substances and the like which do not deleteriously react with the active compounds. For parenteral application, particularly suitable vehicles consist of solutions, preferably oily or aqueous solutions, as well as suspensions, emulsions, or implants. Aqueous suspensions may contain substances that increase the viscosity of the suspension and include, for example, sodium carboxymethyl cellulose, sorbitol and/or dextran. Optionally, the suspension may also contain stabilizers.

Solvents useful in the practice of this invention include pharmaceutically acceptable, water-miscible, non-aqueous solvents. In the context of this invention, these solvents should be taken to include solvents that are generally acceptable for pharmaceutical use, substantially water-miscible, and substantially non-aqueous. Preferably, these solvents are also non-phthalate plasticizer leaching solvents, so that, when used in medical equipment, they substantially do not leach phthalate plasticizers that may be present in the medical equipment. More preferably, the pharmaceutically-acceptable, water-miscible, non-aqueous solvents usable in the practice of this invention include, but are not limited to, N-methyl pyrrolidone (NMP); propylene glycol; ethyl acetate; dimethyl sulfoxide; dimethyl acetamide; benzyl alcohol; 2-pyrrolidone; benzyl benzoate; $C_{2-6}$ alkanols; 2-ethoxyethanol; alkyl esters such as 2-ethoxyethyl acetate, methyl acetate, ethyl acetate, ethylene glycol diethyl ether, or ethylene glycol dimethyl ether; (S)-(−)-ethyl lactate; acetone; glycerol; alkyl ketones such as methylethyl ketone or dimethyl sulfone; tetrahydrofuran; cyclic alkyl amides such as caprolactam; decylmethylsulfoxide; oleic acid; aromatic amines such as N,N-diethyl-m-toluamide; or 1-dodecylazacycloheptan-2-one.

The most preferred pharmaceutically-acceptable, water-miscible, non-aqueous solvents are N-methylpyrrolidone (NMP), propylene glycol, ethyl acetate, dimethyl sulfoxide, dimethyl acetamide, benzyl alcohol, 2-pyrrolidone, or benzyl benzoate. Ethanol may also be used as a pharmaceutically-acceptable, water-miscible, non-aqueous solvent according to the invention, despite its negative impact on stability. Additionally, triacetin may also be used as a pharmaceutically-acceptable, water-miscible, non-aqueous solvent, as well as functioning as a solubilizer in certain circumstances. NMP may be available as PHARMA-SOLVE® from International Specialty Products (Wayne, N.J.). Benzyl alcohol may be available from J. T. Baker, Inc. Ethanol may be available from Spectrum, Inc. Triacetin may be available from Mallinkrodt, Inc.

The compositions of this invention can further include solubilizers. Solubilization is a phenomenon that enables the formation of a solution. It is related to the presence of amphiphiles, that is, those molecules that have the dual properties of being both polar and non-polar in the solution that have the ability to increase the solubility of materials that are normally insoluble or only slightly soluble, in the dispersion medium. Solubilizers often have surfactant properties. Their function may be to enhance the solubility of a solute in a solution, rather than acting as a solvent, although in exceptional circumstances, a single compound may have both solubilizing and solvent characteristics. Solubilizers useful in the practice of this invention include, but are not limited to, triacetin, polyethylene glycols (such as, for example, PEG 300, PEG 400, or their blend with 3350, and the like), polysorbates (such as, for example, Polysorbate 20, Polysorbate 40, Polysorbate 60, Polysorbate 65, Polysorbate 80, and the like), poloxamers (such as, for example, Poloxamer 124, Poloxamer 188, Poloxamer 237, Poloxamer 338, Poloxamer 407, and the like), polyoxyethylene ethers (such as, for example, Polyoxyl 2 cetyl ether, Polyoxyl 10 cetyl ether, and Polyoxyl 20 cetyl ether, Polyoxyl 4 lauryl ether, Polyoxyl 23 lauryl ether, Polyoxyl 2 oleyl ether, Polyoxyl 10 oleyl ether, Polyoxyl 20 oleyl ether, Polyoxyl 2 stearyl ether, Polyoxyl 10 stearyl ether, Polyoxyl 20 stearyl ether, Polyoxyl 100 stearyl ether, and the like), polyoxylstearates (such as, for example, Polyoxyl 30 stearate, Polyoxyl 40 stearate, Polyoxyl 50 stearate, Polyoxyl 100 stearate, and the like), polyethoxylated stearates (such as, for example, polyethoxylated 12-hydroxy stearate, and the like), and Tributyrin.

Other materials that may be added to the compositions of the invention include cyclodextrins, and cyclodextrin analogs and derivatives, and other soluble excipients that could enhance the stability of the inventive composition, maintain the product in solution, or prevent side effects associated with the administration of the inventive composition. Cyclodextrins may be available as ENCAPSIN® from Janssen Pharmaceuticals.

The composition, if desired, can also contain minor amounts of wetting agents, emulsifying agents and/or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, magnesium carbonate, and the like.

Various delivery systems are known and can be used to administer the compounds or compositions of the invention, including, for example, encapsulation in liposomes, microbubbles, emulsions, microparticles, microcapsules, nanoparticles, and the like. The required dosage can be administered as a single unit or in a sustained release form.

The bioavailabilty of the compositions can be enhanced by micronization of the formulations using conventional techniques such as grinding, milling, spray drying and the like in the presence of suitable excipients or agents such as phospholipids or surfactants.

Sustained release dosage forms of the invention may comprise microparticles and/or nanoparticles having a therapeutic agent dispersed therein or may comprise the therapeutic agent in pure, preferably crystalline, solid form. For sustained release administration, microparticle dosage forms comprising pure, preferably crystalline, therapeutic agents are preferred. The therapeutic dosage forms of this aspect of the invention may be of any configuration suitable for sustained release. Preferred sustained release therapeutic dosage forms exhibit one or more of the following characteristics: microparticles (e.g., from about 0.5 micrometers to about 100 micrometers in diameter, preferably about 0.5 to about 2 micrometers; or from about 0.01 micrometers to about 200 micrometers in diameter, preferably from about 0.5 to about 50 micrometers, and more preferably from about 2 to about 15 micrometers) or nanoparticles (e.g., from about 1.0 nanometer to about 1000 nanometers in diameter, preferably about 50 to about 250 nanometers; or from about 0.01 nanometer to about 1000 nanometers in diameter, preferably from about 50 to about 200 nanometers), free flowing powder structure; biodegradable structure designed to biodegrade over a period of time between from about 0.5 to about 180 days, preferably from about 1 to 3 to about 150 days, more preferably from about 3 to about 180 days, and most preferably from about 10 to about 21 days; or non-biodegradable structure to allow the therapeutic agent diffusion to occur over a time period of between from about 0.5 to about 180 days, more preferably from about 30 to about 120 days; or from about 3 to about 180 days, more preferably from about 10 to about 21 days; biocompatible with target tissue and the local physiological environment into which the dosage form to be administered, including yielding biocompatible biodegradation products; facilitate a stable and reproducible dispersion of therapeutic agent therein, preferably to form a therapeutic agent-polymer matrix, with active therapeutic agent release occurring by one or both of the following routes: (1) diffusion of the therapeutic agent through the dosage form (when the therapeutic agent is soluble in the shaped polymer or polymer mixture defining the dimensions of the dosage form); or (2) release of the therapeutic agent as the dosage form biodegrades; and/or for targeted dosage forms, capability to have, preferably, from about 1 to about 10,000 binding protein/peptide to dosage form bonds and more preferably, a maximum of about 1 binding peptide to dosage form bond per 150 square angstroms of particle surface area. The total number of binding protein/peptide to dosage form bonds depends upon the particle size used. The binding proteins or peptides are capable of coupling to the particles of the therapeutic dosage form through covalent ligand sandwich or non-covalent modalities as set forth herein.

Nanoparticle sustained release therapeutic dosage forms are preferably biodegradable and, optionally, bind to the vascular smooth muscle cells and enter those cells, primarily by endocytosis. The biodegradation of the nanoparticles occurs over time (e.g., 30 to 120 days; or 10 to 21 days) in prelysosomic vesicles and lysosomes. Preferred larger microparticle therapeutic dosage forms of the invention release the therapeutic agents for subsequent target cell uptake with only a few of the smaller microparticles entering the cell by phagocytosis. A practitioner in the art will appreciate that the precise mechanism by which a target cell assimilates and metabolizes a dosage form of the invention depends on the morphology, physiology and metabolic processes of those cells. The size of the particle sustained release therapeutic dosage forms is also important with respect to the mode of cellular assimilation. For example, the smaller nanoparticles can flow with the interstitial fluid between cells and penetrate the infused tissue. The larger microparticles tend to be more easily trapped interstitially in the infused primary tissue, and thus are useful to deliver anti-proliferative therapeutic agents.

Preferred sustained release dosage forms of the invention comprise biodegradable microparticles or nanoparticles. More preferably, biodegradable microparticles or nanoparticles are formed of a polymer containing matrix that biodegrades by random, nonenzymatic, hydrolytic scissioning to release therapeutic agent, thereby forming pores within the particulate structure.

The compounds and compositions of the invention can be formulated as pharmaceutically acceptable salts. Pharmaceutically acceptable salts include, for example, alkali metal salts and addition salts of free acids or free bases. The nature of the salt is not critical, provided that it is pharmaceutically-acceptable. Suitable pharmaceutically-acceptable acid addition salts may be prepared from an inorganic acid or from an organic acid. Examples of such inorganic acids include, but are not limited to, hydrochloric, hydrobromic, hydroiodic, nitrous (nitrite salt), nitric (nitrate salt), carbonic, sulfuric, phosphoric acid, and the like. Appropriate organic acids include, but are not limited to, aliphatic, cycloaliphatic, aromatic, heterocyclic, carboxylic and sulfonic classes of organic acids, such as, for example, formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, algenic, β-hydroxybutyric, cyclohexylaminosulfonic, galactaric and galacturonic acid and the like. Suitable pharmaceutically-acceptable base addition salts include, but are not limited to, metallic salts made from aluminum, calcium, lithium, magnesium, potassium, sodium and zinc or organic salts made from primary, secondary and tertiary amines, cyclic amines, N,N'-dibenzylethylenediamine, chloroprocaine, choline, diethanolamine, ethylenediamine, meglumine (N-methylglucamine) and procaine and the like. All of these salts may be prepared by conventional means from the corresponding compound by reacting, for example, the appropriate acid or base with the compound.

While individual needs may vary, determination of optimal ranges for effective amounts of the compounds and/or compositions is within the skill of the art. Generally, the dosage required to provide an effective amount of the compounds and compositions, which can be adjusted by one of ordinary skill in the art, will vary depending on the age, health, physical condition, sex, diet, weight, extent of the dysfunction of the recipient, frequency of treatment and the nature and scope of the dysfunction or disease, medical condition of the patient, the route of administration, pharmacological considerations such as the activity, efficacy, pharmacokinetic and toxicology profiles of the particular compound used, whether a drug delivery system is used, and whether the compound is administered as part of a drug combination.

The usual doses of nebivolol (including nitrosated and/or nitrosylated nebivolol, nitrosated and/or nitrosylated metabolites of nebivolol, and metabolites of nebivolol) for the treating and/or preventing vascular diseases characterized by nitric oxide insufficiency; and for treating and/or preventing Raynaud's syndrome is approximately 0.1 mg to about 10 mg per day, preferably about 5 mg per day, administered as a single dose once a day; in multiple doses several times throughout the day; or in a sustained-release formulation or as a transdermal patch.

The doses of nitric oxide donors in the pharmaceutical composition will be dependent on the specific nitric oxide donor compound and the mode of administration. For example, when isosorbide dinitrate is the orally administered nitric oxide donor, it can be administered in an amount of about 5 milligrams per day to about 200 milligrams per day. In a more particular embodiment, the isosorbide dinitrate can be administered in an amount of about 20 milligrams per day to about 160 milligrams per day. In an even more particular embodiment, the isosorbide dinitrate can be administered in an amount of about 40 milligrams one to four times per day. When isosorbide mononitrate is the orally administered nitric oxide donor, it can be administered in an amount of about 5 milligrams per day to about 120 milligrams per day. In a more particular embodiment, the isosorbide mononitrate can be administered in an amount of about 15 milligrams per day to about 100 milligrams per day. In an even more particular embodiment, the isosorbide mononitrate can be administered in an amount of about 20 milligrams one to four times per day. The particular amounts of isosorbide dinitrate and/or isosorbide mononitrate can be administered as a single dose once a day; or in multiple doses several times throughout the day; or as a sustained-release oral formulation; or as a transdermal sustained release patch.

The dose of nitric oxide donor in the composition will be dependent on the specific nitric oxide donor compound and the mode of administration. For example, when L-arginine is the orally administered nitric oxide donor, it can be administered in an amount of about 3 grams to about 15 grams to provide a plasma level in the range of about 0.2 mM to about 30 mM.

The doses of the antioxidant in the pharmaceutical composition will be dependent on the specific antioxidant compound and the mode of administration. For example when hydralazine is the administered antioxidant, it can be administered in an amount of about 30 milligrams per day to about 400 milligrams per day. In a more particular embodiment, the hydralazine hydrochloride can be administered in an amount of about 50 milligrams per day to about 300 milligrams per day. In an even more particular embodiment, the hydralazine hydrochloride can be administered in an amount of about 75 milligrams once to four times per day. The particular amounts of hydralazine can be administered as a single dose once a day; or in multiple doses several times throughout the day; or as a sustained-release oral formulation; or as a transdermal sustained release patch.

The nitrosated and/or nitrosylated nebivolol and/or nitrosated and/or nitrosylated metabolites of nebivolol of the invention are used at dose ranges and over a course of dose regimen and are administered in the same or substantially equivalent vehicles/carrier by the same or substantially equivalent as their non-nitrosated/nitrosylated counterparts. The nitrosated and/or nitrosylated compounds of the invention can also be used in lower doses and in less extensive regimens of treatment. The amount of active ingredient that can be combined with the carrier materials to produce a single dosage form will vary depending upon the host treated and the particular mode of administration, and is within the skill in the art.

The invention also provides pharmaceutical kits comprising one or more containers filled with one or more of the ingredients of the pharmaceutical compounds and/or compositions of the invention, including, nebivolol, optionally substituted with at least one NO and/or NO$_2$ group, one or more metabolites of nebivolol, optionally substituted with one or more NO and/or NO$_2$ groups, and one or more of the NO donors, and one or more antioxidants described herein. Such kits can also include, for example, other compounds and/or compositions (e.g., diuretics, digoxin, compounds used to treat cardiovascular diseases, therapeutic agents, permeation enhancers, lubricants, and the like), a device(s) for administering the compounds and/or compositions, and written instructions in a form prescribed by a governmental agency regulating the manufacture, use or sale of pharmaceuticals or biological products, which instructions can also reflects approval by the agency of manufacture, use or sale for human administration.

The disclosure of each patent, patent application and publication cited or described in the specification is hereby incorporated by reference herein in its entirety.

Although the invention has been set forth in detail, one skilled in the art will appreciate that numerous changes and modifications may be made without departing from the spirit and scope of the invention.

What is claimed is:

1. A compound of Formula (I), Formula (IV) or Formula (V), a stereoisomer thereof or a pharmaceutically acceptable salt thereof:

wherein the compound of Formula (I) is:

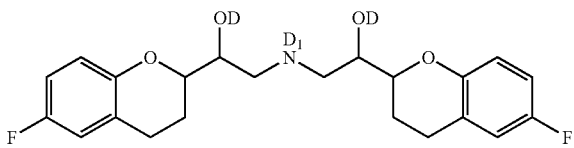

wherein:
D is hydrogen, Q, K or $R_5$;
$R_5$ is:

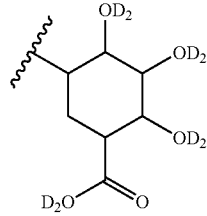

$D_1$ is hydrogen or $R_5$;
$D_2$ is hydrogen, Q or K;
Q is —NO or —$NO_2$;
K is —$W_a$-$E_b$-$(C(R_e)(R_f))_p$-$E_c$-$(C(R_e)(R_f))_x$—$W_d$—$(C(R_e)(R_f))_y$—$W_i$-$E_j$-$W_g$—$(C(R_e)(R_f))_z$-T-Q;
a, b, c, d, g, i and j are each independently an integer from 0 to 3;
p, x, y and z are each independently an integer from 0 to 10;
W at each occurrence is independently —C(O)—, —C(S)—, -T-, —$(C(R_e)(R_f))_h$—, an alkyl group, an aryl group, a heterocyclic ring, an arylheterocyclic ring, or —$(CH_2CH_2O)_q$—;
E at each occurrence is independently -T-, an alkyl group, an aryl group, —$(C(R_e)(R_f))_h$—, a heterocyclic ring, an arylheterocyclic ring, or —$(CH_2CH_2O)_q$—;
h is an integer form 1 to 10;
q is an integer from 1 to 5;
$R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, an alkylcycloalkyl, an alkylheterocyclic ring, a cycloalkylalkyl, a cycloalkylthio, a cycloalkenyl, an heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cyano an aminoalkyl, an aminoaryl, an aryl, an arylalkyl, an alkylaryl, a carboxamido, a alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, an alkylsulfonyl, an alkylsulfonyloxy, an arylsulfonyl, arylsulphonyloxy, a sulfonic ester, a urea, a phosphoryl, a nitro, $W_h$, -T-Q, or —$(C(R_e)(R_f))_k$-T-Q, or $R_e$ and $R_f$ taken together with the carbons to which they are attached form a carbonyl, a methanthial, a heterocyclic ring, a cycloalkyl group, an aryl group, an oxime or a bridged cycloalkyl group;
k is an integer from 1 to 3;
T at each occurrence is independently a covalent bond, a carbonyl, an oxygen, —$S(O)_o$— or —$N(R_a)R_i$—;
o is an integer from 0 to 2;
$R_a$ is a lone pair of electrons, a hydrogen or an alkyl group;
$R_i$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylaryl, an alkylsulfinyl, an alkylsulfonyl, an alkylsulfonyloxy, an arylsulfinyl, an arylsulfonyl, arylsulphonyloxy, a sulfonamido, a carboxamido, a carboxylic ester, an aminoalkyl, an aminoaryl, —$CH_2$—$C(T-Q)(R_e)(R_f)$, a bond to an adjacent atom creating a double bond to that atom, —$(N_2O_2$—$)^-$•$M^+$, wherein $M^+$ is an organic or inorganic cation;
with the proviso that the compound of Formula (I) must contain at least one nitrite, nitrate, thionitrite or thionitrate group;
wherein the compounds of Formula (IV) and Formula (V) are:

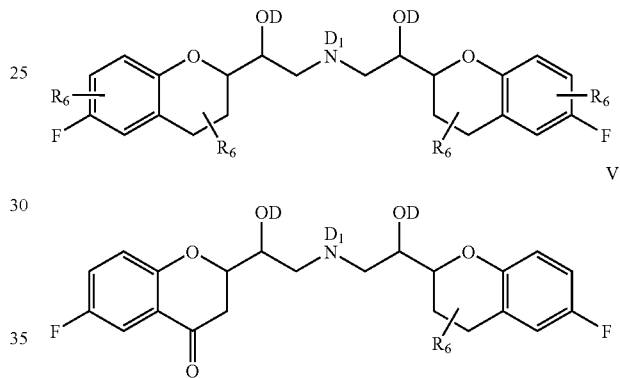

wherein:
$R_6$ at each occurrence is independently a hydrogen, a hydroxy or —OD;
D and $D_1$ are as defined herein; and
with the proviso that the compounds of Formula (IV) and Formula (V), must contain at least one nitrite, nitrate, thionitrite or thionitrate group.

2. The compound of claim 1, wherein the compound of Formula (I) is a nitrosated nebivolol, a nitrosylated nebivolol, or a nitrosated and nitrosylated nebivolol, wherein the compounds of Formula (IV) and Formula (V) are a nitrosated metabolite of nebivolol, a nitrosylated metabolite of nebivolol, or a nitrosated and nitrosylated metabolite of nebivolol.

3. A composition comprising the compound of claim 1 and a pharmaceutically acceptable carrier.

4. A method of treating hypertension in a patient in need thereof comprising administering a therapeutically effective amount of the composition of claim 3.

5. The method of claim 4, wherein the composition is administered intravenously, orally, bucally, parenterally, by an inhalation spray, by topical application or transdermally.

6. A composition comprising at least one compound of Formula (I), Formula (IV) or Formula (V), or an isomer thereof, or a pharmaceutically acceptable salt thereof, bound to a matrix;
wherein the matrix is a polymer, a fiber, or a mixture thereof; and
wherein the compound of Formula (I) is:

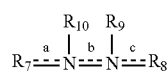

(VI)

wherein:
D is hydrogen, Q, K or $R_5$;
$R_5$ is:

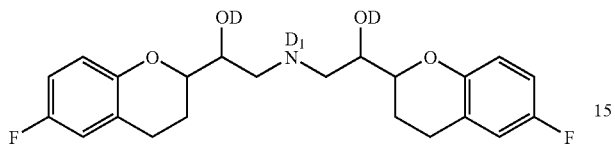

I $D_1$ is hydrogen or $R_5$;
$D_2$ is hydrogen, Q or K;
Q is —NO or —$NO_2$;
K is —$W_a$-$E_b$-(C($R_e$)($R_f$))$_p$-$E_c$-(C($R_e$)($R_f$))$_x$—$W_d$—(C($R_e$)($R_f$))$_y$—$W_i$-$E_j$-$W_g$—(C($R_e$)($R_f$))$_z$-T-Q;
a, b, c, d, g, i and j are each independently an integer from 0 to 3;
p, x, y and z are each independently an integer from 0 to 10;
W at each occurrence is independently —C(O)—, —C(S)—, -T-, —(C($R_e$)($R_f$))$_h$—, an alkyl group, an aryl group, a heterocyclic ring, an arylheterocyclic ring, or —($CH_2CH_2O$)$_q$—;
E at each occurrence is independently -T-, an alkyl group, an aryl group, —(C($R_e$)($R_f$))$_h$—, a heterocyclic ring, an arylheterocyclic ring, or —($CH_2CH_2O$)$_q$—;
h is an integer form 1 to 10;
q is an integer from 1 to 5;
$R_e$ and $R_f$ are each independently a hydrogen, an alkyl, a cycloalkoxy, a halogen, a hydroxy, an hydroxyalkyl, an alkoxyalkyl, an arylheterocyclic ring, an alkylaryl, an alkylcycloalkyl, an alkylheterocyclic ring, a cycloalkylalkyl, a cycloalkylthio, a cycloalkenyl, an heterocyclicalkyl, an alkoxy, a haloalkoxy, an amino, an alkylamino, a dialkylamino, an arylamino, a diarylamino, an alkylarylamino, an alkoxyhaloalkyl, a haloalkoxy, a sulfonic acid, a sulfonic ester, an alkylsulfonic acid, an arylsulfonic acid, an arylalkoxy, an alkylthio, an arylthio, a cyano an aminoalkyl, an aminoaryl, an aryl, an arylalkyl, an alkylaryl, a carboxamido, a alkylcarboxamido, an arylcarboxamido, an amidyl, a carboxyl, a carbamoyl, an alkylcarboxylic acid, an arylcarboxylic acid, an alkylcarbonyl, an arylcarbonyl, an ester, a carboxylic ester, an alkylcarboxylic ester, an arylcarboxylic ester, a haloalkoxy, a sulfonamido, an alkylsulfonamido, an arylsulfonamido, an alkylsulfonyl, an alkylsulfonyloxy, an arylsulfonyl, arylsulphonyloxy, a sulfonic ester, a urea, a phosphoryl, a nitro, $W_h$, -T-Q, or —(C($R_e$)($R_f$))$_k$-T-Q, or $R_e$ and $R_f$ taken together with the carbons to which they are attached form a carbonyl, a methanthial, a heterocyclic ring, a cycloalkyl group, an aryl group, an oxime or a bridged cycloalkyl group;
k is an integer from 1 to 3;
T at each occurrence is independently a covalent bond, a carbonyl, an oxygen, —S(O)$_o$— or —N($R_a$)$R_i$—;
o is an integer from 0 to 2;
$R_a$ is a lone pair of electrons, a hydrogen or an alkyl group;
$R_i$ is a hydrogen, an alkyl, an aryl, an alkylcarboxylic acid, an arylcarboxylic acid, an alkylcarboxylic ester, an arylcarboxylic ester, an alkylcarboxamido, an arylcarboxamido, an alkylaryl, an alkylsulfinyl, an alkylsulfonyl, an alkylsulfonyloxy, an arylsulfinyl, an arylsulfonyl, arylsulphonyloxy, a sulfonamido, a carboxamido, a carboxylic ester, an aminoalkyl, an aminoaryl, —$CH_2$—C(T-Q)($R_e$)($R_f$), a bond to an adjacent atom creating a double bond to that atom, —($N_2O_2$—)$^-$.$M^+$, wherein $M^+$ is an organic or inorganic cation;
with the proviso that the compound of Formula (I) must contain at least one nitrite, nitrate, thionitrite or thionitrate group;
wherein the compounds of Formula (IV) and Formula (V) are:

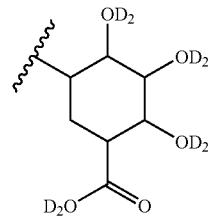

wherein:
$R_6$ at each occurrence is independently a hydrogen, a hydroxy or —OD;
D and $D_1$ is as defined herein; and
with the proviso that the compounds of Formula (IV) and Formula (V), must contain at least one nitrite, nitrate, thionitrite or thionitrate group.

7. The composition of claim 6, wherein the polymer is a synthetic polymer or a natural polymer selected from a polyolefin, a polyethylenimine, a polyethyleneimine derivative, a polyether, a polyanhydride, a polyhydroxybutyrate, a polyester, a polyamide, a polyurethane, a biopolymer, a starburst dendrimer, or a mixture thereof.

8. A medical device comprising the composition of claim 6, wherein the medical device is a balloon, a catheter tip, a stent, a catheter, a prosthetic heart valve, a synthetic vessel graft, an arteriovenous shunt, a heart valve, a suture, a vascular implant, a drug pump, a drug delivery catheter, plastic tubing, a dialysis bag, a lead, a pacemaker, an implantable pulse generator, an implantable cardiac defibrillator, a cardioverter defibrillator, a defibrillator, a spinal stimulator, a brain stimulator, a sacral nerve stimulator, a chemical sensor or a membrane surface.

9. The medical device of claim 8, wherein the composition coats all or a portion of the surface of the medical device.

10. The medical device of claim 8, wherein the composition forms all or part of the medical device.

\* \* \* \* \*